United States Patent
Wu et al.

(10) Patent No.: US 11,071,794 B2
(45) Date of Patent: Jul. 27, 2021

(54) DEUTERIUM SUBSTITUTED POSITRON EMISSION TOMOGRAPHY (PET) IMAGING AGENTS AND THEIR PHARMACOLOGICAL APPLICATION

(71) Applicant: Five Eleven Pharma Inc., Philadelphia, PA (US)

(72) Inventors: Zehui Wu, Philadelphia, PA (US); Zhihao Zha, Philadelphia, PA (US); Futao Liu, Philadelphia, PA (US); Karl Ploessl, Wilmington, DE (US); Seok Rye Choi, Aston, PA (US); Hank F. Kung, Springfield, PA (US)

(73) Assignee: Five Eleven Pharma Inc., Philadelphia, PA (US)

( * ) Notice: Subject to any disclaimer, the term of this patent is extended or adjusted under 35 U.S.C. 154(b) by 0 days.

(21) Appl. No.: 16/824,139

(22) Filed: Mar. 19, 2020

(65) Prior Publication Data

US 2020/0230263 A1 Jul. 23, 2020

Related U.S. Application Data

(62) Division of application No. 15/994,474, filed on May 31, 2018, now Pat. No. 10,912,849.

(60) Provisional application No. 62/513,217, filed on May 31, 2017.

(51) Int. Cl.

| | | |
|---|---|---|
| A61K 51/00 | (2006.01) |
| A61M 36/14 | (2006.01) |
| A61K 51/04 | (2006.01) |
| A61B 6/03 | (2006.01) |
| C07B 59/00 | (2006.01) |
| C07D 221/06 | (2006.01) |
| C07D 213/64 | (2006.01) |
| C07D 405/04 | (2006.01) |
| C07C 217/80 | (2006.01) |
| C07D 471/04 | (2006.01) |
| C07C 323/37 | (2006.01) |
| C07D 277/66 | (2006.01) |

(52) U.S. Cl.
CPC .......... *A61K 51/0455* (2013.01); *A61B 6/037* (2013.01); *A61K 51/04* (2013.01); *A61K 51/0419* (2013.01); *A61K 51/0431* (2013.01); *A61K 51/0453* (2013.01); *C07B 59/001* (2013.01); *C07B 59/002* (2013.01); *C07B 59/004* (2013.01); *C07C 217/80* (2013.01); *C07C 323/37* (2013.01); *C07D 213/64* (2013.01); *C07D 221/06* (2013.01); *C07D 405/04* (2013.01); *C07D 471/04* (2013.01); *C07B 2200/05* (2013.01); *C07D 277/66* (2013.01)

(58) Field of Classification Search
None
See application file for complete search history.

(56) References Cited

U.S. PATENT DOCUMENTS

| | | |
|---|---|---|
| 2008/0050312 A1 | 2/2008 | Kung et al. |
| 2010/0105653 A1 | 4/2010 | Besong et al. |
| 2010/0292478 A1 | 11/2010 | Cho et al. |
| 2014/0336386 A1 | 11/2014 | Sommer et al. |
| 2015/0157744 A1 | 6/2015 | Johnson et al. |
| 2016/0008494 A1 | 1/2016 | Kudo et al. |
| 2016/0213792 A1 | 7/2016 | Sundaram et al. |

OTHER PUBLICATIONS

Beauregard, J.M., and Beaulieu, A., "How we Read FCH-PET/CT for Prostate Cancer," Cancer Imaging 16(1):41, Springer Nature, United Kingdom (Dec. 2016).
Bousman, C.A., et al., "Antidepressant prescribing in the precision medicine era: a prescriber's primer on pharmacogenetic tools," BMC Psychiatry 17(1):60, BioMed Central, United Kingdom (Feb. 2017).
Chen, Y.A., et al., "Characterization of 4-[$^{18}$F]-ADAM as an Imaging Agent for SERT in Nonhuman Primate Brain Using PET: a Dynamic Study," Nuclear Medicine and Biology 39(2):279-285, Elsevier, United States (Feb. 2012).
Choi, S.R., et al., "Preclinical Properties of 18F-AV-45: a PET Agent for Abeta Plaques in the Brain," The Journal of Nuclear Medicine 50(11):1887-1894, Society of Nuclear Medicine, United States (Nov. 2009).
Ding, Y.S., et al., "PET Imaging of Norepinephrine Transporters," Current Pharmaceutical Design 12(30):3831-3845, Bentham Science Publishers, United Arab Emirates (2006).
Eriksson, O., et al., "In Vivo and in Vitro Characterization of [18F]-FE-(+)-DTBZ as a Tracer for Beta-Cell Mass," Nuclear Medicine and Biology 37(3):357-363, Elsevier, United States (Apr. 2010).
Fowler, J.S., et al., "Selective Reduction of Radiotracer Trapping by Deuterium Substitution: Comparison of Carbon-11-L-deprenyl and Carbon-11-deprenyl-D2 for Mao B Mapping," The Journal of Nuclear Medicine 36(7):1255-1262, Society of Nuclear Medicine, United States (Jul. 1995).
Fowler, J.S., et al., "Mapping Human Brain Monoamine Oxidase A and B With 11C-labeled Suicide Inactivators and PET," Science 235(4787):481-485, American Association for the Advancement of Science, United States (Jan. 1987).

(Continued)

*Primary Examiner* — Michael G. Hartley
*Assistant Examiner* — Melissa J Perreira
(74) *Attorney, Agent, or Firm* — Sterne, Kessler, Goldstein & Fox, P.L.L.C.

(57) ABSTRACT

The present invention relates to deuterated compounds according to Formula I-A, Formula II-A, Formula II-D, and Formula III-A. These compounds can be used as PET imaging agents for evaluating Parkinson's Disease, Alzheimer Disease, and for determining specific serotonin reuptake inhibitor (SSRIi) activity for treatment of depression. The present invention also relates to pharmaceutical compositions comprising a pharmaceutical acceptable carrier and a compound of Formula I-A, Formulae II-A, Formula II-D, or Formula III-A, or a pharmaceutically acceptable salt thereof.

13 Claims, No Drawings

(56) References Cited

OTHER PUBLICATIONS

Fowler, J.S., et al., "Translational Neuroimaging: Positron Emission Tomography Studies of Monoamine Oxidase," Molecular Imaging and Biology 7(6):377-387, Springer, United States (Nov.-Dec. 2005).

Frank, S., et al., "Effect of Deutetrabenazine on Chorea Among Patients With Huntington Disease: A Randomized Clinical Trial," JAMA 316(1):40-50, American Medical Association, United States (Jul. 2016).

Freeby, M., et al., "Vesicular Monoamine Transporter, Type 2 (VMAT2) Expression as It Compares to Insulin and Pancreatic Polypeptide in the Head, Body and Tail of the Human Pancreas," Islets 4(6):393-397, Taylor & Francis, United States (Nov.-Dec. 2012).

Gant, T.G, "Using Deuterium in Drug Discovery: Leaving the Label in the Drug," Journal of Medicinal Chemistry 57(9):3595-3611, American Chemical Society, United States (May 2014).

Garay, R.P., and Grossberg, G.T., "AVP-786 For the Treatment of Agitation in Dementia of the Alzheimer's Type," Expert Opinion on Investigational Drugs 26(1):121-132, Taylor & Francis, United Kingdom (Jan. 2017).

Gauthier, S., et al., "Why Has Therapy Development for Dementia Failed in the Last Two Decades?" Alzheimer's & Dementia 12(1):60-64, Elsevier Inc., United States (Jan. 2016).

Ginovart, N., et al., "Quantitative Validation of an Intracerebral Beta-sensitive Microprobe System to Determine in Vivo Drug-induced Receptor Occupancy Using [11C]Raclopride in Rats," Synapse 52(2):89-99, Wiley, United States (May 2004).

Goswami, R., et al., "Fluoroalkyl Derivatives of Dihydrotetrabenazine as Positron Emission Tomography Imaging Agents Targeting Vesicular Monoamine Transporters," Nuclear Medicine and Biology 33(6):685-694, Elsevier, United States (Aug. 2006).

Guengerich, F.P, "Kinetic Deuterium Isotope Effects in Cytochrome P450 Oxidation Reactions," Journal of Labelled Compounds and Radiopharmaceuticals 56(9-10):428-431, Wiley, United Kingdom (Jul.-Aug. 2013).

Harris, P.E., et al., "PET Quantification of Pancreatic VMAT 2 Binding Using (+) and (−) Enantiomers of [$^{18}$F]FP-DTBZ in Baboons," Nuclear Medicine and Biology 40(1):60-64, Elsevier, United States (Jan. 2013).

Harris, P.E., et al., "VMAT2 Gene Expression and Function as It Applies to Imaging Beta-cell Mass," Journal of Molecular Medicine 86(1):5-16, Springer International, Germany (Jan. 2008).

Harrison, J.R., and Owen, M.J., "Alzheimer's Disease: the Amyloid Hypothesis on Trial," British Journal of Psychiatry 208(1):1-3, Royal College of Psychiatrists, United Kingdom (Jan. 2016).

Hesse, S., et al., "Imaging of the Brain Serotonin Transporters (SERT) with 18F-Labelled Fluoromethyl-McN5652 and PET in Humans," European Journal of Nuclear Medicine and Molecular Imaging 39(6):1001-1011, Springer-Verlag Berlin, Germany (Jun. 2012).

Howland, R.H, "Deuterated Drugs," Journal of Psychosocial Nursing and Mental Health Services 53(9):13-16, C.B. Slack, United States (Sep. 2015).

Hsiao, I.T., et al., "Comparison of 99mTc-TRODAT-1 SPECT and 18 F-AV-133 PET Imaging in Healthy Controls and Parkinson's Disease Patients," Nuclear Medicine and Biology 41 (4):322-329, Elsevier, United States (Apr. 2014).

Hsiao, I.T., et al., "Correlation of Parkinson Disease Severity and 18F-DTBZ Positron Emission Tomograph," JAMA Neurology 71 (6):758-766, American Medical Association, United States (Jun. 2014).

Huang, W.S., et al., "PET Imaging of the Brain Serotonin Transporters (SERT) with N,N-dimethyl-2-(2-Amino-4-[18f]fluorophenylthio)benzylamine (4-[18f]-ADAM) in Humans: a Preliminary Study," European Journal of Nuclear Medicine and Molecular Imaging 40(1):115-124, Springer-Verlag Berlin, Germany (Jan. 2013).

Huang, Y., et al., "Development of Effective PET and SPECT Imaging Agents for the Serotonin Transporter: Has a Twenty-year Journey Reached Its Destination?" Current Topics in Medicinal Chemistry 10(15):1499-1526, Bentham Science Publishers, United Arab Emirates (2010).

Huang, Y.Y., et al., "Synthesis and Comparison of 4-[18F]F-ADAM, 2-[18F]F-ADAM, N-Desmethyl-4-[18F]F-ADAM and [18F]F-AFM as Serotonin Transporter Imaging Agents," Applied Radiation and Isotopes 70(10):2298-2307, Pergamon Press, United Kingdom (Oct. 2012).

Huang, Y., et al., "Fluorinated Diaryl Sulfides as Serotonin Transporter Ligands: Synthesis, Structure-activity Relationship Study, and in Vivo Evaluation of Fluorine-18-labeled Compounds as PET Imaging Agents," Journal of Medicinal Chemistry,48(7):2559-2570, American Chemical Society, United States (Apr. 2005).

Jahan, M., et al., "Decreased Defluorination Using the Novel Beta-cell Imaging Agent [18F]FE-DTBZ-d4 in pigs examined by PET," EJNMMI Research 1(1):33, Springer Berlin, Germany (Dec. 2011).

Jankovic, J., et al., "Deutetrabenazine in Tics Associated With Tourette Syndrome," Tremor and Other Hyperkinetic Movements (New York) 6:422, Center for Digital Research and Scholarship, United States (Nov. 2016).

Jarkas, N., et al., "Validation of Two Fluoro-analogues of N,N-dimethyl-2-(2'-amino-4'-hydroxymethyl-phenylthio)benzylamine as Serotonin Transporter Imaging Agents Using Micropet," Nuclear Medicine and Biology 37(5):593-603, Elsevier, United States (Jul. 2010).

Kambeitz, J.P and Howes, O.D, "The Serotonin Transporter in Depression: Meta-analysis of in Vivo and Post Mortem Findings and Implications for Understanding and Treating Depression," Journal of Affective Disorders 186:358-366, Elsevier/North-Holland Biomedical Press, Netherlands (Nov. 2015).

Kang, H.H., et al., "Investigating the Effects of Noise-induced Hearing Loss on Serotonin Transporters in Rat Brain Using 4-[18f]-adam/small Animal PET," Neuroimage 75:262-269, Academic Press, United States (Jul. 2013).

Kilbourn, M.R., et al., "Pharmacokinetics of [(18)F]fluoroalkyl Derivatives of Dihydrotetrabenazine in Rat and Monkey Brain," Nuclear Medicine and Biology 34(3):233-237, Elsevier, United States (Apr. 2007).

Kim, E., et al., "Altered Serotonin Transporter Binding Potential in Patients With Obsessive Compulsive Disorder Under Escitalopram Treatment: [11C]DASB PET Study," Psychological Medicine 46(2):357-366, Cambridge University Press, United Kingdom (Jan. 2016).

Kuchar, M and Mamat, C, "Methods to Increase the Metabolic Stability of (18)F-Radiotracers," Molecules 20(9): 16186-16220, MDPI, Switzerland (Sep. 2015).

Kung, H.F., et al., "18F Stilbenes and Styrylpyridines for PET Imaging of Abeta Plaques in Alzheimer's Disease: A Miniperspective," Journal of Medicinal Chemistry 53(3):933-941, American Chemical Society, United States (Feb. 2010).

Kung, H.F., et al., "2-(2-(Dimethylaminomethyl)phenoxy)-5-iodophenylamine: an Improved Serotonin Transporter Imaging Agent," Journal of Medicinal Chemistry 47(21):5258-5264, American Chemical Society, United States (Oct. 2004).

Kung, H.F, "The 13-Amyloid Hypothesis in Alzheimer's Disease: Seeing Is Believing," ACS Medicinal Chemistry Letters 3(4):265-267, American Chemical Society, United States (Apr. 2012).

Kung, M.P., et al., "In Vivo Imaging of Beta-cell Mass in Rats Using 18F-FP-(+)-DTBZ: a Potential PET Ligand for Studying Diabetes Mellitus," The Journal of Nuclear Medicine 49(7):1171-1176, Society of Nuclear Medicine, United States (Jul. 2008).

Kupers, R., et al., "Serotonin Transporter Binding in the Hypothalamus Correlates Negatively With Tonic Heat Pain Ratings in Healthy Subjects: a [11C]DASB PET Study," Neuroimage 54(2):1336-1343, Academic Press, United States (Jan. 2011).

Lin, K.S., et al., "Synthesis, Enantiomeric Resolution, F-18 Labeling and Biodistribution of Reboxetine Analogs: Promising Radioligands for Imaging the Norepinephrine Transporter With Positron Emission Tomography," Nuclear Medicine and Biology 32(4):415-422, Elsevier, United States (May 2005).

Logan, J., et al., "Reproducibility of Repeated Measures of Deuterium Substituted [11C]L-deprenyl ([11C]L-deprenyl-D2) Binding

(56) References Cited

OTHER PUBLICATIONS in the Human Brain," Nuclear Medicine and Biology 27(1):43-49, Elsevier, United States (Jan. 2000).
Mathis, C.A., et al., "Development of Positron Emission Tomography B-amyloid Plaque Imaging Agents," Seminars in Nuclear Medicine 42(6):423-432, W.B. Saunders, United States (Nov. 2012).
Mavel, S., et al., "Synthesis and in Vitro Evaluation of Fluorinated Diphenyloxide Derivatives and Sulfur Analogs as Serotonin Transporter Ligands," Bioorganic & Medicinal Chemistry 18(1):236-241, Elsevier Science, United Kingdom (Jan. 2010).
Meanwell, N.A, "Synopsis of Some Recent Tactical Application of Bioisosteres in Drug Design," Journal of Medicinal Chemistry 54(8):2529-2591, American Chemical Society, United States (Apr. 2011).
Nelissen, N., et al., "Phase 1 Study of the Pittsburgh Compound B Derivative 18F-flutemetamol in Healthy Volunteers and Patients with Probable Alzheimer Disease," The Journal of Nuclear Medicine 50(8):1251-1259, Society of Nuclear Medicine, United States (Aug. 2009).
Nitsch, S., et al., "Evaluation of Prostate Cancer With 11C- and 18F-choline PET/CT: Diagnosis and Initial Staging," The Journal of Nuclear Medicine 57(Suppl 3):38S-42S, Society of Nuclear Medicine, United States (Oct. 2016).
Normandin, M.D., et al., "In Vivo Imaging of Endogenous Pancreatic B-cell Mass in Healthy and Type 1 Diabetic Subjects Using 18f-fluoropropyl-dihydrotetrabenazine and PET," The Journal of Nuclear Medicine 53(6):908-916, Society of Nuclear Medicine, United States (Jun. 2012).
Okamura, N., et al., "In Vivo Measurement of Vesicular Monoamine Transporter Type 2 Density in Parkinson Disease with (18) F-AV-133," The Journal of Nuclear Medicine 51 (2):223-228, Society of Nuclear Medicine, United States (Feb. 2010).
Oya, S., et al., "5-Chloro-2-(2'-((Dimethylamino)methyl)-4'-iodophenylthio)benzenamine: a New Serotonin Transporter Ligand," Nuclear Medicine and Biology 34(2):129-139, Elsevier, United States (Feb. 2007).
Oya, S., et al., "New PET: Imaging Agent for the Serotonin Transporter: [(18)F]ACF (2-[(2-amino-4-chloro-5-fluorophenyl)thio]-N,N-dimethyl-benzenmethanamine)," Journal of Medicinal Chemistry 45(21):4716-4723, American Chemical Society, United States (Oct. 2002).
Paterson, L.M., et al., "5-HT Radioligands for Human Brain Imaging with PET and SPECT," Medicinal Research Reviews 33(1):54-111, Wiley, United States (Jan. 2013).
Patt, M., et al., "Metabolite Analysis of [$^{18}$F]Florbetaben (BAY 94-9172) in Human Subjects: a Substudy Within a Proof of Mechanism Clinical Trial," Journal of Radioanalytical and Nuclear Chemistry 284:557-562, Springer, Netherlands (Jun. 2010).
Qiao, H., et al., "One-step preparation of [(18)F]FPBM for PET imaging of serotonin transporter (SERT) in the brain," Nucl. Med. Biol. 43(8):470-7, Elsevier Inc., United States (2016).
Raffo, A., et al., "Role of Vesicular Monoamine Transporter Type 2 in Rodent Insulin Secretion and Glucose Metabolism Revealed by Its Specific Antagonist Tetrabenazine," Journal of Endocrinology 198(1):41-49, BioScientifica, United Kingdom (Jul. 2008).
Rowe, C.C., et al., "Head-to-head Comparison of 11C-PiB and 18F-AZD4694 (NAV4694) for beta-amyloid Imaging in Aging and Dementia," The Journal of Nuclear Medicine 54(6):880-886, Society of Nuclear Medicine, United States (Jun. 2013).
Rowe, C.C., et al., "Imaging of Amyloid Beta in Alzheimer's Disease with 18F-BAY94-9172, a novel PET Tracer: Proof of Mechanism," The Lancet Neurology 7(2):129-135, The Lancet Publishing Group, United Kingdom (Feb. 2008).
Rowe, C.C., et al., "Standardized Expression of 18F-NAV4694 and 11C-PiB 13-Amyloid PET Results With the Centiloid Scale," The Journal of Nuclear Medicine 57(8):1233-1237, Society of Nuclear Medicine, United States (Aug. 2016).
Shiue, G.G., et al., "N,N-dimethyl-2-(2-amino-4-(18)F-fluorophenylthio)-benzylamine (4-(18)F-ADAM): an Improved PET Radioligand for Serotonin Transporters," The Journal of Nuclear Medicine, 44(12):1890-1897, Society of Nuclear Medicine, United States (Dec. 2003).
Siderowf, A., et al., "PET Imaging of Amyloid with Florbetapir F 18 and PET imaging of Dopamine Degeneration With 18F-AV-133 (Florbenazine) in Patients With Alzheimer's Disease and Lewy Body Disorders," BMC Neurology 14:79, BioMed Central, United Kingdom (2014).
Smith, G., et al., "Radiosynthesis and Pre-clinical Evaluation of [(18)F]fluoro-[1,2-(2)H(4)] Choline," Nuclear Medicine and Biology 38(1):39-51, Elsevier, United States (Jan. 2011).
Spies, M., et al., "The Serotonin Transporter in Psychiatric Disorders: Insights From PET Imaging," The Lancet Psychiatry 2(8):743-755, Elsevier, United Kingdom (Aug. 2015).
Stehouwer, J.S and Goodman, M.M, "(11)C and (18)F PET Radioligands for the Serotonin Transporter (SERT)," Journal of Labelled Compounds and Radiopharmaceuticals 56(3-4):114-119, Wiley, United Kingdom (Mar.-Apr. 2013).
Szabo, Z., et al., "Positron Emission Tomography Imaging of Serotonin Transporters in the Human Brain Using [11C](+) McN5652," Synapse 20(1):37-43, Wiley, United States (May 1995).
Villemagne, V.L., et al., "A13-amyloid and Tau Imaging in Dementia," Seminars in Nuclear Medicine 47(1):75-88, W.B. Saunders, United States (Jan. 2017).
Villemagne, V.L., et al., "In Vivo Assessment of Vesicular Monoamine Transporter Type 2 in Dementia With Lewy Bodies and Alzheimer Disease," Archives of Neurology 68(7):905-912, American Medical Association, United States (Jul. 2011).
Wang, J., et al., "In vivo studies of the SERT-selective [18F]FPBM and VMAT2-selective [18F]AV-133 radiotracers in a rat model of Parkinson's disease," Nucl. Med. Biol. 37(4):479-86, Elsevier Inc., United States (2010).
Wang, J., et al., "In vivo characterization of a series of 18F-diaryl sulfides (18F-2-(2'-((dimethylamino)methyl)-4'-(fluoroalkoxy)phenylthio)benzenamine) for PET imaging of the serotonin transporter," J. Nucl. Med. 50(9):1509-17, Society of Nuclear Medicine and Molecular Imaging, China (2009).
Wang, J.L., et al., "2-(2'-(Dimethylamino)methyl)-4'-(3-[(18)F]Fluoropropoxy)-phenylthio)benzenamine for Positron Emission Tomography Imaging of Serotonin Transporters," Nuclear Medicine and Biology 35(4):447-458, Elsevier, United States (May 2008).
Wang, J.L., et al., "FlipADAM: a Potential New SPECT Imaging Agent for the Serotonin Transporter," Nuclear Medicine and Biology 37(5):577-586, Elsevier, United States (Jul. 2010).
Wilson, A.A., et al., "In Vitro and in Vivo Characterisation of [11C]-DASB: A Probe for in Vivo Measurements of the Serotonin Transporter by Positron Emission Tomography," Nuclear Medicine and Biology 29(5):509-515, Elsevier, United States (Jul. 2002).
Wilson, A.A., et al., "Novel Radiotracers for Imaging the Serotonin Transporter by Positron Emission Tomography: Synthesis, Radiosynthesis, and in Vitro and Ex Vivo Evaluation of (11)C-labeled 2-(phenylthio)araalkylamines," Journal of Medicinal Chemistry 43(16):3103-3110, American Chemical Society, United States (Aug. 2000).
Witney, T.H., et al., "Evaluation of Deuterated 18F- and 11C-labeled Choline Analogs for Cancer Detection by Positron Emission Tomography," Clinical Cancer Research 18(4):1063-1072, The Association, United States (Feb. 2012).
Wong, D.F., et al., "In Vivo Imaging of Amyloid Deposition in Alzheimer Disease Using the Radioligand 18F-AV-45 (florbetapir [corrected] F 18)," The Journal of Nuclear Medicine 51(6):913-920, Society of Nuclear Medicine, United States (Jun. 2010).
Zeng, F and Goodman, M.M , "Fluorine-18 Radiolabeled Heterocycles as Pet Tracers for Imaging B-amyloid Plaques in Alzheimer's Disease," Current Topics in Medicinal Chemistry 13(8):909-919, Bentham Science Publishers, United Arab Emirates (2013).
Zessin, J., et al., "Synthesis of S-([18F]fluoromethyl)-(+)-McN5652 as a Potential PET Radioligand for the Serotonin Transporter," Nuclear Medicine and Biology 28(7):857-863, Elsevier, United States (Oct. 2001).

(56) References Cited

OTHER PUBLICATIONS

Zhu, L., et al., "PET/SPECT Imaging Agents for Neurodegenerative Diseases," Chemical Society Reviews 43(19):6683-6691, Chemical Society, United Kingdom (Oct. 2014).

Zhu, L., et al., "An improved preparation of [18F]FPBM: A potential serotonin transporter (SERT) imaging agent," Nucl. Med. Biol. 40(8):974-9, Elsevier Inc., United States (2013).

Swahn, B.M., et al., "Synthesis and evaluation of pyridylbenzofuran, pyridylbenzothiazole and pyridylbenzoxazole derivatives as $^{18}$F-PET imaging agents for beta-amyloid plaques," Bioorganic & Medicinal Chemistry Letters 22 :4332-4337, Elsevier, Netherlands (2012).

Parhi, A.K., et al., "2-(2'-(((dimethylamino)methyl)-4'-(fluoroalkoxy)-phenylthio)benzenamine derivatives as serotonin transporter imaging agents," Journal of Medicinal Chemistry 50:6673-6684, American Chemical Society, United States (2007).

International Search Report and Written Opinion for International Application No. PCT/US2018/034691, ISA/US, Alexandria, Virginia, United States, dated Oct. 1, 2018, 11 pages.

Zhu, L., et al., "An improved radiosynthesis of [18F]AV-133: a PET imaging agent for vesicular monoamine transporter 2," Nucl Med Biol 37(2):133-141, Elsevier Inc., United States (2010).

International Preliminary Report on Patentability for International Application No. PCT/US2018/034691, ISA/US, Alexandria, Virginia, United States, dated Dec. 3, 2019, 8 pages.

DEUTERIUM SUBSTITUTED POSITRON EMISSION TOMOGRAPHY (PET) IMAGING AGENTS AND THEIR PHARMACOLOGICAL APPLICATION

BACKGROUND OF THE INVENTION

Deuterium (D) is a stable isotope of hydrogen (H). While the differences in the physical and chemical properties between hydrogen and deuterium are relatively small (Meanwell, J. Med. Chem. 2011, 54:2529-91), deuterated compounds can have significant effects on biological and chemical processes that were developed optimally for hydrogen. The deuterium substitution is slightly less lipophilic than hydrogen, Δ log P=−0.006 and the molar volume of deuterium is smaller than hydrogen by 0.140 cm$^3$/mol per atom. The carbon-deuterium (C-D) bonds are shorter than carbon hydrogen (C—H) bonds by 0.005 Å, therefore the activation energy for breaking a C-D vs C—H bond is significantly higher. Functionally, this reduces the cleavage rate for C-D bonds 6.7 times over C—H bonds (Kuchar, Molecules 2015, 20:16186-220), which can have a profound effect on drug pharmacokinetic properties.

Recent reports on deuterium substituted active pharmaceuticals have demonstrated benefits of the deuterium's kinetic isotope effect on the safety and clearance of drug substances and creation of new drugs through deuterated versions of existing molecules (Gant, J. Med. Chem. 2014, 57:3595-611). Some examples, such as tetrabenazine (NI-TOMAN or XENAZINE), deuterated tetrabenazine (SD-809, AUSTEDO), dextromethorphan, and D6-dextromethorphan (AVP-786) are shown below.

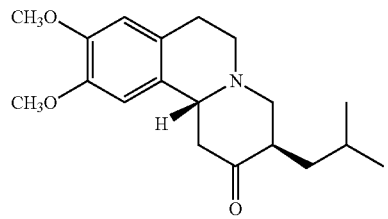

Tetrabenazine

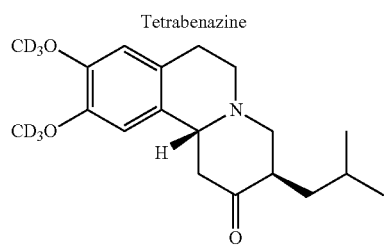

SD-809
Deuterated
Tetrabenazine

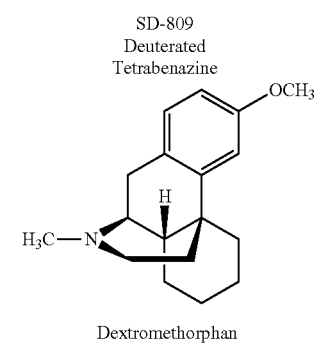

Dextromethorphan

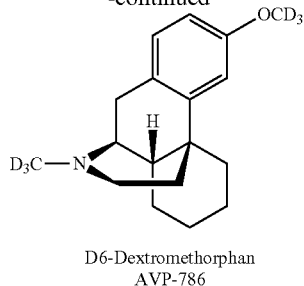

D6-Dextromethorphan
AVP-786

Deuterated tetrabenazine (SD-809) was recently approved by the FDA for treatment of chorea associated with Huntington's disease. Another example is AVP-786, deuterated dextromethorphan, which is designed to treat agitation in patients with Alzheimer disease (Garay, Expert Opin. Investig. Drugs 2017, 26:121-32).

The ability to moderate drug metabolism through hydrogen to deuterium substitution provides a novel approach in solving common complications of imaging agents—a lack of suitable resident time in vivo. In the past few decades there have been reports on using hydrogen to deuterium substitution to improve in vivo PET imaging agents (Kuchar, Molecules 2015, 20:16186-220; Guengerich, J Labelled Comp Radiopharm 2013, 56:428-31). A purpose of substituting deuterium for hydrogen is to slow down the in vivo metabolism to reduce the loss of radioactive tracer while maintaining binding capability for a specific enzyme or receptor binding site. One example is the use of $^{11}$C-L-deprenyl-D2 (instead of $^{11}$C-L-deprenyl) for mapping MAO-B enzyme (monoamine oxidase-B; amine oxygen oxidoreductase-B) activity in the brain (Fowler, J. Nucl. Med. 1995, 36:1255-62; Logan, Nucl. Med. Biol. 2000, 27:43-9).

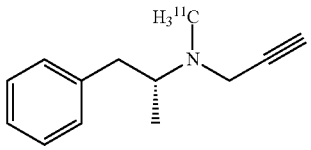

$^{11}$C-L-Deprenyl

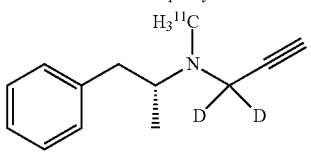

$^{11}$C-L-Deprenyl-D2

Another example of hydrogen to deuterium substitution for developing PET tracers is the tetra-deuterated $^{18}$F-fluoro-reboxetine-D4, which improved the in vivo stability of the deuterated PET tracers by retarding in vivo metabolism (Lin, Nucl. Med. Biol. 2005, 2:415-22; Ding, Curr. Pharm. Des. 2006, 12:3831-45). In addition, $^{11}$C-choline, $^{11}$C-D4-choline, $^{18}$F-fluoroethyl-choline and $^{18}$F-fluoroethyl-D4-choline have been compared in patients, to study tumor metabolic activity (Beauregard, Cancer Imaging 2016, 16:41; Nitsch, J. Nucl. Med. 2016, 57:38s-42s; Smith, Nucl. Med. Biol. 2011, 38:39-51; Witney, Clin. Cancer Res. 2012, 18:1063-72).

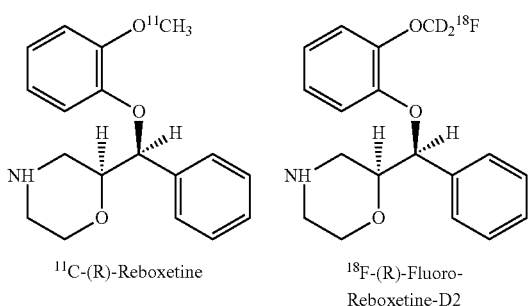

$^{11}$C-(R)-Reboxetine $^{18}$F-(R)-Fluoro-Reboxetine-D2

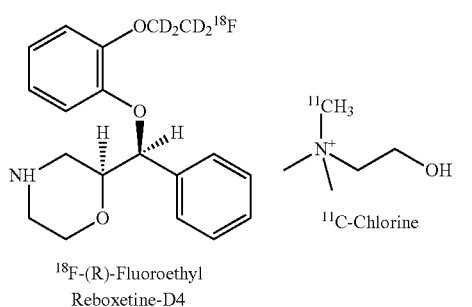

$^{18}$F-(R)-Fluoroethyl Reboxetine-D4

$^{11}$C-Choline

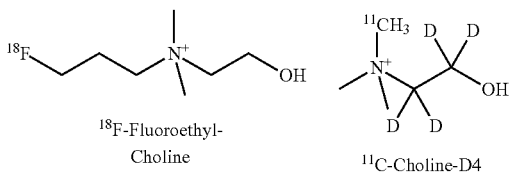

$^{18}$F-Fluoroethyl-Choline $^{11}$C-Choline-D4

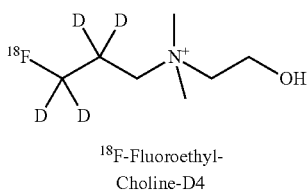

$^{18}$F-Fluoroethyl-Choline-D4

There exists a need to develop improved PET imaging agents, for example, using hydrogen to deuterium substitution, for evaluating conditions such as Parkinson's Disease, Alzheimer Disease, and serotonin transporter binding of specific serotonin reuptake inhibitor (SSRI) for treatment of depression.

BRIEF SUMMARY OF THE INVENTION

The present disclosure provides deuterium substituted tetrabenazine derivatives labeled with $^{18}$F as PET imaging agents for diagnosis of Parkinson's disease. Non radioactive deuterated derivatives provide drugs targeting vesicular monoamine transporter 2 for therapy of movement disorders.

In one embodiment, the present disclosure provides a compound having Formula I-A:

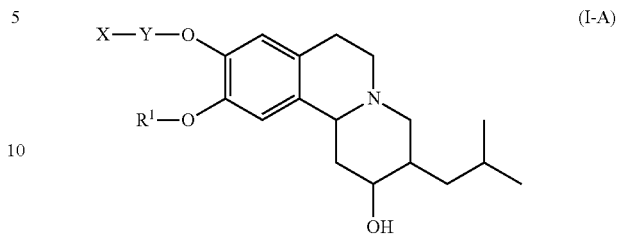

(I-A)

or a pharmaceutically acceptable salt thereof, wherein:
$R^1$ is $C_{1-4}$ alkyl and is optionally substituted with one or more deuterium atoms; and
X is $^{18}$F or $^{19}$F;
Y is $-(CR^aR^b)_n-$, wherein $R^a$ and $R^b$ are each independently hydrogen or deuterium atoms, n is an integer from 1 to 6;
provided that at least one deuterium atom is present at either $R^1$ or Y; and provided that when n is 2, $R^1$ is not $CH_3$.

The present disclosure also provides deuterium substituted compounds as a PET imaging agent for diagnosis of Alzheimer disease.

In one embodiment, the present disclosure provides a compound having Formula (II-A):

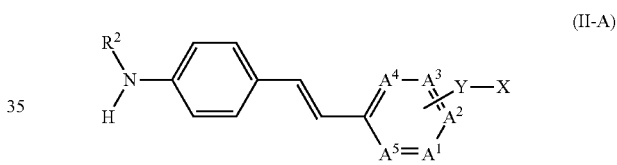

(II-A)

or a pharmaceutically acceptable salt thereof, wherein:
$R^2$ is $C_{1-4}$ alkyl and is optionally substituted with one or more deuterium atoms;
X is $^{18}$F or $^{19}$F;
Y is $-[O(CR^aR^b)_2]_m-$, wherein $R^a$ and $R^b$ are each independently hydrogen or deuterium atoms, and m is an integer from 1 to 6; and
$A^1, A^2, A^3, A^4$, and $A^5$ are each independently N, CH, or C and at most three of $A^1, A^2, A^3, A^4$, and $A^5$ are N;
provided that at least one deuterium atom is present at either $R^2$ or Y.

In another embodiment, the present disclosure provides a compound having Formula (II-D):

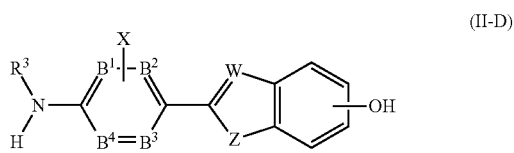

(II-D)

or a pharmaceutically acceptable salt thereof, wherein:
$R^3$ is $C_{1-4}$ alkyl, wherein $R^3$ is substituted with one or more deuterium atoms and one or more of carbon atoms of the $C_{1-4}$ alkyl are optionally $^{11}$C;
$B^1, B^2, B^3$, and $B^4$ are each independently C, N, or CH, and at most two of $B^1, B^2, B^3$, and $B^4$ are N;
X is hydrogen, $^{18}$F, or $^{19}$F;

W is N or CH; and

Z is O, S, or NH;

provided that the compound is labeled with $^{11}C$ or $^{18}F$.

The present disclosure further provides deuterium substituted diaryl sulfide compounds for PET imaging of serotonin transporters in the brain.

In one embodiment, the present disclosure provides a compound having Formula (III-A):

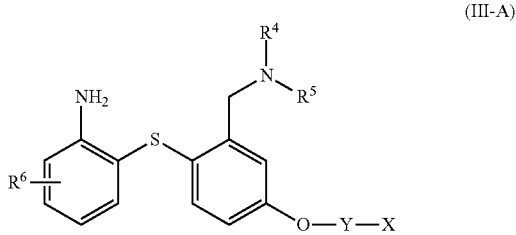

(III-A)

or a pharmaceutically acceptable salt thereof, wherein:

$R^4$ and $R^5$ are each independently hydrogen or $C_{1-4}$ alkyl, wherein the $C_{1-4}$ alkyl is optionally substituted with one or more deuterium atoms;

X is $^{18}F$ or $^{19}F$;

Y is $—(CR^aR^b)_n—$, wherein $R^a$ and $R^b$ are each independently hydrogen or deuterium atoms, and n is an integer from 1 to 6; and $R^6$ is hydrogen, halo, or CN;

provided that at least one deuterium atom is present at $R^4$, $R^5$, or Y.

In one embodiment, the present disclosure relates to a pharmaceutical composition comprising a deuterium substituted compound disclosed herein and a pharmaceutically acceptable carrier.

In one embodiment, the present disclosure relates to a method for imaging in a subject, comprising administering a radiolabeled compound disclosed herein to the subject; and obtaining an image of the subject or a portion of the subject.

In one embodiment, the present disclosure relates to a method of in vivo imaging, comprising administering an effective amount of a radiolabeled compound disclosed herein to a subject and detecting the pattern of radioactivity of the compound in the subject.

DETAILED DESCRIPTION OF THE INVENTION

The present disclosure provides novel deuterium substituted PET imaging agents for evaluating Parkinson's Disease, Alzheimer Disease, and for determining specific serotonin reuptake inhibitor (SSRI) activity for treatment of depression.

As used herein, "a," "an," or "the" means one or more unless otherwise specified.

The term "or" can be conjunctive or disjunctive.

Open terms such as "include," "including," "contain," "containing" and the like mean "comprising."

The term "about," as used herein, is intended to qualify the numerical values which it modifies, denoting such a value as variable within a margin of error. The term "about" should be understood to mean that range which would encompass the recited value and the range which would be included by rounding up or down to that figure as well, taking into account significant figures. The term "about" as used herein, includes the recited number ±10%. For example, "about 10" means 9 to 11.

When ranges of values are disclosed, and the notation "from $n_1$ ... to $n_2$" or "$n_1$-$n_2$" is used, where $n_1$ and $n_2$ are the numbers, then unless otherwise specified, this notation is intended to include the numbers themselves and the range between them. This range may be integral or continuous between and including the end values.

The term "deuterium enrichment" refers to the percentage of incorporation of deuterium at a given position in a compound in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "deuterium enrichment factor," as used herein, means the ratio between the isotopic abundance and the natural abundance of deuterium. For example, a position designated as having deuterium can have a minimum isotopic enrichment factor of at least 3340 (50.1% deuterium incorporation) at each atom designated as deuterium in a compound disclosed herein.

In some embodiments, a compound of the present disclosure has an isotopic enrichment factor for each designated deuterium atom of at least 3500 (54.6% deuterium incorporation at each designated deuterium atom), at least 4000 (62.4% deuterium incorporation), at least 4500 (70.2% deuterium incorporation), at least 5000 (78% deuterium), at least 5500 (85.8% deuterium incorporation), at least 6000 (93.6% deuterium incorporation), at least 6090 (95% deuterium incorporation), at least 6218 (97% deuterium incorporation), at least 6346 (99% deuterium incorporation), or at least 6378 (99.5% deuterium incorporation).

The term "is/are deuterium," when used to describe a given position in a compound disclosed herein or the symbol "D," when used to represent a given position in a drawing of a compound, means that the specified position is enriched with deuterium above the naturally occurring distribution of deuterium. In some embodiments, deuterium enrichment is at least about 1%, at least about 5%, at least about 10%, at least about 20%, at least about 50%, at least about 70%, at least about 80%, at least about 90%, at least about 95%, at least about 97%, at least about 98%, or at least about 99% of deuterium at the specified position.

The deuterated compounds disclosed herein can be prepared using commercially available deuterium-containing starting materials. Many deuterium-containing starting materials have >99% deuterium enrichment at the specified position.

Some of the compounds disclosed herein contain one or more asymmetric centers and may thus give rise to enantiomers, diastereomers, and other stereoisomeric forms. The invention is meant to encompass the compounds in all such possible forms, as well as their racemic and resolved forms and mixtures thereof.

Certain compounds disclosed herein are labeled with a radioactive fluorine atom $^{18}F$. Certain other compounds disclosed herein contain the stable isotope of fluorine, $^{19}F$, which is used interchangeably with F herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

The term "pharmaceutically acceptable salts" embraces salts with inorganic and organic acids, and inorganic and organic bases. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

The term "treating" or "treatment" refers to administering a therapy in an amount, manner, or mode effective to improve a condition, symptom, or parameter associated with a disorder or to slow or prevent progression of a disorder, to either a statistically significant degree or to a degree detectable to one skilled in the art. An effective amount, manner, or mode can vary depending on the subject and may be tailored to the subject. A subject includes, but is not limited to, a human or an animal.

Deuterated $^{18}$F—FP-DTBZ ($^{18}$F-AV-133) as a Vesicular Monoamine Transporter 2 (VMAT2) Imaging Agent Fluoroalkyl derivatives of dihydroxy-tetrabenazine have been prepared and tested as imaging agents for vesicular monoamine transporter 2 (VMAT2) in the brain (Goswami, Nucl. Med. Biol. 2006, 33:685-94; Kilbourn, Nucl. Med. Biol. 2007, 34:233-7). PET imaging using $^{11}$C-dihydrotetrabenazine, ($^{11}$C-DTBZ) is useful to map the distribution VMAT2 in neurons. The $^{18}$F labeled FP-DTBZ ($^{18}$F—FP-(+)-DTBZ, $^{18}$F-AV-133), with a longer physical half-life, has also been developed. In the past few years, several reports have described the clinical usefulness of $^{18}$F-AV-133 as a VMAT2 imaging agent. Results of human clinical studies for $^{18}$F-AV-133/PET have suggested that it is a useful agent in assisting diagnosis and monitoring of Parkinson's disease.

In relation to the discovery of the effects of deuterium on metabolic clearance, an additional area of use for $^{18}$F-AV-133/PET that demonstrated this effect, was in visualizing beta cells within the pancreas. It was proposed that the VMAT2 binding in the pancreas may be a useful indicator for measuring beta cell mass, which is significantly reduced in patients with diabetes (Kung, J. Nucl. Med. 2008, 49:1171-6; Raffo, J. Endocrinol. 2008, 198:41-9; Harris, J. Mol. Med. 2008, 86:5-16; Harris, Nucl. Med. Biol. 2013, 40:60-4; Freeby, Islets 2012, 4:393-7).

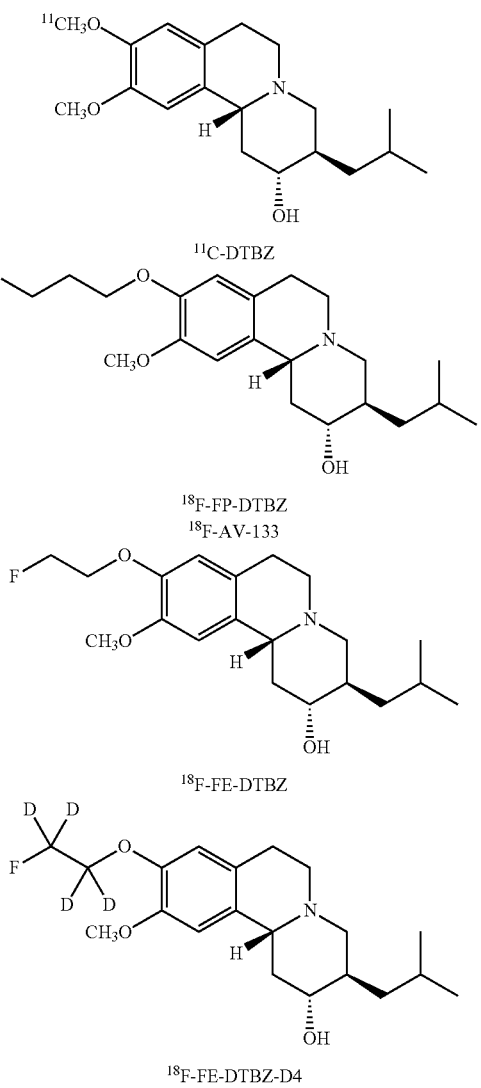

Both of $^{11}$C-DTBZ and $^{18}$F—FP-DTBZ have been tested in humans as vesicular monoamine transporter 2 (VMAT2) imaging agents for diagnosis of Parkinson's disease. $^{18}$F—FE-DTBZ has also been investigated as a potential pancreas imaging agent.

In an effort to develop additional VMAT2 imaging agents specifically targeting beta cells, similar derivatives, $^{18}$F-fluoroethyl-DTBZ (FE-DTBZ) and the corresponding deuterated $^{18}$F-fluoroethyl-DTBZ-D4 ($^{18}$F—FE-D4-DTBZ-D4), have been prepared for imaging VMAT2 in the pancreas (Eriksson, Nucl. Med. Biol. 2010, 37:357-63; Jahan, EJNMMI Res 2011, 1:33).

Of additional note to these studies, there may be side products produced during the preparation of $^{18}$F—FP-DTBZ. It is likely that one of the impurities was derived from a nucleophilic substitution of the fluoride ion that induced an elimination reaction instead. The elimination reaction likely occurred by breaking the C—H bond first, which led to the elimination reaction. Without wishing to be bound by theory, it is believed that substituting the hydrogen atoms with deuterium on the $^{18}$F propyl group can reduce the elimination reaction, and thus improve the labeling reaction (Scheme 1). In addition, the deuterium atoms on the fluoropropyl group can provide the compounds with better in vivo stability for imaging VMAT2 binding sites in the brain of Parkinson's patients.
The present disclosure provides deuterium substituted tetrabenazine derivatives as a PET imaging agent for diagnosis and therapy of Parkinson's disease.
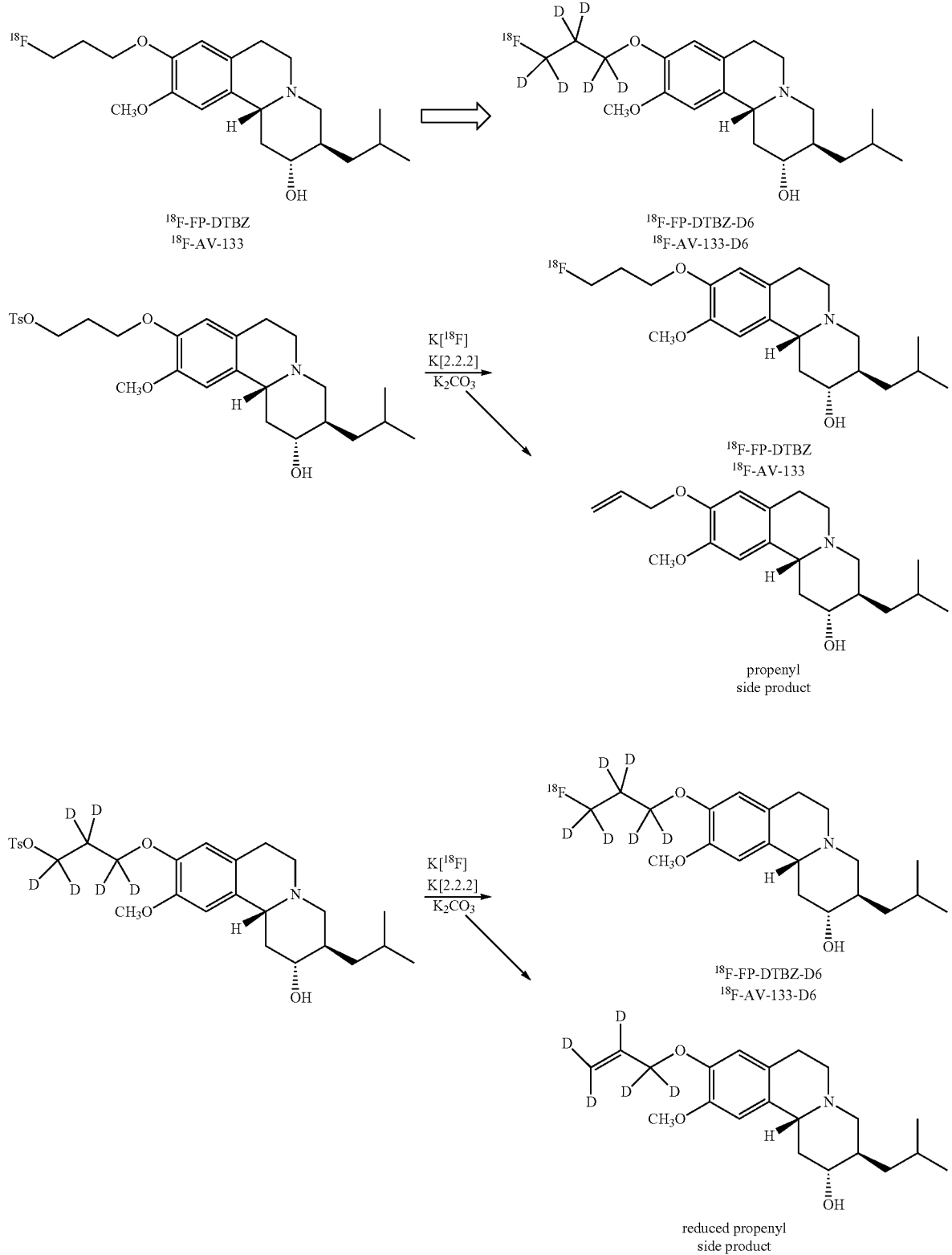
Scheme 1

In one embodiment, the present disclosure provides a compound having Formula I-A:

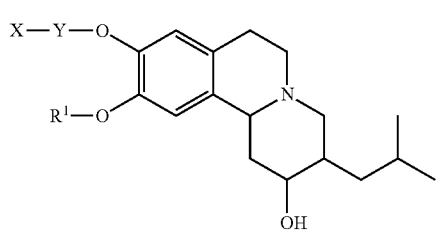

(I-A)

or a pharmaceutically acceptable salt thereof, wherein:

$R^1$ is $C_{1-4}$ alkyl and is optionally substituted with one or more deuterium atoms; and X is $^{18}F$ or $^{19}F$;

Y is —$(CR^aR^b)_n$—, wherein $R^a$ and $R^b$ are each independently hydrogen or deuterium atoms, n is an integer from 1 to 6;

provided that at least one deuterium atom is present at either $R^1$ or Y; and provided that when n is 2, $R^1$ is not $CH_3$.

One embodiment of the present disclosure provides a compound of Formula I-A wherein n is 3, 4, 5, or 6. In some embodiments, n is 3. In some embodiments, Y is —$(CH_2)_2$—, —$(CD_2)_2$-, —$(CH_2)_3$—, —$(CD_2)_3$-, —$(CH_2)_4$—, —$(CD_2)_4$-, —$(CH_2)_5$—, —$(CD_2)_5$-, —$(CH_2)_6$—, or —$(CD_2)_6$-. In some embodiments, Y is —$(CH_2)_3$— or —$(CD_2)_3$-.

One embodiment of the present disclosure provides a compound of Formula I-A wherein $R^1$ is $C_{1-4}$ alkyl that can be deuterated or non-deuterated. In some embodiments, $R^1$ is —$CH_3$, —$CD_3$, —$CH_2CH_3$, —$CD_2CD_3$, —$CD_2CH_3$, —$CH_2CD_3$, —$CH(CH_3)_2$, —$CD(CD_3)_2$, —$CH(CD_3)_2$, —$CD(CH_3)_2$, —$CH_2CH(CH_3)_2$, —$CD_2CH(CH_3)_2$, —$CH_2CD(CH_3)_2$, —$CH_2CH(CD_3)_2$, —$CD_2CD$ $(CH_3)_2$, —$CD_2CH(CD_3)_2$, —$CH_2CD(CD_3)_2$, or —$CD_2CD$ $(CD_3)_2$. In some of these embodiments, $R^1$ is —$CD_3$, —$CD_2CD_3$, —$CD_2CH_3$, —$CH_2CD_3$, —$CD(CD_3)_2$, —$CH(CD_3)_2$, —$CD(CH_3)_2$, —$CD_2CH(CH_3)_2$, —$CH_2CD$ $(CH_3)_2$, —$CH_2CH(CD_3)_2$, —$CD_2CD(CH_3)_2$, —$CD_2CH$ $(CD_3)_2$, —$CH_2CD(CD_3)_2$, or —$CD_2CD(CD_3)_2$. In some embodiments, $R^1$ is —$CH_3$ or —$CD_3$. In some embodiments, $R^1$ is —$CD_3$.

In some embodiments, the compound of Formula I-A has the following formula:

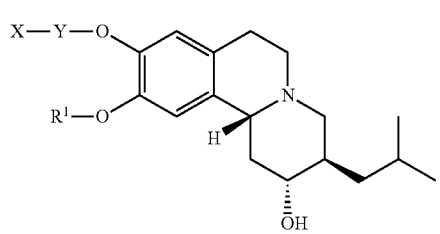

(I-B)

or a pharmaceutically acceptable salt thereof, wherein X, Y, and $R^1$ are as defined herein.

In some embodiments, the compound of Formula I-A has the following formula:

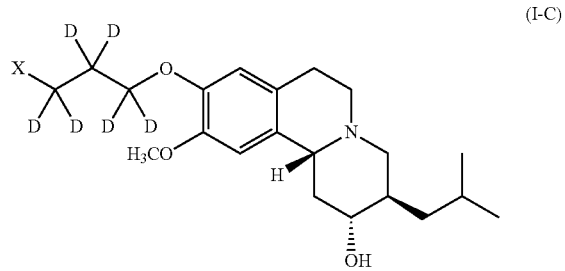

(I-C)

or a pharmaceutically acceptable salt thereof, wherein X is $^{18}F$ or $^{19}F$.

In some embodiments, the compound of Formula I-A has the following formula:

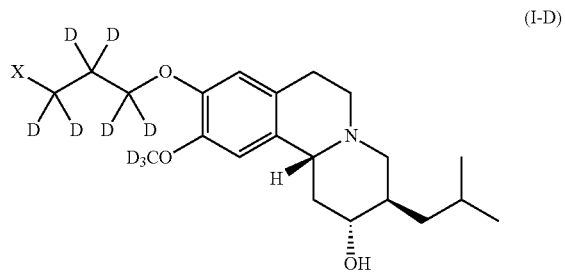

(I-D)

or a pharmaceutically acceptable salt thereof, wherein X is $^{18}F$ or $^{19}F$.

In one embodiment, the compound of Formula I-A is:

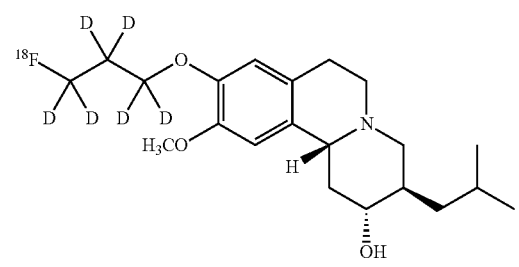 [SMILES: [2H]C([2H])([18F])C([2H])([2H])C([2H])([2H])Oc1cc2c(cc1OC)[C@H]1C[C@@H](O)[C@H](CC(C)C)CN1CC2]

or a pharmaceutically acceptable salt thereof.

In one embodiment, the compound of Formula I-A is:

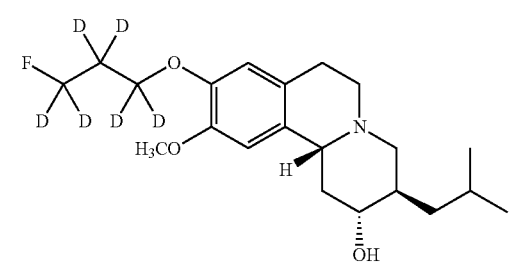 [SMILES: [2H]C([2H])(F)C([2H])([2H])C([2H])([2H])Oc1cc2c(cc1OC)[C@H]1C[C@@H](O)[C@H](CC(C)C)CN1CC2]

or a pharmaceutically acceptable salt thereof.

In one embodiment, the compound of Formula I-A is:

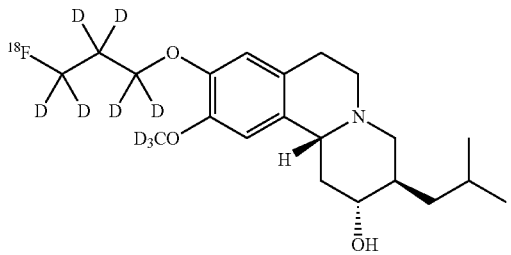

or a pharmaceutically acceptable salt thereof.

In one embodiment, the compound of Formula I-A is:

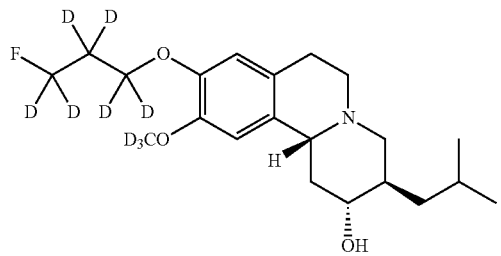

or a pharmaceutically acceptable salt thereof.

The present disclosure provides a method for diagnosing Parkinson's disease in a subject in need thereof comprising administering an effective amount of a compound of Formula I-A or a pharmaceutically acceptable salt thereof to the subject and obtaining an image of the subject or a portion of the subject. In some embodiments, the method for diagnosing Parkinson's disease comprising administering an effective amount of a compound of Formula I-A disclosed herein wherein X is $^{18}$F.

The present disclosure also provides a method for treating Parkinson's disease in a subject in need thereof comprising administering a therapeutically effective amount of a compound of Formula I-A or a pharmaceutically acceptable salt thereof to the subject. In some embodiments, the method for treating Parkinson's disease in a subject in need thereof comprising administering a therapeutically effective amount of a compound of Formula I-A disclosed herein wherein X is $^{19}$F.

Certain compounds disclosed herein may possess useful VMAT2 inhibiting activity, and may be used in the treatment or prophylaxis of a disorder in which VMAT2 plays an active role. Certain embodiments provide methods for inhibiting VMAT2. Other embodiments provide methods for treating a VMAT2-mediated disorder in a subject in need of such treatment, comprising administering to the subject a therapeutically effective amount of a compound of Formula I-A. Also provided is the use of certain compounds disclosed herein in the manufacture of a medicament for the treatment of a disorder ameliorated by the inhibition of VMAT2.

The term "VMAT2-mediated disorder" refers to a disorder that is characterized by abnormal VMAT2 activity. A VMAT2-mediated disorder may be completely or partially mediated by modulating VMAT2. In particular, a VMAT2-mediated disorder is one in which inhibition of VMAT2 results in some effect on the underlying disorder.

VMAT2-mediated disorders, include, but are not limited to, chronic hyperkinetic movement disorders, and/or any disorder which can lessened, alleviated, or prevented by administering a VMAT2 inhibitor. The term "chronic hyperkinetic movement disorders" refers to disorders characterized by non-purposeful, repetitive, disordered motor acts, variously termed "compulsive", "rhythmical", or "stereotyped." In humans, chronic hyperkinetic movement disorders can be psychogenic (e.g., tics), idiopathic (as in, e.g., Tourette's syndrome and Parkinson's disease, genetic (as in, e.g., the chorea characteristic of Huntington's Disease), infectious (as in, e.g., Sydenham's Chorea), or, as in tardive dyskinesia, drug-induced. Unless otherwise stated, "chronic hyperkinetic movement disorders" refers to and includes all psychogenic, idiopathic, genetic, and drug-induced movement disorders.

In certain embodiments, the chronic hyperkinetic movement disorder is Huntington's disease. In certain embodiments, the chronic hyperkinetic movement disorder is Parkinson's disease.

Deuterated amyloid Imaging Agents for Alzheimer Disease

In Alzheimer disease (AD) β-amyloid peptide (Aβ) aggregates are deposited in extracellular plaques typically composed of straight fibrils. These structures are also found in normal aging and are sometimes referred to as senile plaques. Aβ plaque deposition (i.e. Amyloid hypothesis) is considered the key pathophysiological event leading to AD (Gauthier, Alzheimer Dement 2016, 12:60-4; Harrison, Br. J. Psychiatry 2016, 208:1-3). Research into Aβ plaque-specific imaging agents is one of the most fascinating developments in the field of brain imaging over the past fifteen years, and has been extensively reviewed. The most well characterized PET imaging agent for Aβ plaques in the brain is $^{11}$C-6-OH-BTA-1, ($^{11}$C—PIB) (Mathis, Semin. Nucl. Med. 2012, 42:423-32), and has been used as a tracer for imaging Aβ plaques in the brain of suspected AD patients. Many different core structures have been prepared and tested. Among the hundreds of potential ligands that show good binding to Aβ plaques, four $^{18}$F labeled tracers, suitable for commercial distribution, have been successfully tested in humans (Kung, A C S Med Chem Lett 2012, 3:265-7; Villemagne, Semin. Nucl. Med. 2017, 47:75-88), and the FDA has approved three (AMYVID, NEURACEQ, and VIZAMYL) for human Aβ imaging (Scheme 2). Another Aβ plaque imaging agent, structurally similar to flutemetamol (VIZAMYL), NAV4694, has also shown excellent in vitro binding and promising in vivo kinetics in human studies (Rowe, J. Nucl. Med. 2013, 54:880-6).

Scheme 2

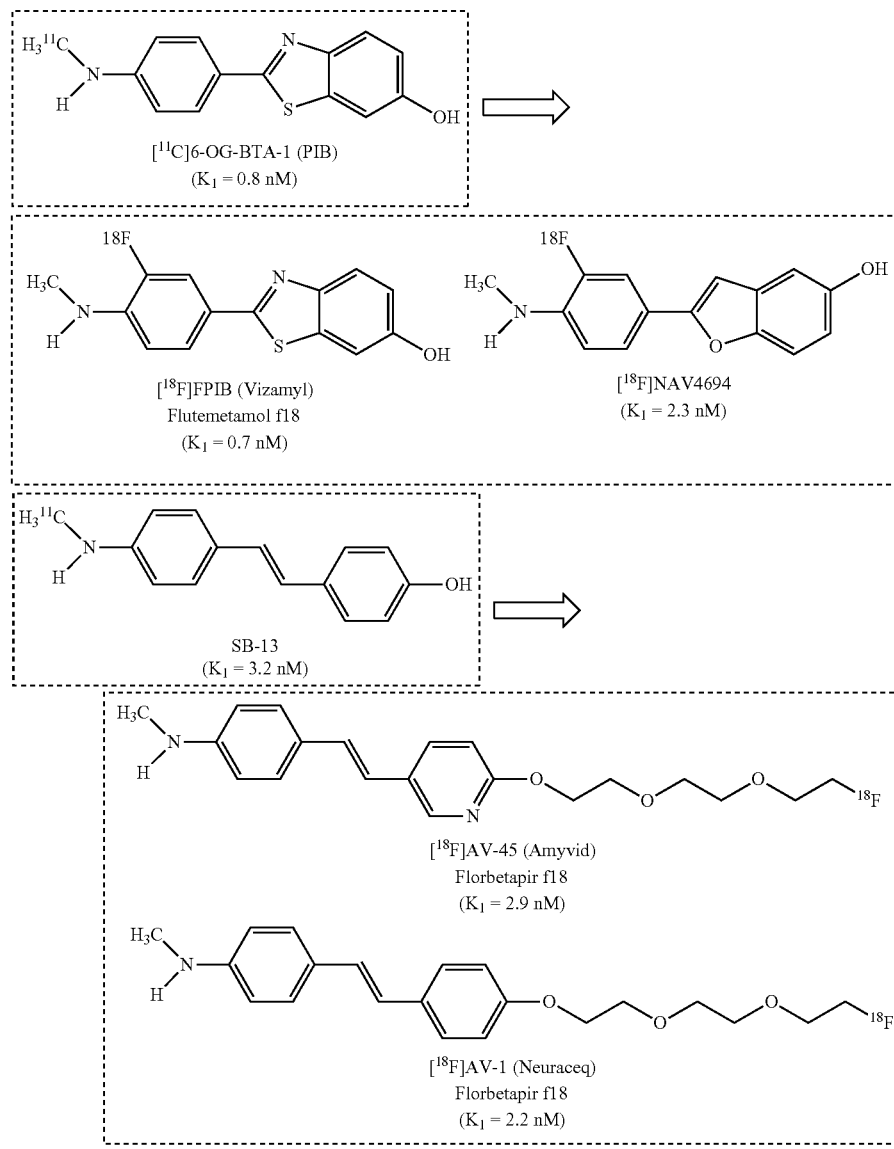

[11C]6-OG-BTA-1 (PIB)
($K_i$ = 0.8 nM)

[18F]FPIB (Vizamyl)
Flutemetamol f18
($K_i$ = 0.7 nM)

[18F]NAV4694
($K_i$ = 2.3 nM)

SB-13
($K_i$ = 3.2 nM)

[18F]AV-45 (Amyvid)
Florbetapir f18
($K_i$ = 2.9 nM)

[18F]AV-1 (Neuraceq)
Florbetapir f18
($K_i$ = 2.2 nM)

11C—PIB was the first agent tested in humans, which led to the development of 18F-Vizamyl and NAV4694. Additionally, modifying 11C—SB-13 led to the discovery of stilbene and the styrylpyridine series of agents. Three units of polyethylene glycol chains were attached to the core. The polyethylene glycol chains are useful for adjusting the lipophilicity and providing a suitable position for fluorine substitution. All of these PET imaging agents contain an N-methyl group attached to a phenyl ring. The electron donating N-methyl anilinyl group plays an important role in binding the target sites in the Aβ plaques. Without wishing to be bound by theory, it is believed that substituting the N-methyl group with a deuterated N-methyl group can reduce the N-demethylation reaction in vivo.

Previous reports on in vivo metabolism of 18F-AV-45 (AMYVID) showed a rapid change in the plasma after intravenous (i.v.) injection. In vivo metabolism of 18F-AV-45 in mice showed that, at 30 min after an intravenous injection, only 30% of the parent 18F-AV-45 remained in the plasma. The biologic $T_{1/2}$ of 18F-AV-45 in mouse plasma was estimated to be less than 30 min. Metabolite profiling and identification of the metabolites were done by HPLC with radioactive detection and liquid chromatography/mass spectroscopy analysis. One of the plasma metabolites was N-demethylated 18F-AV-160, which constituted about 48% of the metabolites at 30 min after injection (Scheme 3). The brain uptake of 18F-AV-160 at 2 min after injection was 4.5% ID/g of tissue, and decreased to 1.8% ID/g at 60 min. The initial uptake of the parent 18F-AV-45 was 1.5-fold higher than this metabolite. No significant binding to Aβ plaques was observed with the metabolites using AD brain-section autoradiography and the in vitro AD brain homogenate binding assay. The inhibition constant of AV-160 ($K_i$=54±5 nM) indicates at least a 20-fold reduction of binding affinity to Aβ plaques in AD brain tissue homogenates, as compared with that of the nonradioactive version of 18F-AV-45 ($K_i$=2.87±0.17 nM) (Choi, J. Nucl. Med. 2009, 50:1887-94).

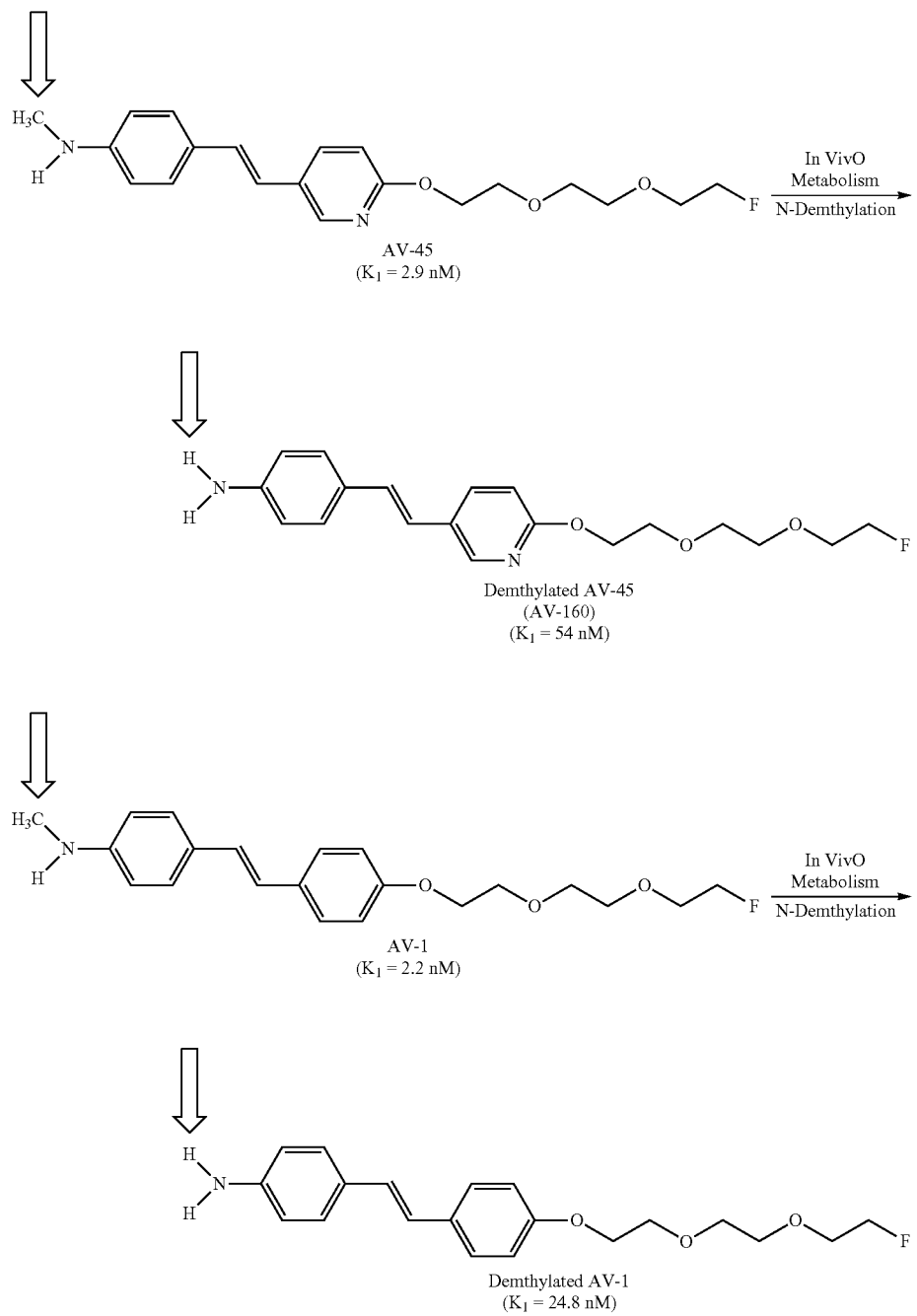

Scheme 3

In humans, the in vivo metabolism was found to be similar to that in mice (Wong, J. Nucl. Med. 2010, 51:913-20). After an injection of $^{18}$F-AV-45, the total radioactivity in plasma and the fraction of plasma radioactivity accounted for by $^{18}$F-AV-45 were rapidly reduced. Plasma radioactivity was decreased by approximately 80% within 10 min and by approximately 90% within 20 min of the injection. In addition to the parent compound, $^{18}$F-AV-45, three metabolite peaks were observed in human plasma. One of the major peaks was matched to cold reference as desmethyl-$^{18}$F-AV-45 (N-desmethyl $^{18}$F-AV-45, i.e., $^{18}$F-AV-160). In comparison, $^{18}$F-AV-1 (NUERACEQ) also displayed a rapid in vivo metabolism; one of the major metabolites in human plasma was the N-desmethyl $^{18}$F-AV-1 (see Scheme 3). It is believed that the N-demethylation leads to reduced binding affinities towards Aβ plaques in the brain, and contributes to increased non-specific binding. Therefore, a novel strategy to reduce the in vivo production of $^{18}$F-AV-160 by slowing the N-demethylation process by substituting a deuterated N-methyl group on AV-45, should improve imaging by increased uptake of $^{18}$F-AV-45 to Aβ plaques in the brain and a decrease of non-specific binding (Scheme 4).

Scheme 4

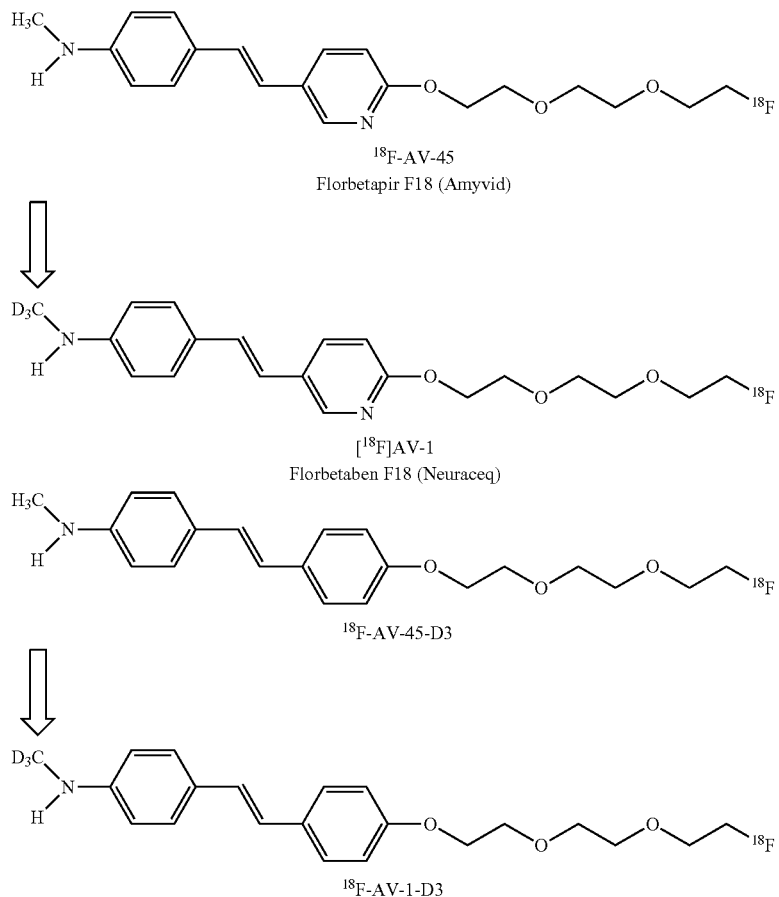

The inventors have discovered that the in vivo stability of the N-methyl-aniline group is enhanced by substitution of deuterated methyl groups for both AV-45 and AV-1. The deuterated agent, $^{18}$F-AV-45-D3 showed excellent brain uptake comparable to that observed to $^{18}$F-AV-45 after an i.v. injection in mice.

The present disclosure provides deuterium substituted compounds as a PET imaging agent for diagnosis of Alzheimer disease.

In one embodiment, the present disclosure provides a compound having Formula II-A:

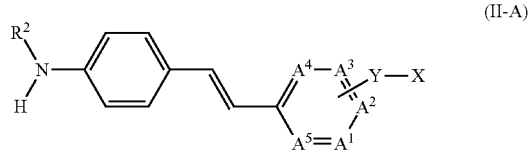

(II-A)

or a pharmaceutically acceptable salt thereof, wherein:
$R^2$ is $C_{1-4}$ alkyl and is optionally substituted with one or more deuterium atoms;
X is $^{18}$F or F;
Y is $-[O(CR^aR^b)_2]_m-$, wherein $R^a$ and $R^b$ are each independently hydrogen or deuterium atoms, and m is an integer from 1 to 6; and $A^1$, $A^2$, $A^3$, $A^4$, and $A^5$ are each independently N, CH, or C and at most three of $A^1$, $A^2$, $A^3$, $A^4$, and $A^5$ are N;

provided that at least one deuterium atom is present at either $R^2$ or Y.

One embodiment of the present disclosure provides a compound of Formula II-A wherein $R^2$ is $C_{1-4}$ alkyl that can be deuterated or non-deuterated. In some embodiments, $R^2$ is $-CH_3$, $-CD_3$, $-CH_2CH_3$, $-CD_2CD_3$, $-CD_2CH_3$, $-CH_2CD_3$, $-CH(CH_3)_2$, $-CD(CD_3)_2$, $-CH(CD_3)_2$, $-CD(CH_3)_2$, $-CH_2CH(CH_3)_2$, $-CD_2CH(CH_3)_2$, $-CH_2CD(CH_3)_2$, $-CH_2CH(CD_3)_2$, $-CD_2CD(CH_3)_2$, $-CD_2CH(CD_3)_2$, $-CH_2CD(CD_3)_2$, or $-CD_2CD(CD_3)_2$. In some of these embodiments, $R^2$ is $-CD_3$, $-CD_2CD_3$, $-CD_2CH_3$, $-CH_2CD_3$, $-CD(CD_3)_2$, $-CH(CD_3)_2$, $-CD(CH_3)_2$, $-CD_2CH(CH_3)_2$, $-CH_2CD$ $(CH_3)_2$, $-CH_2CH(CD_3)_2$, $-CD_2CD(CH_3)_2$, $-CD_2CH$ $(CD_3)_2$, $-CH_2CD(CD_3)_2$, or $-CD_2CD(CD_3)_2$. In some embodiments, $R^2$ is $-CH_3$ or $-CD_3$. In some embodiments, $R^2$ is $-CD_3$.

One embodiment of the present disclosure provides a compound of Formula II-A wherein m is 1, 2, 3, or 4. In one embodiment, m is 3. In some embodiments, Y is $-[OCH_2CH_2]_m-$ or $-[OCD_2CD_2]_m-$. In some embodiments, Y is $-[OCH_2CH_2]_3-$ or $-[OCD_2CD_2]_3-$. In some embodiments, Y is $-[OCD_2CD_2]_3-$.

In some embodiments, the present disclosure provides a compound of Formula II-A having the following formulae:

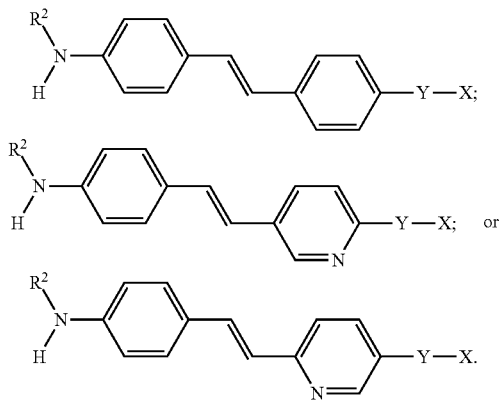

or a pharmaceutically acceptable salt thereof, wherein $R^2$, X, and Y are as defined herein.

In some embodiments, the compound of Formula II-A has the following formula:

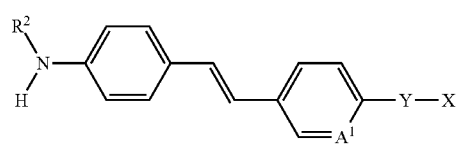

(II-B)

or a pharmaceutically acceptable salt thereof, wherein:
$R^2$ is $C_{1-2}$ alkyl and is optionally substituted with one or more deuterium atoms;
X is $^{18}F$ or $^{19}F$;
Y is $-[O(CR^aR^b)_2]_m-$, wherein $R^a$ and $R^b$ are each independently hydrogen or deuterium atoms, and m is an integer from 1 to 4; and
$A^1$ is N or CH;
provided that at least one deuterium atom is present at either $R^2$ or Y.

In some embodiments, the compound of Formula II-A has the following formula:

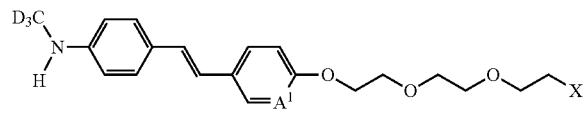

(II-C)

or a pharmaceutically acceptable salt thereof, wherein:
$A^1$ is N or CH; and
X is $^{18}F$ or $^{19}F$.

In one embodiment, the compound of Formula II-A is:

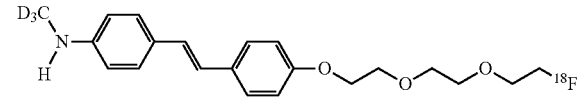 [SMILES: [2H]C([2H])([2H])Nc1ccc(/C=C/c2ccc(OCCOCCOCC[18F])cc2)cc1]

or a pharmaceutically acceptable salt thereof.

In one embodiment, the compound of Formula II-A is:

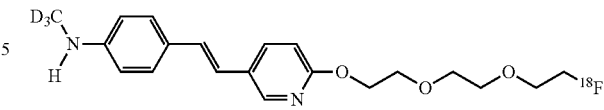

or a pharmaceutically acceptable salt thereof.

In another embodiment, the present disclosure provides a compound having Formula II-D:

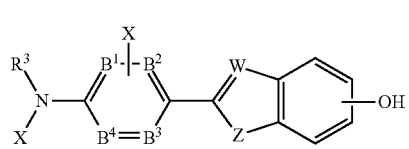

(II-D)

or a pharmaceutically acceptable salt thereof, wherein:
$R^3$ is $C_{1-4}$ alkyl, wherein $R^3$ is substituted with one or more deuterium atoms and one or more of carbon atoms of the $C_{1-4}$ alkyl are optionally $^{11}C$;
$B^1$, $B^2$, $B^3$, and $B^4$ are each independently C, N, or CH, and at most two of $B^1$, $B^2$, $B^3$, and $B^4$ are N;
X is hydrogen, $^{18}F$, or $^{19}F$;
W is N or CH; and
Z is O, S, or NH;
provided that the compound is labeled with $^{11}C$ or $^{18}F$.

One embodiment of the present disclosure provides a compound of Formula II-D wherein $R^3$ is $C_{1-4}$ alkyl that can be deuterated or non-deuterated. In some embodiments, $R^3$ is
$-CH_3$, $-CD_3$, $-CH_2CH_3$, $-CD_2CD_3$, $-CD_2CH_3$, $-CH_2CD_3$, $-CH(CH_3)_2$, $-CD(CD_3)_2$, $-CH(CD_3)_2$, $-CD(CH_3)_2$, $-CH_2CH(CH_3)_2$, $-CD_2CH(CH_3)_2$, $-CH_2CD(CH_3)_2$, $-CH_2CH(CD_3)_2$, $-CD_2CD(CH_3)_2$, $-CD_2CH(CD_3)_2$, $-CH_2CD(CD_3)_2$, or $-CD_2CD(CD_3)_2$.
In some of these embodiments, $R^3$ is $-CD_3$, $-CD_2CD_3$, $-CD_2CH_3$, $CH_2CD_3$, $-CD(CD_3)_2$, $-CH(CD_3)_2$, $-CD(CH_3)_2$, $-CD_2CH(CH_3)_2$, $-CH_2CD$ $(CH_3)_2$, $-CH_2CH(CD_3)_2$, $-CD_2CD(CH_3)_2$, $-CD_2CH$ $(CD_3)_2$, $-CH_2CD(CD_3)_2$, or $-CD_2CD(CD_3)_2$. In some embodiments, $R^3$ is $-CH_3$ or $-CD_3$. In some embodiments, $R^3$ is $-CD_3$.

In some embodiments, the present disclosure provides a compound of Formula II-D having the following formulae:

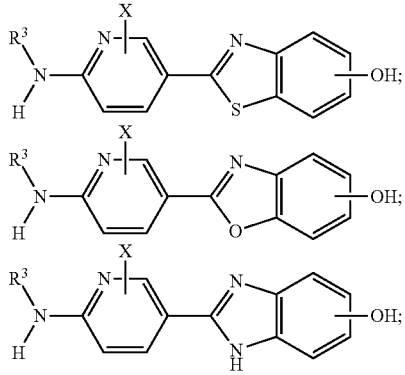

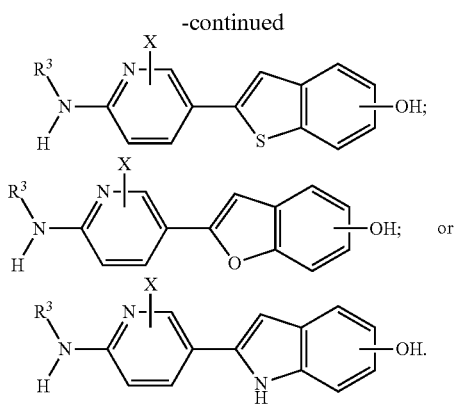

In some other embodiments, the present disclosure provides a compound of Formula II-D having the following formulae:

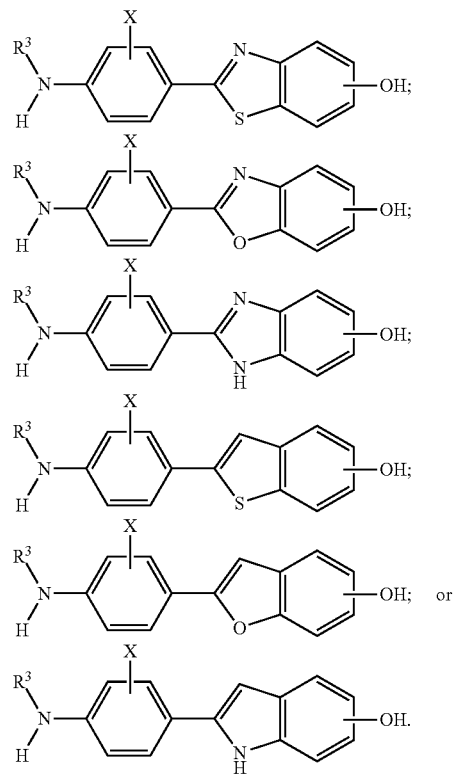

In some embodiments, the compound of Formula II-D has the following formula:

(II-E)

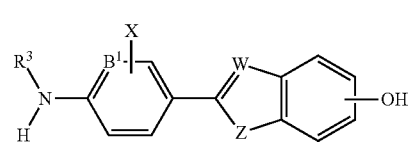

or a pharmaceutically acceptable salt thereof, wherein:
$R^3$ is $C_{1-2}$ alkyl;
$B^1$ is C, N, or CH; and
X, W, and Z are as defined herein.

In some embodiments, the present disclosure provides a compound having Formula II-D or II-E wherein $R^3$ is methyl substituted with one or more deuterium atoms. In some embodiments, $R^3$ is $CD_3$ and X is $^{18}F$.

In some embodiments, the present disclosure provides a compound having Formula II-D or II-E wherein $R^3$ is $C_{1-4}$ alkyl and one carbon atom of the $C_{1-4}$ alkyl is $^{11}C$. In some embodiments, $R^3$ is $^{11}CD_3$ and X is hydrogen.

In some embodiments, the compound of Formula II-D has the following formula:

(II-F)

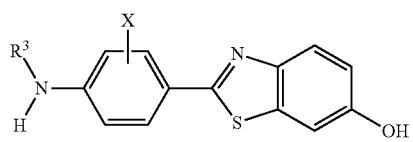

or a pharmaceutically acceptable salt thereof, wherein $R^3$ and X are as defined herein. In some embodiments, $R^3$ is —$CD_3$ and X is $^{18}F$. In some embodiments, $R^3$ is —$^{11}CD_3$ and X is H.

In some embodiments, the compound of Formula II-D has the following formula:

(II-G)

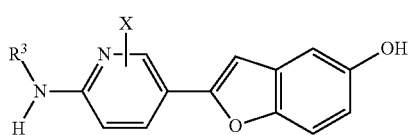

or a pharmaceutically acceptable salt thereof, wherein $R^3$ and X are as defined herein. In some embodiments, $R^3$ is —$CD_3$ and X is $^{18}F$. In some embodiments, $R^3$ is —$^{11}CD_3$ and X is H.

In one embodiment, the compound of Formula II-D is:

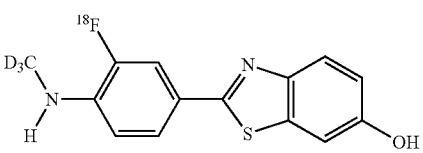 [SMILES: [2H]C([2H])([2H])Nc1ccc(-c2nc3ccc(O)cc3s2)cc1[18F]]

or a pharmaceutically acceptable salt thereof.

In one embodiment, the compound of Formula II-D is:

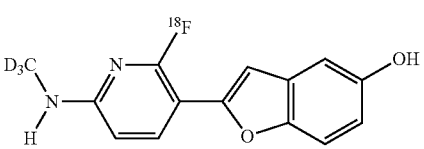 [SMILES: [2H]C([2H])([2H])Nc1ccc(-c2cc3cc(O)ccc3o2)c([18F])n1]

or a pharmaceutically acceptable salt thereof.

In one embodiment, the compound of Formula II-D is:

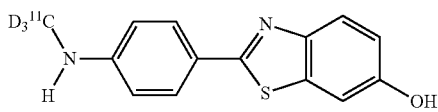

or a pharmaceutically acceptable salt thereof.

In one embodiment, the compound of Formula II-D is:

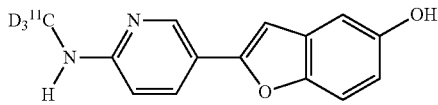

or a pharmaceutically acceptable salt thereof.

The present disclosure provides a method for diagnosing Alzheimer disease in a subject in need thereof comprising administering an effective amount of a compound of Formula II-A or a pharmaceutically acceptable salt thereof to the subject and obtaining an image of the subject or a portion of the subject. In some embodiments, the method for diagnosing Alzheimer disease comprising administering an effective amount of a compound of Formula II-A disclosed herein wherein X is $^{18}$F.

The present disclosure provides a method for diagnosing Alzheimer disease in a subject in need thereof comprising administering an effective amount of a compound of Formula II-D or a pharmaceutically acceptable salt thereof to the subject and obtaining an image of the subject or a portion of the subject. In some embodiments, the method for diagnosing Alzheimer disease comprising administering an effective amount of a compound of Formula II-D disclosed herein wherein X is $^{18}$F. In some embodiments, the method for diagnosing Alzheimer disease comprising administering an effective amount of a compound of Formula II-D disclosed herein wherein $R^3$ is $^{11}CD_3$.

Deuterated FPBM as Serotonin Transporter (SERT) Imaging Agents

Serotonin neurons in the central nervous system play an important role in normal brain function. Serotonin transporters (SERT) localized on serotonin neurons serve as the main re-uptake mechanism for terminating the action of serotonin by transporting serotonin, the neurotransmitter, from the synapse back into the presynaptic neuron. These transporters are important for controlling serotonin concentration in the synapse and its binding to the postsynaptic serotonin receptors. Selective serotonin reuptake inhibitors (SSRIs), such as Fluoxetine, Sertraline, Paroxetine, Escitalopram, specifically target SERT and prevent serotonin reuptake to the neurons. Consequently, SSRIs are useful in the treatment of depression as well as many other psychiatric conditions by controlling the concentration of serotonin in the synapse (Bousman, B M C Psychiatry 2017, 17:60). They are generally considered as the first-line therapy for depression, and they are one of the most commonly prescribed classes of drugs in the world. Positron emission tomography (PET) imaging with a suitably $^{18}$F labeled SERT inhibitor is useful as a method for probing pathophysiological and therapeutic mechanisms in various psychological diseases (Spies, Lancet Psychiatry 2015, 2:743-55). A number of SERT ligands for in vivo imaging have been developed (see structures below). $^{11}$C-McN5652 was the first SERT PET imaging tracer used in humans. Development of $^{18}$F—FMe-(+)-McN5652, an S-$^{18}$F-fluoromethyl analogue of (+)-McN5652, showed favorable features for SERT imaging with PET in humans (Hesse, J. Nucl. Med. Mol. Imaging 2012, 39:1001-11). PET imaging is also suitable for in vivo quantification of SERT.

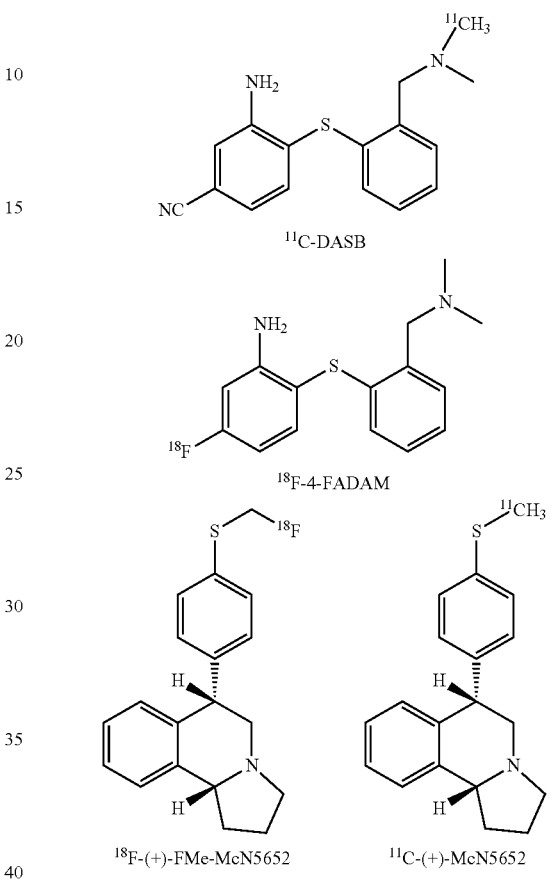

Ligands with a core structure of bisphenylthiol also showed promising results as in vivo SERT imaging agents. The most commonly used SERT PET imaging agent is $^{11}$C-DASB (Wilson, J. Med. Chem. 2000, 43:3103-10; Wilson, Nucl. Med. Biol. 2002, 29:509-15). It showed excellent selectivity, high reproducibility, and simple kinetic modeling for quantification (Kupers, Neuroimage 2011, 54:1336-43; Ginovart, Synapse 2004, 52:89-99). However, $^{11}$C-DASB is a $^{11}$C-labeled radiotracer that is limited by a short physical half-life (20 min), which is unsuitable for widespread clinical application. $^{18}$F has a longer half-life (110 min) and can be produced in several curies of activity by a cyclotron. This makes it feasible to radiolabel at a radiopharmacy and distribute the ligand regionally. Thus, an $^{18}$F-labeled SERT imaging agent may be valuable for commercial delivery via radiopharmacies. Significant efforts have been made to develop such $^{18}$F-labeled radiotracers for SERT imaging. One promising $^{18}$F-labeled ligand is $^{18}$F-4-FADAM (Huang, Eur. J. Nucl. Med. Mol. Imaging 2013, 40:115-24; Shiue, J. Nucl. Med. 2003, 44:1890-7).

Results from the first human study of $^{18}$F-4-FADAM showed that it was safe and effective for mapping SERT regional binding sites (Huang, Eur. J. Nucl. Med. Mol. Imaging 2013, 40:115-24). The regional specific uptake in the human brain correlated well with the known distribution of SERT. The optimal imaging time (about 120 min) was slightly long, but acceptable for routine clinical use. An alternative bisphenylthiol derivative, [18]F—FPBM, with a different substitution on the phenyl ring has been shown to possess high selective binding ($K_i$=0.38 nM), high brain uptake (0.99% dose/g at 2 min post iv injection), and an excellent in vivo target-to-non-target ratio (7.7 at 120 min post injection) (Wang, Nucl. Med. Biol. 2008, 35:447-58; Wang, J. Nucl. Med. 2009, 50:1509-17; Wang, Nucl. Med. Biol. 2010, 37:479-86). Previously, the labeling of this diarylsulfide was performed by a nucleophilic fluorination with K[18]F—F/K$_{2.2.2}$ via TsO-precursor (Scheme 5) (Qiao, Nucl. Med. Biol. 2016, 43:470-7; Zhu, Nucl. Med. Biol. 2013, 40:974-9). The desired product, [18]F—FPBM, was further purified by either high-performance liquid chromatography (HPLC) or solid phase extraction (SPE). During the labeling procedure it was observed that an elimination reaction led to the production of a vinyl side product.

Similar to that observed for [18]F—FP-DTBZ ([18]F-AV-133), the elimination reaction may occur by breaking the C—H bond first. Without wishing to be bound by theory, it is believed that substituting the hydrogen atoms on the propyl group with deuterium can reduce the eliminating reaction, thus improving the labeling reaction. In addition, N,N-dimethyl groups can be replaced by two deuterated methyl groups, which will resist the in vivo demethylation reaction.

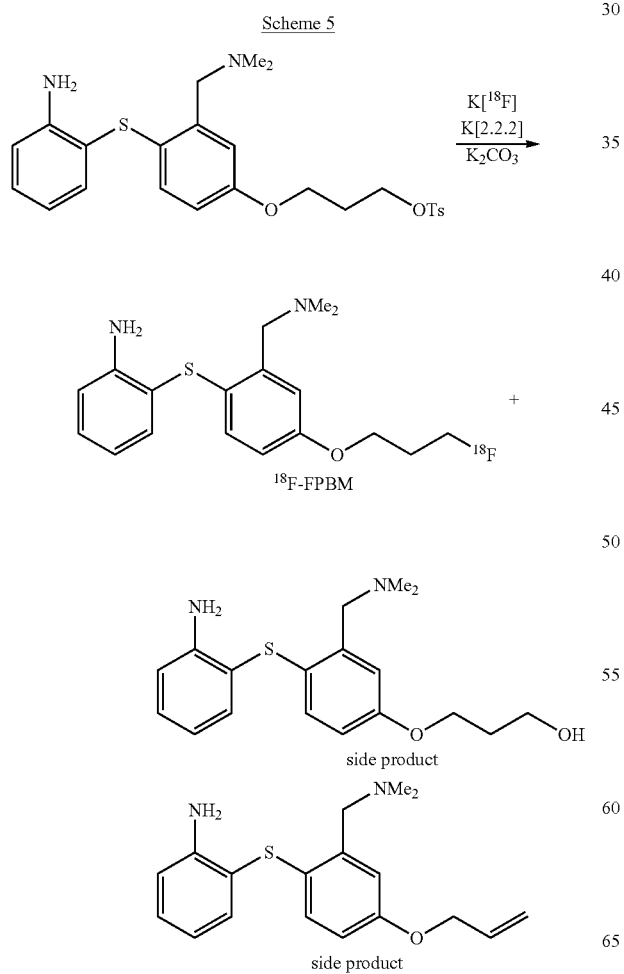

Scheme 5

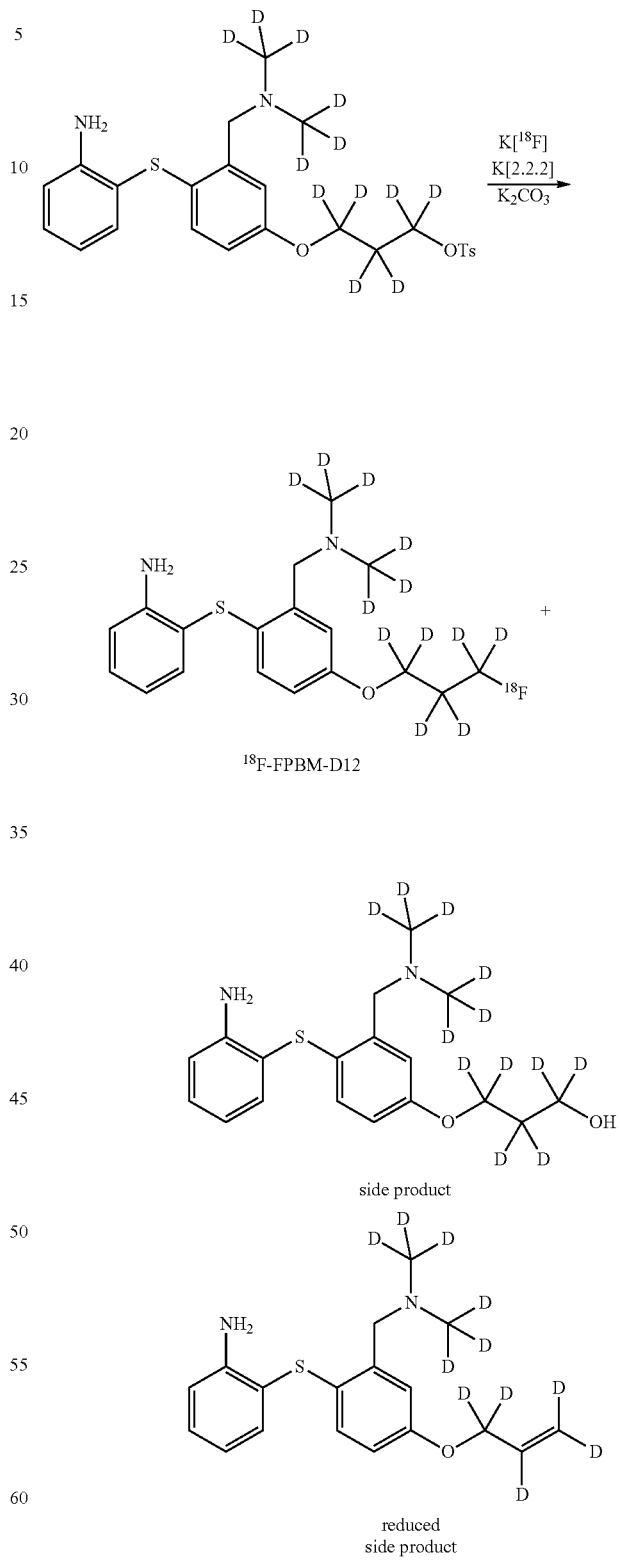

The present disclosure provides deuterium substituted diaryl sulfide compounds for PET imaging of serotonin transporters in the brain.

In one embodiment, the present disclosure provides a compound having Formula III-A:

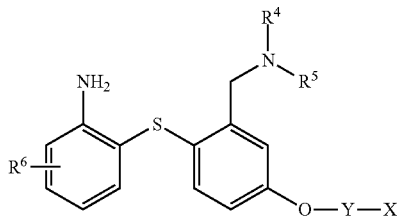

(III-A)

or a pharmaceutically acceptable salt thereof, wherein:

$R^4$ and $R^5$ are each independently hydrogen or $C_{1-4}$ alkyl, wherein the $C_{1-4}$ alkyl is optionally substituted with one or more deuterium atoms;

X is $^{18}F$ or $^{19}F$;

Y is $-(CR^aR^b)_n-$, wherein $R^a$ and $R^b$ are each independently hydrogen or deuterium atoms, and n is an integer from 1 to 6; and $R^6$ is hydrogen, halo, or CN;

provided that at least one deuterium atom is present at $R^4$, $R^5$, or Y.

One embodiment of the present disclosure provides a compound of Formula III-A wherein $R^4$ and $R^5$ are each independently hydrogen or $C_{1-4}$ alkyl that can be deuterated or non-deuterated. In some embodiments, $R^4$ and $R^5$ are each independently hydrogen, $-CH_3$, $-CD_3$, $-CH_2CH_3$, $-CD_2CD_3$, $-CD_2CH_3$, $-CH_2CD_3$, $-CH(CH_3)_2$, $-CD(CD_3)_2$, $-CH(CD_3)_2$, $-CD(CH_3)_2$, $-CH_2CH(CH_3)_2$, $-CD_2CH(CH_3)_2$, $-CH_2CD(CH_3)_2$, $-CH_2CH(CD_3)_2$, $-CD_2CD(CH_3)_2$, $-CD_2CH(CD_3)_2$, $-CH_2CD(CD_3)_2$, or $-CD_2CD(CD_3)_2$. In some of these embodiments, $R^4$ and $R^5$ are each independently hydrogen, $-CD_3$, $-CD_2CD_3$, $-CD_2CH_3$, $-CH_2CD_3$, $-CD(CD_3)_2$, $-CH(CD_3)_2$, $-CD(CH_3)_2$, $-CD_2CH(CH_3)_2$, $-CH_2CD(CH_3)_2$, $-CH_2CH(CD_3)_2$, $-CD_2CD(CH_3)_2$, $-CD_2CH(CD_3)_2$, $-CH_2CD(CD_3)_2$, or $-CD_2CD(CD_3)_2$. In some embodiments, $R^4$ and $R^5$ are each independently hydrogen, $-CH_3$, or $-CD_3$. In some embodiments, both $R^4$ and $R^5$ are $-CD_3$.

One embodiment of the present disclosure provides a compound of Formula III-A wherein n is 3, 4, 5, or 6. In some embodiments, n is 3. In some embodiments, Y is $-(CH_2)_2-$, $-(CD_2)_2-$, $-(CH_2)_3-$, $-(CD_2)_3-$, $-(CH_2)_4-$, $-(CD_2)_4-$, $-(CH_2)_5-$, $-(CD_2)_5-$, $-(CH_2)_6-$, or $-(CD_2)_6-$. In some embodiments, Y is $-(CH_2)_3-$ or $-(CD_2)_3-$.

One embodiment of the present disclosure provides a compound of Formula III-A wherein $R^6$ is hydrogen, F, Cl, Br, I, or CN. In some embodiments, $R^6$ is hydrogen. In some embodiments, $R^6$ is F, Cl, Br, or I.

In some embodiments, the compound of Formula III-A has the following formula:

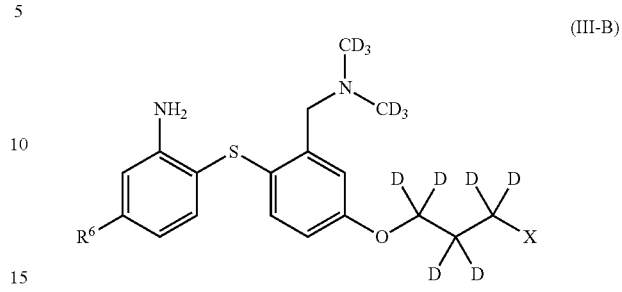

(III-B)

or a pharmaceutically acceptable salt thereof, wherein:

X is $^{18}F$ or $^{19}F$; and $R^6$ is hydrogen or halo.

In some embodiments, the compound of Formula III-A has the following formulae:

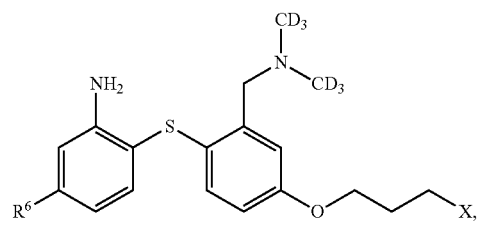

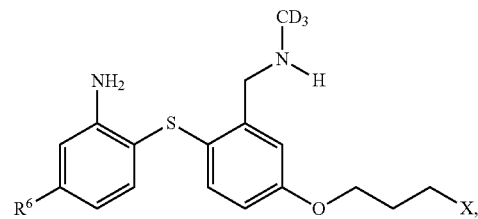

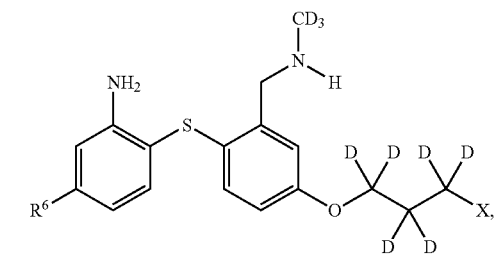

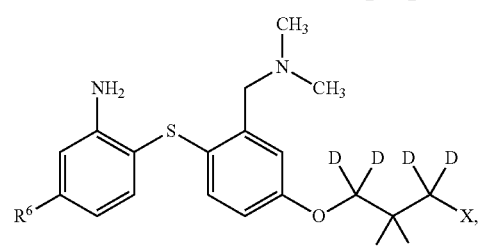

31
-continued

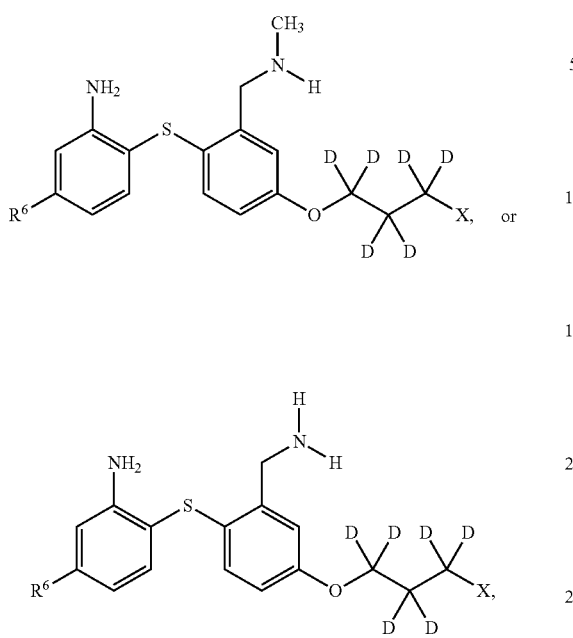

or a pharmaceutically acceptable salt thereof, wherein X and R⁶ are as defined herein.

In one embodiment, the compound of Formula III-A is

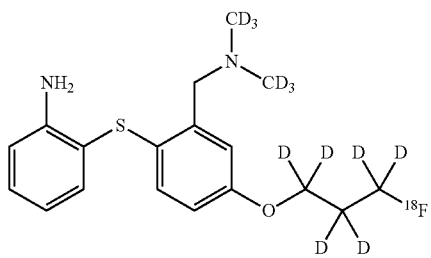 [SMILES: [2H]C([2H])([2H])N(Cc1cc(OC([2H])([2H])C([2H])([2H])C([2H])([2H])[18F])ccc1Sc1ccccc1N)C([2H])([2H])[2H]]

or a pharmaceutically acceptable salt thereof.

The present disclosure provides a method for imaging serotonin transporters in a subject in need thereof comprising administering an effective amount of a compound of Formula III-A or a pharmaceutically acceptable salt thereof to the subject and obtaining an image of the subject or a portion of the subject. In some embodiments, the method for imaging serotonin transporters comprising administering an effective amount of a compound of Formula III-A disclosed herein wherein X is $^{18}F$.

In some embodiments, the present disclosure provides a method for determining SSRI activity for treatment of depression in a subject in need thereof comprising administering an effective amount of a compound of Formula III-A disclosed herein to the subject and obtaining an image of the subject or a portion of the subject.

32
EXAMPLES

Example 1

Synthesis of Compound Ia

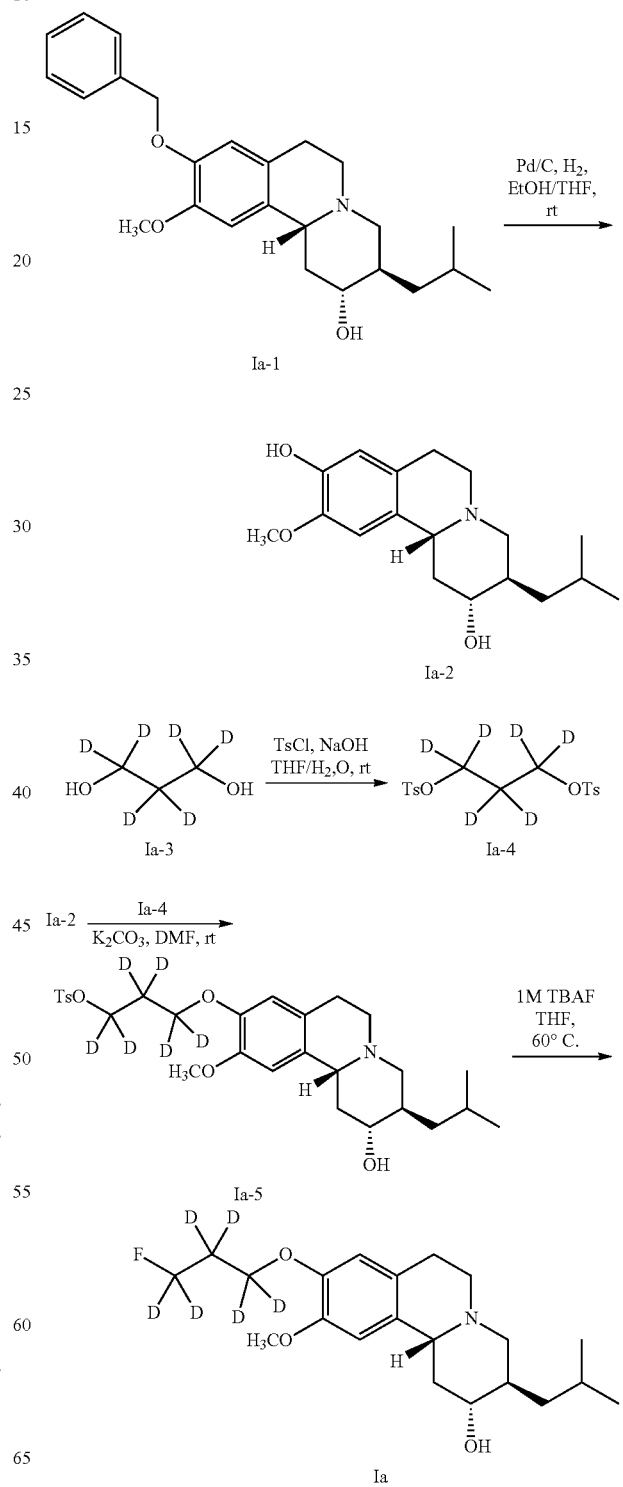

-continued

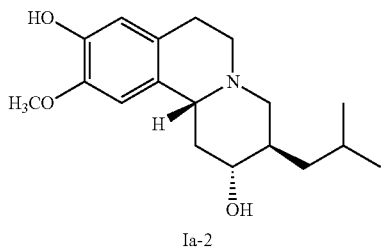

Ia-2

Synthesis of Compound Ia-2: (2R,3R,11R)-3-Isobutyl-10-methoxy-2,3,4,6,7,11b-hexahydro-1H-pyrido[2,1-a]isoquinoline-2,9-diol A mixture of 9-benzyl protected DTBZ (Ia-1, 380 mg, 0.96 mmol) and 10% dry Pd/C (15 mg) was stirred in THF (10 mL) and EtOH (5 mL) under $H_2$ at room temperature for 6 h. The reaction mixture was filtered and washed with EtOH (10 mL) and THF (10 mL). The solvent was removed under vacuum to give Ia-2 (255 mg, 87%) as a yellow solid. $^1$HNMR (400 MHz, CDCl$_3$) δ 6.68 (s, 1H), 6.67 (s, 1H), 3.87 (s, 3H), 3.44-3.38 (m, 1H), 3.16-2.97 (m, 4H), 2.66-2.56 (m, 2H), 2.49-2.42 (m, 1H), 1.99 (t, J=2.01 Hz, 1H), 1.79-1.68 (m, 2H), 1.57-1.45 (m, 3H), 1.12-1.05 (m, 1H), 0.97-0.93 (m, 6H). HRMS calcd. for $C_{18}H_{27}NO_3$ [M+H]$^+$ 306.2069. found 306.2100.

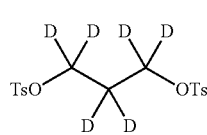

Ia-4

Synthesis of Compound Ia-4: [1,1,2,2,3,3-D6]-Propane-1,3-diylbis(4-methylbenzenesulfonate)

To a solution of compound Ia-3 (270 mg, 3.29 mmol) (99 atom % D) in THF (10 mL) was added NaOH (527 mg, 13.17 mmol) in $H_2O$ (5 mL) at 0° C. The reaction mixture was stirred at room temperature for 1 h. TsCl (1.88 g, 9.88 mmol) in THF (10 mL) was then added dropwise. The reaction was stirred at room temperature for 24 h. $H_2O$ (20 mL) was added and the mixture was extracted with ethyl acetate (3×30 mL). The organic layers were combined and dried over anhydrous MgSO$_4$, filtered and the filtrate was evaporated in vacuum, purified by flash chromatography (silica gel) (Ethyl Acetate (EA)/Hexane, 0% to 60%, vol/vol) to give [1,1,2,2,3,3-D6]-propane-1,3-diylbis(4-methylbenzenesulfonate), Ia-4, (970 mg, 76%) as a white solid. $^1$HNMR (400 MHz, CDCl$_3$) δ 7.78-7.76 (m, 4H), 7.38-7.36 (m, 4H), 2.483 (s, 6H). HRMS calcd. for $C_{17}H_{14}D_6O_6S_2$ [M+H]$^+$ 391.1156. found 391.1140.

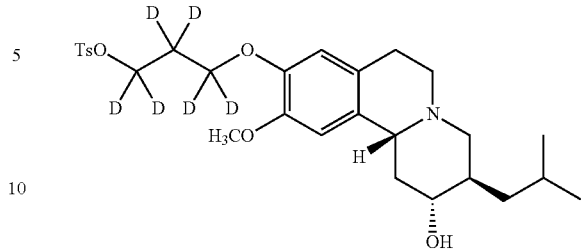

Ia-5

Synthesis of Compound Ia-5: 3-(((2R,3R,11R)-2-Hydroxy-3-isobutyl-10-methoxy-2,3,4,6,7,11b-hexahydro-1H-pyrido[2,1-a]isoquinolin-9-yl)oxy)propyl-[1,1,2,2,3,3-D6])-4-methylbenzenesulfonate A mixture of Ia-2 (44 mg, 0.14 mmol) and $K_2CO_3$ (119 mg, 0.86 mmol) was stirred in DMF (4 mL) at room temperature for 1 h. Compound Ia-4 (68 mg, 0.17 mmol) was then added and the reaction mixture was stirred for 24 h at room temperature. Water (5 mL) was added, and the mixture was extracted with ethyl acetate (5×15 mL). The organic layers were combined and dried over anhydrous MgSO$_4$, filtered and the filtrate was evaporated in vacuum, purified by flash chromatography (silica gel) (MeOH/DCM, 0% to 10%, vol/vol) to give Ia-5 (33.7 mg, 45%) as a light yellow solid. $^1$HNMR (400 MHz, CDCl$_3$) δ 7.80-7.78 (m, 2H), 7.30-7.29 (m, 2H), 6.68 (s, 1H), 6.54 (s, 1H), 3.78 (s, 3H), 3.43-3.39 (m, 1H), 3.15-2.97 (m, 4H), 2.65-2.57 (m, 2H), 2.50-2.44 (m, 1H), 2.43 (s, 3H), 2.00 (t, J=2.01 Hz, 1H), 1.78-1.68 (m, 2H), 1.64-1.47 (m, 3H), 1.12-1.05 (m, 1H), 0.98-0.94 (m, 6H). HRMS calcd. for $C_{28}H_{33}D_6NO_6S$ [M+H]$^+$ 524.2953. found 524.2963.

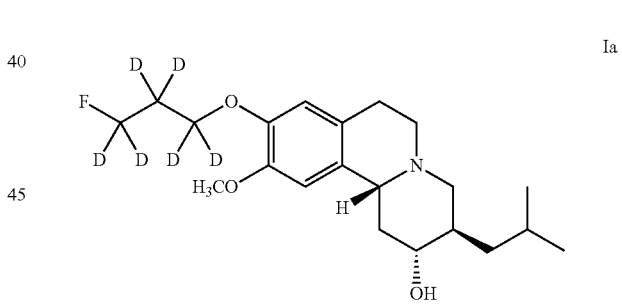

Ia

Synthesis of compound Ia: (2R,3R,11R)-9-(3-Fluoropropoxy-[1,1,2,2,3,3-D$_6$])-3-isobutyl-10-methoxy-2,3,4,6,7,11b-hexahydro-1H-pyrido[2,1-a]isoquinolin-2-ol A mixture of compound Ia-5 (30 mg, 0.06 mmol) and 1M TBAF in THF (0.17 mL, 0.17 mmol) was stirred in anhydrous THF (5 mL) at 60° C. for 5 h. $H_2O$ (5 mL) was added, and the mixture was extracted with ethyl acetate (5×10 mL). The organic layers were combined and dried over anhydrous MgSO$_4$, filtered and the filtrate was evaporated in vacuum, purified by flash chromatography (silica gel) (MeOH/DCM, 0% to 10%, vol/vol) to give Ia (11.2 mg, 26%) as a light yellow solid. $^1$HNMR (400 MHz, CDCl$_3$) δ 6.71 (s, 1H), 6.64 (s, 1H), 3.84 (s, 3H), 3.44-3.38 (m, 1H), 3.16-2.98 (m, 4H), 2.66-2.57 (m, 2H), 2.51-2.44 (m, 1H), 2.00 (t, J=2.01

Hz, 1H), 1.79-1.68 (m, 2H), 1.56-1.47 (m, 3H), 1.12-1.05 (m, 1H), 0.97-0.94 (m, 6H). HRMS calcd. for $C_{21}H_{26}D_6FNO_3$ [M+H]$^+$ 372.2821. found 372.2824.

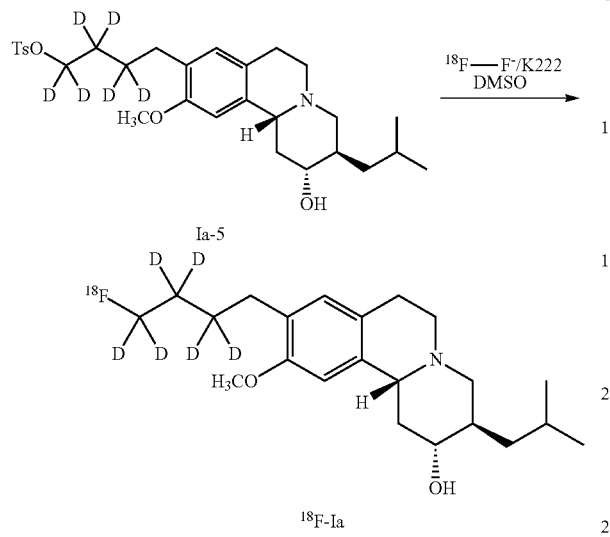

Preparation of $^{18}$F-Ia ($^{18}$F-AV-133-D6) by radiolabeling was accomplished by the following steps. $^{18}$F fluoride was loaded on an activated QMA light cartridge and eluted with 0.7 mL $K_{222}/K_2CO_3$ solution (40 mg $K_2CO_3$, 220 mg $K_{222}$, 3.6 mL water, 18.4 mL ACN) into conical vial. The solution was dried under a flow of argon at 80° C. and azeotropically dried twice with 1 mL acetonitrile. 1 mg Ia-5 was dissolved in 0.5 ml DMSO (anhydrous) and added to dried [$^{18}$F]F$^-$/$K_{222}/K_2CO_3$ complex. The reaction mixture was heated for 15 min at 115° C. The resulting reaction mixture was cooled to room temperature and added to 8 mL water. The mixture was loaded onto an Oasis HLB (3 cc) cartridge. Eluted and washed twice with 3 mL water. The desired $^{18}$F-Ia was eluted with 1 ml acetonitrile (yield: 62%, RCP ~98% HPLC (Supelco Ascentis 150×4.6 mm, ACN/10 mM ammonium format buffer (AFB) 45/55, 1 mL/min). To this solution was added about 1 mL of 10 mM AFB and injected onto prep HPLC (Phenomenex Gemini 250×10 mm, ACN/10 mM AFB 45/55, 3 mL/min). The eluent of the desired $^{18}$F-Ia was collected (660 µCi mCi, retention time 14-15 min). The solution was mixed with 18 mL water and added onto an Oasis HLB 3 cc. The activity was eluted with 1 mL 100% ethanol (590 µCi). Solution was concentrated to about 200 µL volume diluted with 1.8 mL buffer. HPLC profile on HPLC (HPLC: Supelco Ascentis 150×4.6 mm, ACN/10 mM AFB 45/55, 1 mL/min) showed single peak at 6 minutes for 18F-Ia ($^{18}$F-AV-133-D6), RCY 48% (dc): RCP: 99%; SA~182 Ci/mmol (measured at 280 nm). The retention time corresponded to cold Ia.

Example 2

In Vitro Binding Assay for Ki Determination AV-133 vs AV-133-D6 (Ia)

Tissue homogenates of striatum (dissected from rat brain) were prepared in 50 mM of HEPES, pH 7.5, and 0.3 M of sucrose. Compounds were examined for their ability to compete for the binding of $^{18}$F-AV-133 or $^{18}$F-AV-133-D6 ($^{18}$F-Ia) (0.15-0.2 nM) at concentrations ranging from $10^{-7}$ to $10^{-12}$ M. The binding assays were performed in glass tubes (12×75 mm) in a final volume of 0.25 mL. The nonspecific binding was defined with 10 µM (±)-tetrabenazine (TBZ). After incubation for 90 min at room temperature, the bound ligand was separated from the free ligand by filtration through glass fiber filters. The filters were washed three times with 4 mL of ice-cold PBS buffer, pH 7.4 and the radioactivity on the filters was counted with a gamma counter (WIZARD$^2$, Perkin-Elmer). Data were analyzed using the nonlinear least-square curve fitting program LIGAND to determine IC$_{50}$ and K$_i$ was calculated by Cheng-Prusoff equation using 0.11 nM as Kd of AV-133 and AV-133-D6 (Ia).

TABLE 1a

Comparison of in vitro binding affinity (Ki, nM) to vesicular monoamine transporter 2 (VMAT2) for (±)TBZ, AV-133, and AV-133-D6 (Ia)

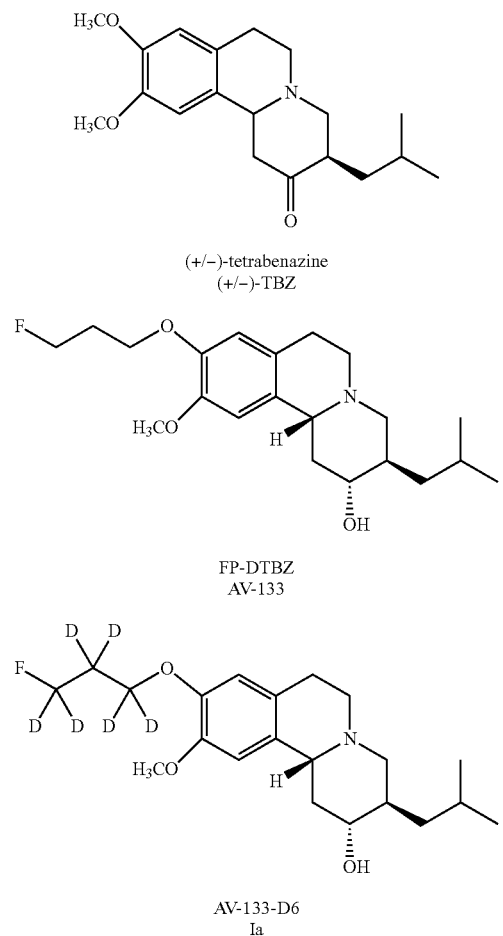

| Hot ligand | (±)TBZ | AV-133 | Ia (AV-133-D6) |
|---|---|---|---|
| $^{18}$F-AV-133-D6 | 1.65 ± 0.07 | 0.26 ± 0.03 | 0.33 ± 0.06 |
| $^{18}$F-AV-133 | 1.49 ± 0.24 | 0.33 ± 0.02 | 0.32 ± 0.07 |

Ki of cold competing drug (nM, Avg ± SD, n = 3)

The (±)TBZ showed a lower binding affinity comparable to reported in the literature. Results of binding studies for AV-133 and AV-133-D6 (Ia) showed that hydrogen to deuterium substitution provided the same binding affinity to the VMAT2 binding sites. The results showed that $^{18}$F-AV-133-D6 (Ia) is an excellent PET imaging agent for VMAT2 binding sites. Similar to the recently approved deuterated tetrabenazine SD-809, the "cold" AV-133-D6 (Ia) which shows a higher binding affinity to the target sites (VMAT2), may be a useful therapeutic agent for movement disorders.

Example 3

Comparison of FP-DTBZ Biodistribution Data in Rats

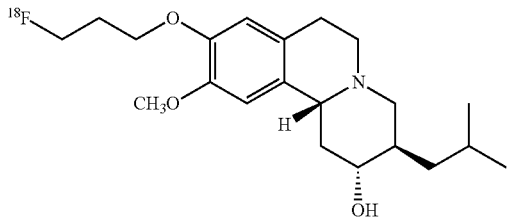

$^{18}$F-FP-DTBZ
$^{18}$F-AV133

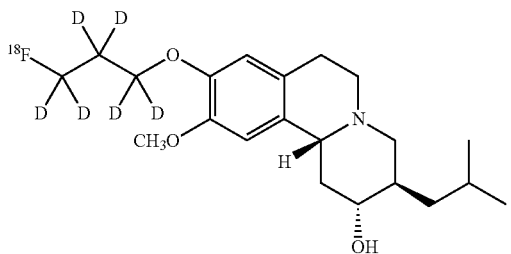

$^{18}$F-FP-DTBZ
$^{18}$F-AV-133-D6
$^{18}$F-Ia $^{18}$F-FP-DTBZ vs $^{18}$F-FP-DTBZ-D6 ($^{18}$F-Ia)

Three rats per group were used for each biodistribution study. While under isoflurane anesthesia, 0.2 mL of a saline solution containing 20 µCi of radioactive tracer was injected into the femoral vein. The rats were sacrificed at the time indicated by cardiac excision while under isoflurane anesthesia. Organs of interest were removed and weighed, and the radioactivity was counted. The percent dose per organ was calculated by comparing the tissue counts to counts of 1% of the initial dose (100 times diluted aliquots of the injected material) measured at the same time. Regional brain distribution in rats was measured after an iv injection of the radioactive tracer. Samples from different brain regions (cortex, striatum, hippocampus, cerebellum and hypothalamus) were dissected, weighed and counted. The percentage dose/g of each sample was calculated by comparing sample counts with the counts of the diluted initial dose described above. The ratio was calculated by dividing the percentage dose/g of each region by that of the cerebellum. The cerebellum was used as the reference region for calculating the ratio of target to non-target binding, because only a trace amount of VMAT2 binding site is present in the cerebellum.

TABLE 1b

Biodistribution in normal male CD rats after an IV injection of $^{18}$F-FP-(+)DTBZ (average of 3 rats ± SD)

| % dose/g | 2 min | 60 min | 120 min |
| --- | --- | --- | --- |
| Blood | 0.24 ± 0.03 | 0.12 ± 0.00 | 0.07 ± 0.01 |
| Heart | 0.96 ± 0.08 | 0.22 ± 0.03 | 0.16 ± 0.01 |
| Muscle | 0.11 ± 0.02 | 0.10 ± 0.01 | 0.07 ± 0.00 |
| Lung | 1.03 ± 0.03 | 0.41 ± 0.03 | 0.31 ± 0.02 |
| Kidney | 2.66 ± 0.15 | 0.63 ± 0.05 | 0.45 ± 0.02 |
| Spleen | 1.19 ± 0.10 | 0.50 ± 0.04 | 0.37 ± 0.05 |
| Pancreas | 2.29 ± 0.36 | 4.48 ± 0.27 | 3.56 ± 0.42 |
| Liver | 2.28 ± 0.04 | 2.59 ± 0.21 | 2.12 ± 0.20 |
| Skin | 0.19 ± 0.03 | 0.24 ± 0.03 | 0.17 ± 0.01 |
| Brain | 0.83 ± 0.06 | 0.35 ± 0.03 | 0.26 ± 0.03 |
| Bone | 0.45 ± 0.03 | 1.13 ± 0.07 | 1.86 ± 0.24 |

Regional Brain Distribution (% dose/gram ± SD) for $^{18}$F-FP-(+)DTBZ

| | 2 min | 60 min | 120 min |
| --- | --- | --- | --- |
| Cerebellum | 0.68 ± 0.06 | 0.19 ± 0.02 | 0.13 ± 0.01 |
| Striatum | 1.12 ± 0.04 | 1.04 ± 0.05 | 0.87 ± 0.12 |
| Hippocampus | 0.80 ± 0.07 | 0.30 ± 0.01 | 0.24 ± 0.03 |
| Cortex | 0.82 ± 0.07 | 0.21 ± 0.01 | 0.15 ± 0.02 |
| Remainder | 0.83 ± 0.06 | 0.31 ± 0.02 | 0.21 ± 0.02 |
| Hypothalamus | 1.06 ± 0.10 | 0.73 ± 0.11 | 0.54 ± 0.11 |

Ratio vs. Cerebellum for $^{18}$F-FP-(+)DTBZ

| | 2 min | 60 min | 120 min |
| --- | --- | --- | --- |
| Cerebellum | 1.00 ± 0.00 | 1.00 ± 0.00 | 1.00 ± 0.00 |
| Striatum | 1.66 ± 0.15 | 5.66 ± 0.72 | 6.54 ± 0.59 |
| Hippocampus | 1.19 ± 0.03 | 1.64 ± 0.19 | 1.79 ± 0.12 |
| Cortex | 1.21 ± 0.04 | 1.13 ± 0.09 | 1.11 ± 0.09 |
| Remainder | 1.23 ± 0.03 | 1.68 ± 0.07 | 1.59 ± 0.09 |
| Hypothalamus | 1.57 ± 0.04 | 3.91 ± 0.37 | 4.04 ± 0.66 |

TABLE 1c

Biodistribution in normal male CD IGS rats after an IV injection of $^{18}$F-FP-(+)DTBZ-D6 ($^{18}$F-Ia) (average of 3 rats ± SD)

| % dose/g | 2 min | 60 min | 120 min |
| --- | --- | --- | --- |
| Blood | 0.23 ± 0.03 | 0.11 ± 0.01 | 0.10 ± 0.00 |
| Heart | 0.69 ± 0.12 | 0.26 ± 0.01 | 0.21 ± 0.00 |
| Muscle | 0.17 ± 0.02 | 0.11 ± 0.00 | 0.09 ± 0.01 |
| Lung | 0.87 ± 0.05 | 0.49 ± 0.00 | 0.41 ± 0.01 |
| Kidney | 1.89 ± 0.07 | 0.66 ± 0.04 | 0.59 ± 0.02 |
| Spleen | 1.04 ± 0.10 | 0.66 ± 0.03 | 0.51 ± 0.03 |
| Pancreas | 2.62 ± 0.15 | 5.01 ± 0.69 | 4.49 ± 0.17 |
| Liver | 2.79 ± 0.12 | 3.19 ± 0.46 | 3.10 ± 0.49 |
| Skin | 0.24 ± 0.02 | 0.25 ± 0.01 | 0.21 ± 0.01 |
| Brain | 0.64 ± 0.07 | 0.44 ± 0.02 | 0.34 ± 0.02 |
| Bone | 0.33 ± 0.04 | 0.47 ± 0.02 | 0.65 ± 0.03 |

Regional Brain Distribution (% dose/gram ± SD) for $^{18}$F-FP-(+)DTBZ-D6 ($^{18}$F-Ia)

| | 2 min | 60 min | 120 min |
| --- | --- | --- | --- |
| Cerebellum | 0.48 ± 0.04 | 0.23 ± 0.01 | 0.18 ± 0.01 |
| Striatum | 1.00 ± 0.22 | 1.40 ± 0.06 | 1.00 ± 0.08 |
| Hippocampus | 0.60 ± 0.07 | 0.39 ± 0.01 | 0.31 ± 0.04 |
| Cortex | 0.65 ± 0.07 | 0.26 ± 0.01 | 0.20 ± 0.00 |
| Remainder | 0.64 ± 0.07 | 0.37 ± 0.02 | 0.28 ± 0.02 |
| Hypothalamus | 0.82 ± 0.10 | 0.91 ± 0.03 | 0.65 ± 0.11 |

Ratio vs. Cerebellum for $^{18}$F-FP-(+)DTBZ-D6 ($^{18}$F-Ia)

| | 2 min | 60 min | 120 min |
| --- | --- | --- | --- |
| Cerebellum | 1.00 ± 0.00 | 1.00 ± 0.00 | 1.00 ± 0.00 |
| Striatum | 2.08 ± 0.30 | 6.05 ± 0.43 | 5.49 ± 0.43 |
| Hippocampus | 1.26 ± 0.04 | 1.68 ± 0.12 | 1.74 ± 0.32 |

TABLE 1c-continued

| | | | |
|---|---|---|---|
| Cortex | 1.36 ± 0.05 | 1.13 ± 0.02 | 1.10 ± 0.09 |
| Remainder | 1.33 ± 0.03 | 1.59 ± 0.04 | 1.52 ± 0.03 |
| Hypothalamus | 1.71 ± 0.10 | 3.93 ± 0.15 | 3.56 ± 0.49 |

This comparison biodistribution study in rats between $^{18}$F—FP-(+)DTBZ and $^{18}$F—FP-DTBZ-D6 ($^{18}$F-Ia) demonstrated that there was good similarity. However, the most noticeable difference is the bone uptake. The deuterated $^{18}$F—FP-DTBZ-D6 ($^{18}$F-Ia) showed a clearly distinctive lowering of the bone uptake, the bone uptake at 60 and 120 min were 1.33 and 1.86% dose/g for $^{18}$F—FP-(+)DTBZ, while the deuterated $^{18}$F—FP-DTBZ-D6 ($^{18}$F-Ia) showed bone uptake of 0.47 and 0.65% dose/g, respectively. The improvement shown in lowering the bone uptake is likely associated with the higher bond energy of C-D as compared to C—H; as a consequence it reduces the level of free $^{18}$F fluoride in the blood circulation.

One other major observation is the improved brain uptake at 120 min after iv injection. The total brain uptake were 0.26 vs 0.34% dose/g for $^{18}$F—FP-(+)DTBZ and $^{18}$F—FP-DTBZ-D6 ($^{18}$F-Ia), respectively. This amounts to a 40% increase in total brain uptake. The two agents showed comparable regional brain uptake ratios; at 60 min post i.v. injection the striatum/cerebellum ratios were 5.66 vs 6.05 for $^{18}$F—FP-(+)DTBZ and $^{18}$F—FP-DTBZ-D6 ($^{18}$F-Ia), respectively.

The hydrogen to deuterium substitution presents a clear beneficial effect on improving the in vivo pharmacokinetics of the imaging agents targeting VMAT2 in the brain; as such, the novel new chemical entity with deuterium substitution provides a better specific target binding and regional brain signal for PET imaging of VMAT2 in the brain.

The hydrogen to deuterium substitution of $^{18}$F—FP-DTBZ to $^{18}$F—FP-DTBZ-D6 clearly reduced the rate of in vivo metabolism and improved the in vivo pharmacokinetics.

The novel new chemical entity with deuterium substitution provides a better specific target binding and regional brain signal for PET imaging of VMAT2 in the brain.

Example 4

Synthesis of Compounds IIa1 and $^{18}$F-IIa1

Scheme 7

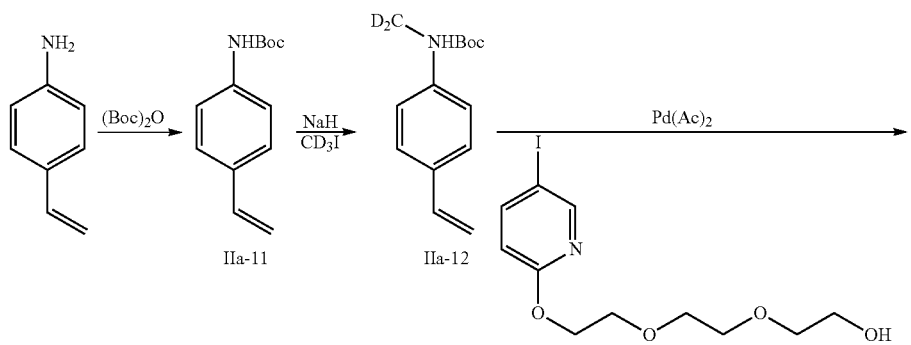

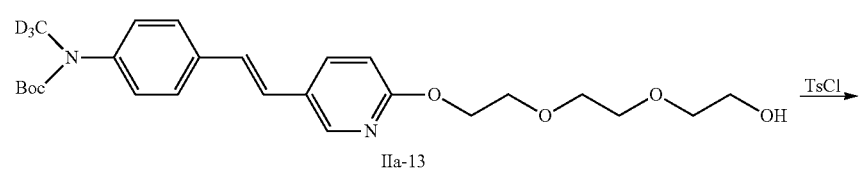

-continued
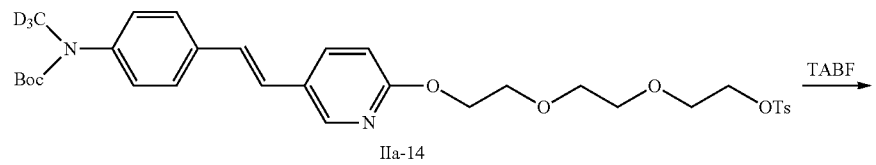
IIa-14 → TABF
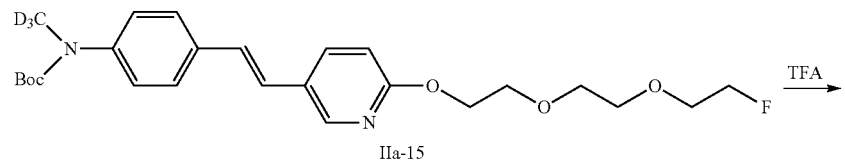
IIa-15 → TFA
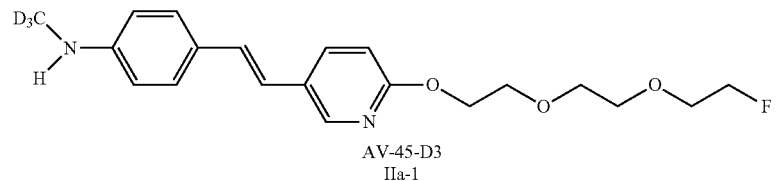
AV-45-D3
IIa-1
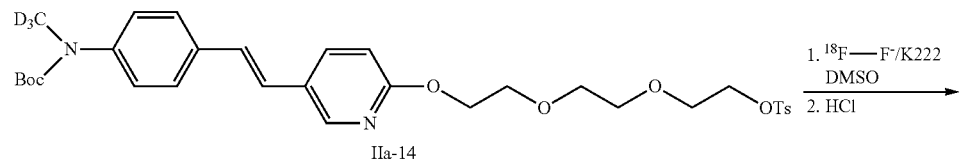
IIa-14 → 1. $^{18}$F—F$^-$/K222 DMSO 2. HCl

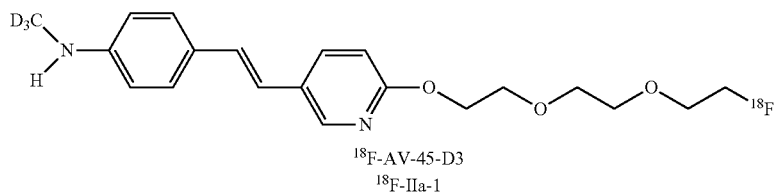

18F-AV-45-D3
18F-IIa-1

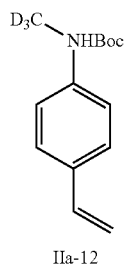

IIa-12

To a solution of p-(tert-Butoxycarbonylamino)styrene, IIa-11, (2.19 g, 10 mmol) in 15 mL of DMF, 60% NaH dispersion in mineral oil (60%, 600 mg, 15 mmol) was added slowly. After stirring at room temperature for 0.5 h, deuterated iodomethane (1.46 g, 20 mmol) (99.5 atom % D) was added. The reaction was stirred at room temperature for 2 h, and the reaction mixture was quenched with 40 mL saturated ammonium chloride ($NH_4Cl$) at 0° C. The mixture was then extracted with 60 mL of EtOAc. The organic layer was washed with $H_2O$ as well as brine (40 mL), dried by $Na_2SO_4$, and filtered. The filtrate was concentrated, and the residue was purified by flash chromatography (FC) (EtOAc/hexane=2/8) to give colorless oil, IIa-12, (2.2 g, 96.1%). $^1$HNMR (400 MHz, $CDCl_3$) δ: 7.33-7.26 (m, 2H), 7.17-7.07 (m, 2H), 6.67-6.60 (m, 1H), 5.68-5.64 (m, 1H), 5.18-5.16 (m, 1H), 1.44 (s, 9H). $^{13}$CNMR (100 MHz, $CDCl_3$) δ: 154.49, 143.28, 136.14, 129.11, 126.28, 125.55, 112.13, 28.27. HRMS calcd. for $C_{14}H_{16}D_3NO_2$ 236.1604, found 237.2107[M+H]$^+$.

A solution of IIa-12 (1 g, 4.1 mmol), 2-[2-[2-[(5-iodo-2-pyridinyl)oxy]ethoxy]ethoxy]ethanol (1.47 g, 4.1 mmol), potassium carbonate (0.69 g, 5.0 mmol), tetrabutylammonium bromide (1.29 g, 4.0 mmol), and palladium acetate (22 mg, 0.10 mmol) in 15 mL of DMF was deoxygenated by purging with nitrogen for 15 min and then heated at 65° C. for 2 h. The solution was cooled to room temperature (RT), diluted with 80 mL of ethyl acetate, and washed with brine (20 mL). The organic layer was dried by $Na_2SO_4$ and filtered. The filtrate was concentrated, and the residue was purified by FC (EtOAc/hexane=8/2) to give white solid, IIa-13, (1.27 g, 65.2%). $^1$HNMR (400 MHz, $CDCl_3$) δ: 168.04 (d, J=2.0 Hz, 1H), 7.85 (s, 1H), 7.65-7.62 (m, 1H), 7.31-7.29 (m, 2H), 7.10-7.08 (m, 2H), 6.82 (s, 2H), 6.67-6.64 (m, 1H), 4.37-4.36 (m, 2H), 3.73 (t, J=2.0 Hz, 2H), 3.59-3.55 (m, 6H), 3.49-3.47 (m, 2H), 1.34 (s, 9H). $^{13}$CNMR (100 MHz, $CDCl_3$) δ: 162.90, 162.43, 154.46, 145.50, 142.97, 135.78, 133.96, 127.16, 126.13, 126.33, 125.77, 124.30, 111.26, 80.23, 72.53, 70.53, 70.24, 69.54, 65.11, 61.45, 28.23. HRMS calcd. for $C_{25}H_{31}D_3N_2O_6$ 461.2605. Found 462.2801[M+H]$^+$.

IIa-13

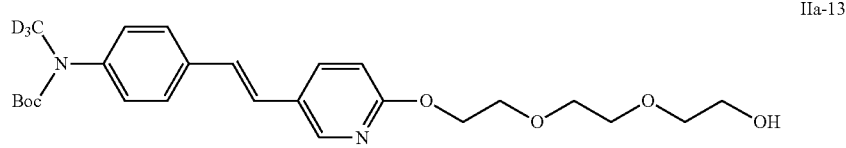 [SMILES: [2H]C([2H])([2H])N(C(=O)OC(C)(C)C)c1ccc(/C=C/c2ccc(OCCOCCOCCO)nc2)cc1]

IIa-14

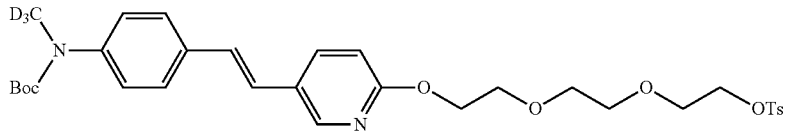

A solution of IIa-13 (1 g, 2.1 mmol) in 20 mL DCM at 0° C., 2 mL Et$_3$N, TsCl (1.64 g, 8.7 mmol) and 10 mg DMAP were added sequentially, the reaction was stirred at 0° C. for 0.5 h, then at room temperature for overnight. The solution was washed by brine (20 mL). The organic layer was dried by Na$_2$SO$_4$ and filtered. The filtrate was concentrated, and the residue was purified by FC to give light yellow oil, IIa-14, (1.24 g, 93.2%). $^1$HNMR (400 MHz, CDCl$_3$) δ: 8.04 (d, J=2.4 Hz, 1H), 7.81-7.77 (m, 3H), 7.44 (dd, J=1.6, 1.6 Hz, 2H), 7.11 (dd, J=1.6, 1.6 Hz 2H), 7.23 (d, J=8.8 Hz, 2H), 6.96 (d, J=2.4 Hz, 2H), 6.79 (d, J=8.8 Hz, 1H), 4.48-4.46 (m, 2H), 4.17-4.15 (m, 2H), 3.83-3.81 (m, 2H), 3.70-3.60 (m, 6H), 2.43 (s, 3H), 1.47 (s, 9H). $^{13}$CNMR (100 MHz, CDCl$_3$) δ: 163.05, 154.63, 145.62, 144.76, 143.14, 135.37, 134.07, 133.04, 1333.04, 129.80, 127.96, 127.32, 126.75, 126.43, 125.42, 124.44, 111.41, 80.40, 77.40, 77.08, 76.77, 70.76, 70.62, 69.75, 69.25, 68.71, 65.22, 28.34, 21.61. HRMS calcd. for C$_{32}$H$_{37}$D$_3$N$_2$O$_8$S, 615.2694. Found 616.3120[M+H]$^+$.

IIa-15

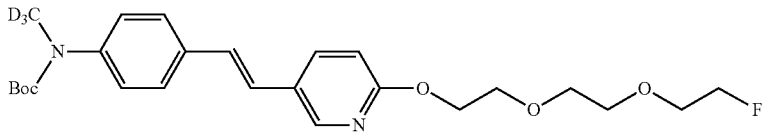

A solution of IIa-14 (0.1 g, 0.16 mmol) and tetrabutylammonium fluoride (0.25 mL, 1.0 M in THF) in 1.5 mL of THF was stirred at 70° C. for 4 h. The reaction was evaporated in vacuum, and the residue was purified by FC to give white solid, IIa-15, (64 mg, 85.4%). $^1$HNMR (400 MHz, CDCl$_3$) δ: 8.19 (d, J=2.0 Hz, 1H), 7.81-7.79 (m, 1H), 7.46-7.44 (m, 2H), 7.28-7.23 (m, 2H), 6.98 (d, J=2.0 Hz, 2H), 6.79 (d, J=8.4 Hz, 1H), 4.63 (d, J=4.0 Hz, 1H), 4.53-4.50 (m, 3H), 3.90-3.87 (m, 2H), 3.83-3.72 (m, 6H), 1.48 (s, 9H). $^{13}$CNMR (100 MHz, CDCl$_3$) δ: 163.10, 154.65, 145.64, 143.15, 135.33, 134.10, 127.30, 126.73, 126.42, 125.44, 124.49, 111.42, 83.99, 82.31, 80.42, 77.33, 77.01, 76.10, 70.85, 70.73, 70.55, 70.35, 69.79, 65.27, 28.47. HRMS calcd. for C$_{25}$H$_{30}$D$_3$FN$_2$O$_5$, 463.2562, found 464.2408[M+H]$^+$.

IIa-1

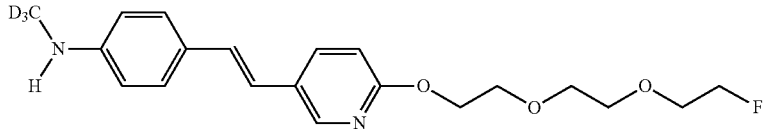

AV-45-D3

A solution of IIa-15 (30 mg, 0.06 mmol) and 1 mL TFA was stirred at room temperature for 10 min. The reaction was evaporated in vacuo, and the residue was purified by FC to give white solid, IIa-1, (19 mg, 81.5%). $^1$HNMR (400 MHz, CDCl$_3$) δ: 8.51 (s, 1H), 8.23 (d, J=2.0 Hz, 1H), 8.01 (dd, J=2.4, 2.4 Hz, 1H), 7.65 (dd, J=1.6, 1.6 Hz, 2H), 7.31 (dd, J=1.6, 1.6 Hz, 2H), 7.15 (d, J=3.2 Hz, 2H), 6.85 (d, J=8.4 Hz, 1H), 4.59 (t, J=4.0 Hz, 1H), 4.47-4.45 (m, 3H), 3.88-3.86 (m, 2H), 3.78-3.86 (m, 2H), 3.78-3.09 (m, 6H). $^{13}$CNMR (100 MHz, CDCl$_3$) δ: 162.87, 145.37, 141.13, 135.78, 135.72, 127.21, 127.04, 126.78, 124.74, 122.18, 110.84, 83.94, 81.83, 70.28, 69.79, 65.22. HRMS calcd. for C$_{20}$H$_{22}$D$_3$FN$_2$O$_3$, 363.2038; found 364.2176[M+H]$^+$.

Radiolabeling AV-45-D$_3$ ($^{18}$F-IIa-1)

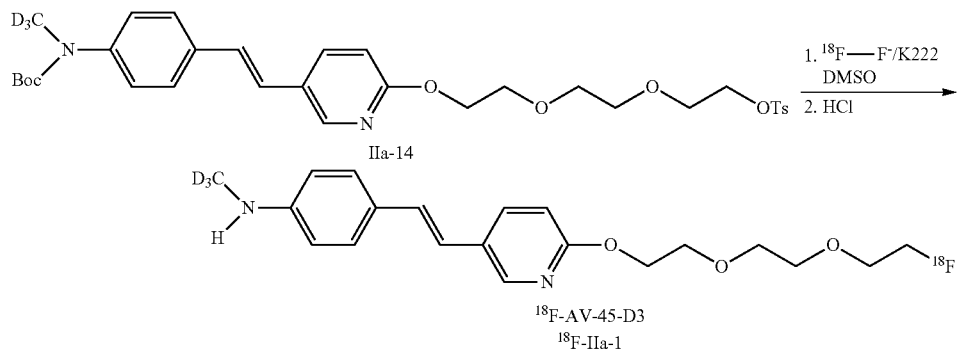

Preparation of $^{18}$F-IIa1 by radiolabeling was accomplished through the following steps, which was very similar to that reported previously (Choi, J. Nucl. Med. 2009; 50:1887-94). $^{18}$F fluoride was loaded on an activated QMA light cartridge and eluted with 0.7 mL K$_{222}$/K$_2$CO$_3$ solution (40 mg K$_2$CO$_3$, 220 mg K$_{222}$, 3.6 mL water, 18.4 mL ACN) into conical vial. The solution was dried under a flow of argon at 90° C. and azeotropically dried twice with 1 mL acetonitrile. 1 mg IIa-14 was dissolved in 0.5 ml DMSO (anhydrous) and added to dried F$^-$/K$_{222}$/K$_2$CO$_3$ complex. The reaction mixture was heated for 15 min at 110° C. The resulting reaction mixture was allowed to cool and 250 μL 10% HCl was added. The mixture was heated for 10 minutes at 100° C., then cooled in an icebath. The mixture was diluted with 8 mL water, neutralized with 850 μL 1 N NaOH and loaded onto a Oasis HLB (3 cc) cartridge. Mixture was eluted and washed twice with 3 mL water. The desired $^{18}$F-IIa1 was eluted with 1 ml acetonitrile (yield: 80%, RCP ~98% HPLC (Supelco Ascentis 150×4.6 mm, ACN/10 mM ammonium format buffer (AFB) 60/40, 1 mL/min). To this solution was added about 1 mL of 10 mM AFB and injected onto prep HPLC (Phenomenex Gemini 250×10 mm, ACN/10 mM AFB 60/40, 4 mL/min). The eluent of the desired $^{18}$F-IIa1 was collected (3.37 mCi, retention time 9-10 min). The solution was mixed with 18 mL water and added onto a Oasis HLB 3 cc. The activity was eluted with 1 mL ethanol/5 μL 10% HCl (3.03 mCi). Solution was concentrated to about 200 μL volume diluted with 1.8 mL buffer. HPLC profile on HPLC (HPLC: Supelco Ascentis 150×4.6 mm, ACN/10 mM AFB 6/4, 1 mL/min) showed single peak at 6 minutes. Dose: 3.03 mCi; RCY 71% (dc): RCP: 99%; SA ~830 Ci/mmol (measured at 350 nm). The retention time corresponded to the "cold" IIa1.

Example 5

Synthesis of Compound IIa2

Scheme 8

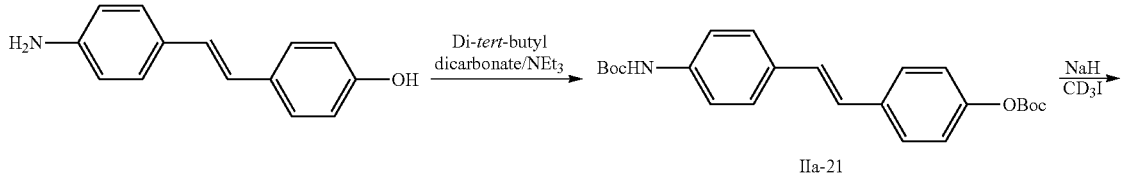

-continued
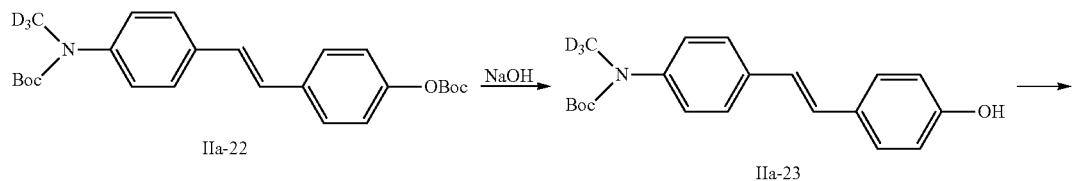
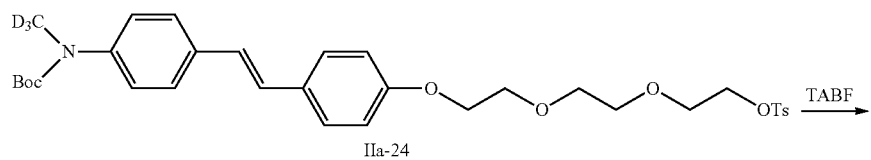
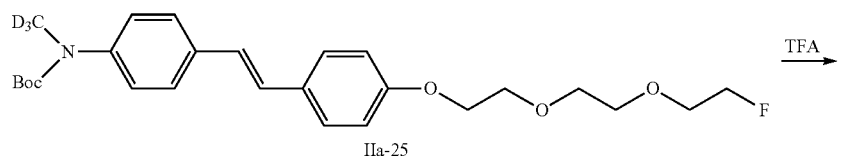
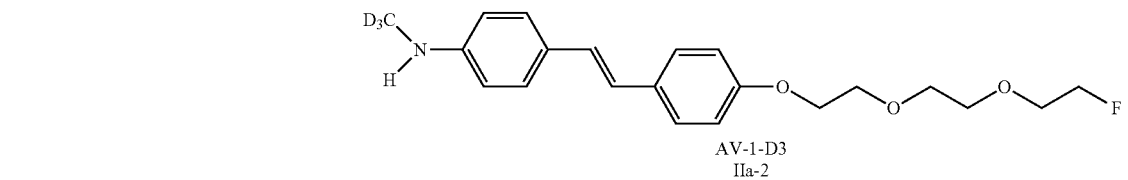
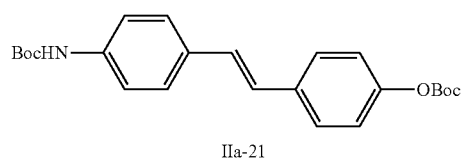
A solution of 4-stilbenol (1 g, 4.7 mmol) in 40 mL THF, then Di-tert-butyl dicarbonate (4.13 g, 18.9 mmol) and Et₃N (1.91 g, 18.9 mmol) was added. The solution was stirred at 40° C. for overnight. The reaction was evaporated in vacuo, and the residue was purified by FC to give white solid, IIa-21, (1.69 g, 86.8%) ¹HNMR (400 MHz, CDCl₃) δ:

7.49-7.46 (m, 2H), 7.43-7.41 (m, 2H), 7.37 (d, J=8.8 Hz, 2H), 7.17 (dd, J=1.6, 1.6 Hz, 1H), 6.99 (s, 1H), 6.69 (s, 1H), 1.59 (s, 9H), 1.55 (s, 9H). $^{13}$CNMR (100 MHz, CDCl$_3$) δ: 152.67, 151.85, 150.25, 137.99, 135.25, 132.01, 128.39, 127.17, 127.15, 126.21, 121.45, 118.61, 83.54, 80.57, 28.37, 27.72. HRMS calcd. for $C_{24}H_{29}NO_5$, 411.2046. Found 412.3102 [M+H]$^+$.

(d, J=8.8 Hz, 2H), 7.24 (d, J=8.4 Hz, 2H), 7.18 (d, J=8.4 Hz, 2H), 7.08 (d, J=0.8 Hz, 1H), 1.59 (s, 9H), 1.48 (s, 9H). $^{13}$CNMR (100 MHz, CDCl$_3$) δ: 151.79, 150.43, 143.20, 135.03, 134.15, 128.19, 127.40, 127.29, 126.58, 125.43, 121.47, 83.59, 80.41, 28.35, 27.21. HRMS calcd. for $C_{25}H_{28}D_3NO_5$, 428.2391. Found 429.3102 [M+H]$^+$.

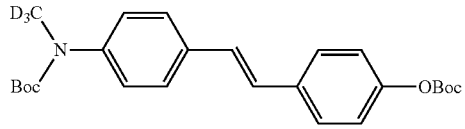

IIa-22

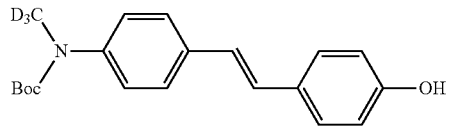

IIa-23

To a suspension of IIa-21 (1 g, 2.4 mmol) in 15 mL of DMF, 60% NaH dispersion in mineral oil (60%, 240 mg, 6 mmol) was added slowly, After stirring at room temperature for 0.5 h, deuterated iodomethane (0.73 g, 5 mmol) (≥99.5 atom % D) was added. The reaction was stirred at room temperature for 1 h, the reaction mixture was quenched with 40 mL saturated ammonium chloride (NH$_4$Cl) at 0° C. The mixture was then extracted with 60 mL of EtOAc. The organic layer was washed with water as well as brine (40 mL), dried by Na$_2$SO$_4$, and filtered. The filtrate was concentrated, and the residue was purified by FC (EtOAc/hexane=3/7) to give colorless oil, IIa-22, (1 g, 96.8%). $^1$HNMR (400 MHz, CDCl$_3$) δ: 7.51 (d, J=8.8 Hz, 2H), 7.47

To a suspension of IIa-22 (1 g, 2.3 mmol) in 15 mL of water and 20 mL methanol, NaOH (0.46 g, 11.6 mmol) was added. The reaction was stirred at room temperature for 2 h, the reaction was neutralized with 1N HCl, extracted with ethyl acetate, dried by Na$_2$SO$_4$, and filtered. The filtrate was concentrated, and the residue was purified by FC (EtOAc/hexane=3/7) to give colorless oil, IIa-23, (0.71 g, 92.5%). $^1$HNMR (400 MHz, CDCl$_3$) δ: 7.36 (d, J=8.4 Hz, 2H), 7.30 (d, J=8.4 Hz, 2H), 7.21 (d, J=8.4 Hz, 2H), 6.93 (dd, J=1.6, 1.6 Hz, 2H), 6.66 (d, J=7.6 Hz, 2H), 6.39 (s, 1H), 1.52 (s, 9H). $^{13}$CNMR (100 MHz, CDCl$_3$) δ: 155.95, 155.35, 142.28, 135.46, 126.51, 128.59, 127.74, 126.54, 125.87, 125.37, 115.72, 80.86, 28.42. HRMS calcd. for $C_{20}H_{20}D_3NO_3$, 328.1866. Found 329.1902 [M+H]$^+$.

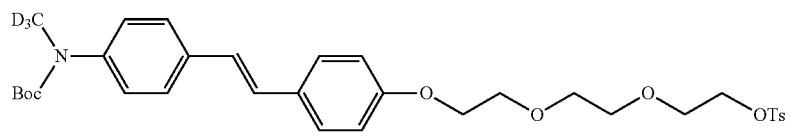

IIa-24

To a suspension of IIa-23 (0.7 g, 2.1 mmol) in 15 mL DMF, triethylene glycol di-p-toluenesulfonate (1.95 g, 4.2 mmol) was added, the reaction stirred at room temperature for overnight. The reaction was washed by brine, extracted by ethyl acetate, then dried by Na$_2$SO$_4$ and filtered. The filtrate was concentrated, and the residue was purified by FC (EtOAc/hexane=3/7) to give colorless oil, IIa-24, (1.18 g, 90.2%). $^1$HNMR (400 MHz, CDCl$_3$) δ: 7.76-7.73 (m, 2H), 7.41-7.37 (m, 4H), 7.27 (dd, J=6.8, 6.8 Hz, 2H), 7.18 (d, J=8.4 Hz, 2H), 6.95-6.92 (m, 2H), 6.88-6.84 (m, 2H), 4.12 (t, J=4.8 Hz, 2H), 4.06 (t, J=4.8 Hz, 2H), 3.76 (t, J=4.8 Hz, 2H), 3.64-3.59 (m, 4H), 3.56-3.52 (m, 2H), 2.35 (s, 3H), 1.44 (s, 9H). $^{13}$CNMR (100 MHz, CDCl$_3$) δ: 158.40, 154.60, 144.79, 144.72, 134.57, 133.00, 130.21, 129.85, 127.92, 127.88, 127.65, 126.30, 125.89, 125.35, 114.84, 80.24, 70.68, 70.55, 69.69, 69.34, 69.30, 68.64, 67.44, 28.33, 21.55. HRMS calcd. for $C_{33}H_{38}D_3NO_8S$, 614.2741. Found 615.2736 [M+H]$^+$.

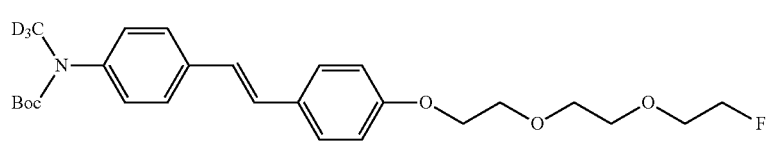

IIa-25

A solution of IIa-24 (0.1 g, 0.16 mmol) and tetrabutylammonium fluoride (0.25 mL, 1.0 M in THF) in 1.5 mL of THF was stirred at 70° C. for 4 h. The reaction was evaporated in vacuo, and the residue was purified by FC to give white solid, IIa-25, (63 mg, 84.4%) $^1$HNMR (400 MHz, CDCl$_3$) δ: 7.45 (dd, J=1.2, 1.2 Hz, 4H), 7.23 (d, J=8.4 Hz, 2H), 7.01-6.91 (m, 4H), 4.65-4.63 (m, 1H), 4.53-4.51 (m, 1H), 4.17 (t, J=4.4 Hz, 2H), 3.89 (t, J=4.4 Hz, 2H), 3.81-3.73 (m, 4H), 1.48 (s, 9H). $^{13}$CNMR (100 MHz, CDCl$_3$) δ: 158.51, 142.78, 134.68, 130.33, 127.98, 126.32, 126.00, 125.44, 114.87, 83.98, 82.30, 80.34, 70.90, 70.85, 70.56, 70.37, 69.82, 67.52. HRMS calcd. for C$_{26}$H$_{31}$D$_3$FNO$_5$, 462.2609. Found 407.2122 [M+H-tBu]$^+$.

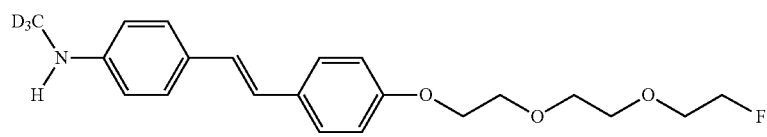

AV-1-D3

A solution of IIa-25 (40 mg, 0.08 mmol) and 1 mL TFA was stirred at room temperature for 10 min. The reaction was evaporated in vacuo, and the residue was purified by FC to give white solid, IIa-2, (29 mg, 92.3%). $^1$HNMR (400 MHz, CDCl$_3$) δ: 7.41 (d, J=8.4 Hz, 2H), 7.36 (d, J=8.4 Hz, 2H), 6.90 (dd, J=5.6, 4.8 Hz, 4H), 6.61 (d, J=8.4 Hz, 2H), 4.65-4.63 (m, 1H), 4.53-4.51 (m, 1H), 4.17 (t, J=4.8 Hz, 2H), 3.90-3.88 (MHz, 2H), 3.82-3.73 (m, 6H). $^{13}$CNMR (100 MHz, CDCl$_3$) δ: 157.86, 148.77, 131.20, 127.43, 127.10, 127.05, 126.99, 124.00, 114.82, 124.00, 114.82, 112.47, 83.99, 82.31, 70.98, 70.56, 70.30, 69.85, 67.51. HRMS calcd. for C$_{21}$H$_{23}$D$_3$FNO$_3$, 362.2085. Found 363.2402 [M+H]$^+$.

Example 6

Synthesis of Compound IIb

Compound IIb can be prepared by the synthetic method depicted in Scheme 9.

Scheme 9

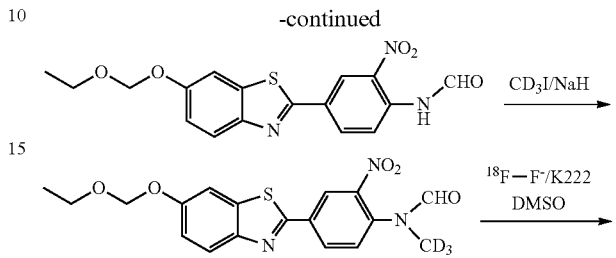

example IIa2

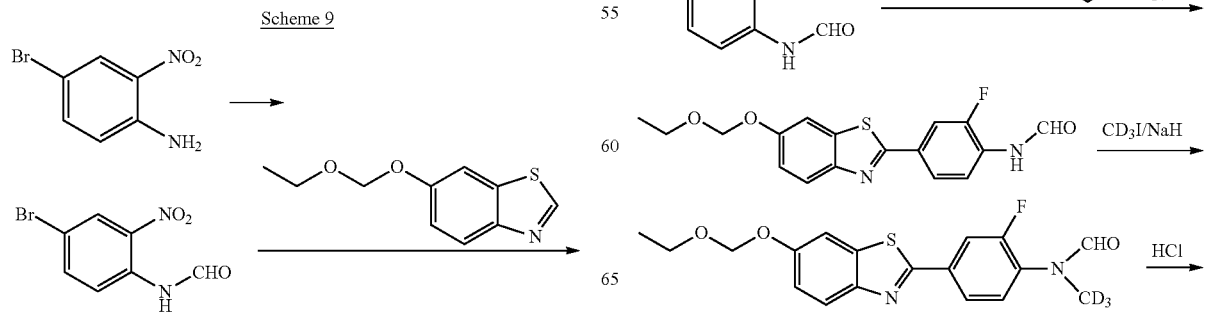

$^{18}$F-Flutemetamol-D3 ($^{18}$F-IIb)

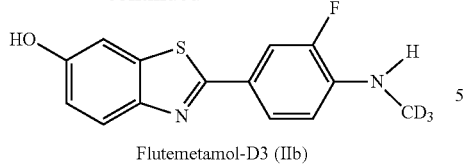

Flutemetamol-D3 (IIb)

Example 7

Synthesis of Compound ¹¹C—PIB-D3

Compound ¹¹C—PIB-D3 can be prepared by the synthetic method depicted in Scheme 10.

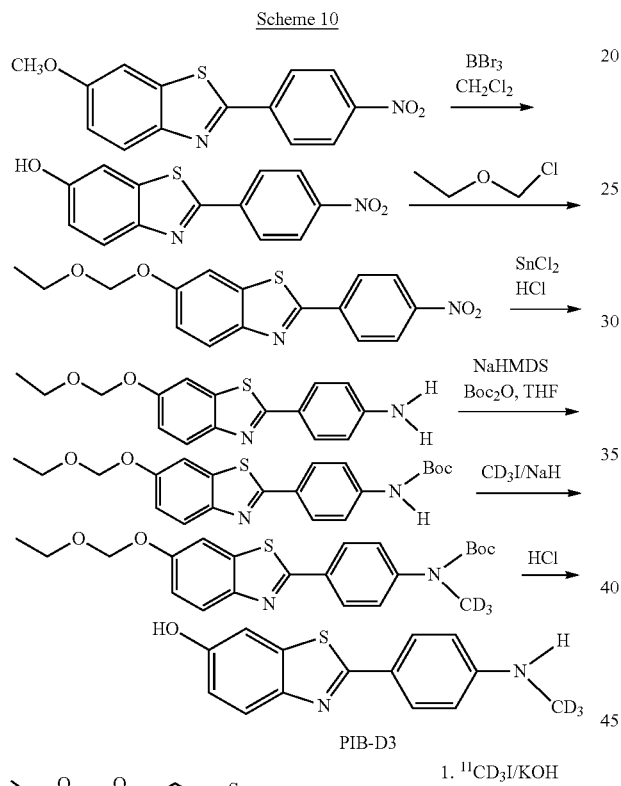

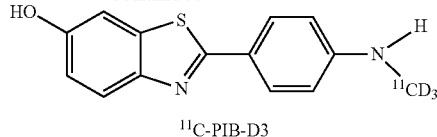

¹¹C-PIB-D3

Example 8

Synthesis of Compound IIc

Compound IIc can be prepared by the synthetic method depicted in Scheme 11.

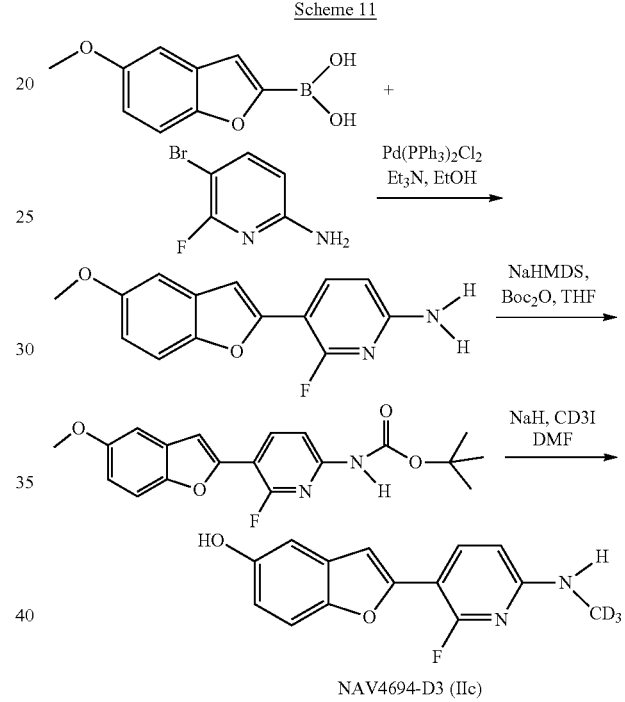

NAV4694-D3 (IIc)

Example 9

Synthesis of Compound ¹⁸F-II

Compound ¹⁸F-IIc can be prepared by the synthetic method depicted in Scheme 12.

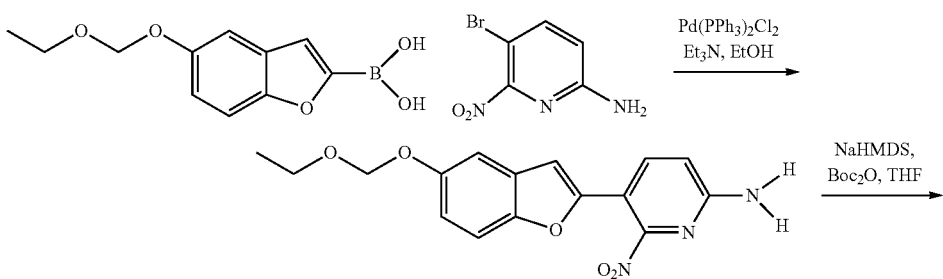

-continued

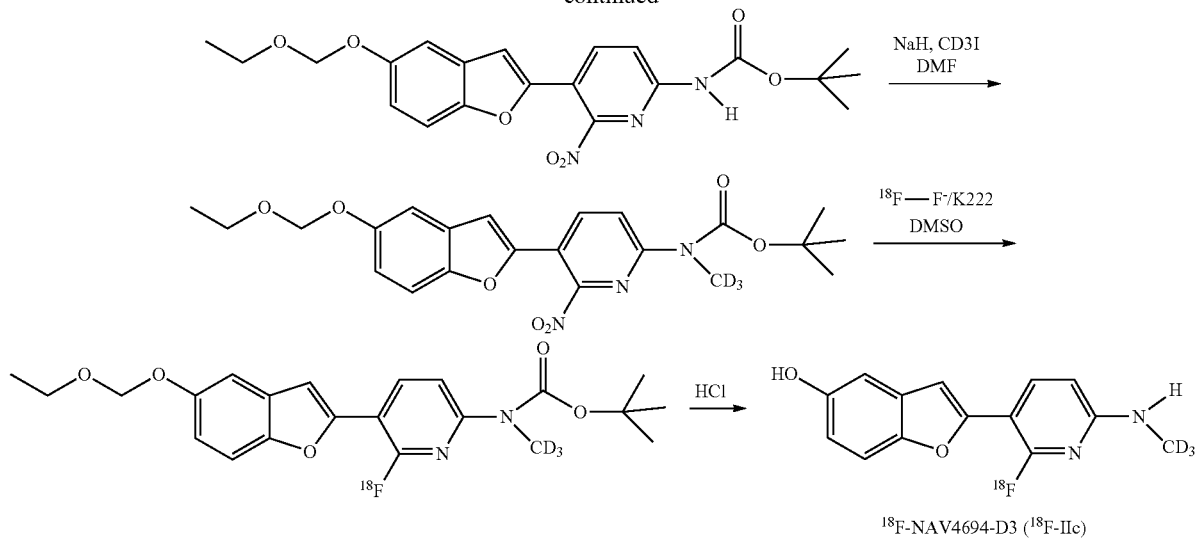

$^{18}$F-NAV4694-D3 ($^{18}$F-IIc)

Example 10

In Vitro Binding Assays for Aβ Aggregates of Human AD Brain Homogenates

Competitive binding assays were performed in 12×75 mm borosilicate glass tubes. The reaction mixture contained 100 μL of AD brain homogenates (20-25 ug), 100 μL of [$^{18}$F]AV-45 or [$^{18}$F]AV-45-D3 (~150,000 cpm), and 100 μL of competing compounds (10$^{-5}$ to 10$^{-10}$ M diluted serially in PBS containing 0.1% bovine serum albumin) in a final volume of 0.25 mL. Nonspecific binding was defined in the presence of 1 μM of IMPY (6-iodo-2-(4'-dimethylamino-)phenyl-imidazo[1,2-a]pyridine) in the same assay tubes. The mixture was incubated for 60 min at room temperature, and the bound and the free radioactivity were separated by vacuum filtration through Whatman GF/B filters using a Brandel M-24R cell harvester, followed by washing with PBS buffer three times. The radioactivity on the filters was counted with a gamma counter (Wizard², Perkin-Elmer). Data were analyzed using the nonlinear least-square curve fitting program LIGAND to determine IC$_{50}$. Ki was calculated by Cheng-Prusoff equation using 3.51 nM as Kd of AV-45 and AV-45-D3.

TABLE 2a

In vitro binding affinity for Aβ aggregates of human AD brain homogenates (Ki, nM) using a method described previously (Choi, 2009).

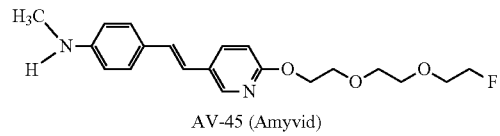 [SMILES: CNc1ccc(/C=C/c2ccc(OCCOCCOCCF)nc2)cc1]
AV-45 (Amyvid)

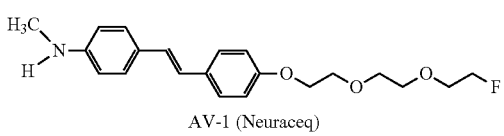 [SMILES: CNc1ccc(/C=C/c2ccc(OCCOCCOCCF)cc2)cc1]
AV-1 (Neuraceq)

TABLE 2a-continued

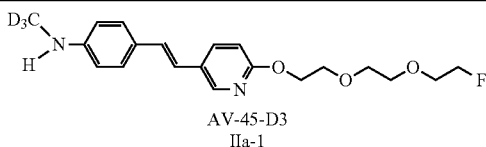
AV-45-D3
IIa-1

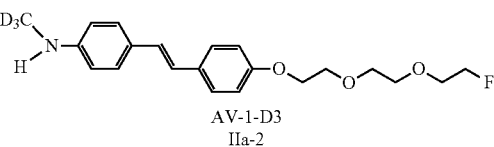 [SMILES: [2H]C([2H])([2H])Nc1ccc(/C=C/c2ccc(OCCOCCOCCF)cc2)cc1]
AV-1-D3
IIa-2

| Hot ligand | Ki of cold competing drug (nM, Avg ± SD, n = 3) | | |
|---|---|---|---|
| | AV-45-D3, IIa1 | AV-45 | AV-1-D3, IIa2 |
| $^{18}$F-AV-45-D3 | 3.25 ± 0.82 | 3.24 ± 0.76 | 4.15 ± 0.75 |
| $^{18}$F-AV-45 | 3.44 ± 1.22 | 4.02 ± 0.22 | 3.35 ± 0.88 |

Results of binding studies using either $^{18}$F-AV-45-D3 or $^{18}$F-AV-45 as the "hot ligand" showed that hydrogen to deuterium substitution (AV-45 vs AV-45-D3, AV-1-D3) exhibited the same excellent binding affinity to Aβ aggregates binding sites. All deuterated agents, AV-45-D3 (IIa1), AV-1-D3 (IIa2), displayed the same binding affinity.

Example 11

Biodistribution Study in Mice

Three mice per group were used for biodistribution study. While under isoflurane anesthesia, 0.1 mL of a saline solution containing radioactive tracer was injected into tail vein. The mice were sacrificed at the time indicated by cardiac excision while under isoflurane anesthesia. Organs of interest were removed and weighed, and the radioactivity was counted. The percent dose per organ was calculated by comparing the tissue counts to counts of 1% of the initial dose (100 times diluted aliquots of the injected material) measured at the same time.

TABLE 2b

Biodistribution of $^{18}$F-AV-45-D3 (IIa1) in normal male mice. % Dose/g (Avg ± SD of n = 3)

|          | 2 min         | 30 min        | 60 min        | 120 min       |
|----------|---------------|---------------|---------------|---------------|
| Blood    | 2.16 ± 0.05   | 2.93 ± 0.27   | 2.08 ± 0.07   | 1.36 ± 0.12   |
| Heart    | 5.08 ± 0.39   | 2.40 ± 0.39   | 1.72 ± 0.19   | 1.18 ± 0.03   |
| Muscle   | 3.21 ± 0.14   | 1.79 ± 0.06   | 1.20 ± 0.04   | 0.75 ± 0.07   |
| Lung     | 4.88 ± 0.16   | 2.90 ± 0.47   | 1.97 ± 0.25   | 1.31 ± 0.03   |
| Kidney   | 9.51 ± 0.80   | 6.41 ± 1.86   | 3.74 ± 0.47   | 2.09 ± 0.02   |
| Spleen   | 2.50 ± 0.12   | 1.52 ± 0.21   | 1.22 ± 0.12   | 0.83 ± 0.07   |
| Pancreas | 4.94 ± 0.77   | 2.05 ± 0.29   | 1.43 ± 0.20   | 0.87 ± 0.15   |
| Liver    | 12.0 ± 0.70   | 12.0 ± 0.71   | 8.15 ± 0.75   | 5.47 ± 0.29   |
| Skin     | 1.24 ± 0.27   | 2.07 ± 0.14   | 1.34 ± 0.07   | 0.91 ± 0.13   |
| Bone     | 1.74 ± 0.18   | 2.24 ± 0.44   | 2.76 ± 0.37   | 4.41 ± 0.77   |
| Brain    | 6.26 ± 0.23   | 1.71 ± 0.37   | 1.53 ± 0.20   | 1.26 ± 0.04   |

TABLE 2c

Biodistribution of $^{18}$F-AV-45 in normal male mice % Dose/g (Avg ± SD of n = 3) reported previously (Choi, 2009).

|        | 2 min        | 60 min       | 120 min      | 180 min      |
|--------|--------------|--------------|--------------|--------------|
| Blood  | 2.51 ± 0.31  | 2.37 ± 0.27  | 1.96 ± 0.23  | 1.39 ± 0.13  |
| Muscle | 3.49 ± 0.33  | 1.33 ± 0.08  | 1.02 ± 0.07  | 0.78 ± 0.09  |
| Liver  | 16.3 ± 5.38  | 11.1 ± 1.83  | 8.96 ± 0.28  | 5.39 ± 0.31  |
| Bone   | 1.33 ± 0.24  | 3.66 ± 0.30  | 6.48 ± 0.34  | 7.83 ± 1.08  |
| Brain  | 7.33 ± 1.54  | 1.88 ± 0.14  | 1.80 ± 0.20  | 1.48 ± 0.15  |

Within statistical errors the biodistribution of $^{18}$F-AV-45 and $^{18}$F-AV-45-D3 ($^{18}$F-IIa1) in mice showed very similar results. Both the deuterated and none deuterated AV-45 showed comparable brain initial penetration at 2 min after an iv injection, although with a lower brain retention at later time points, 60 and 120 min.

Example 12

Synthesis of Compound FPBM (III-1)

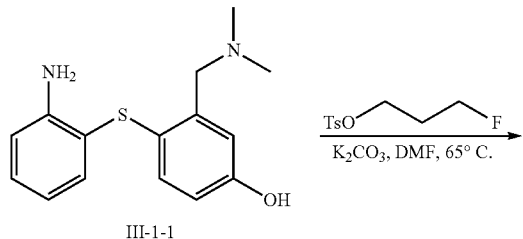

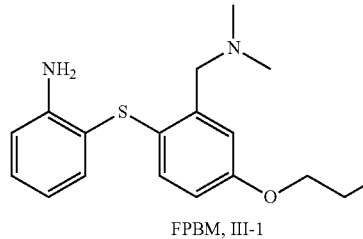

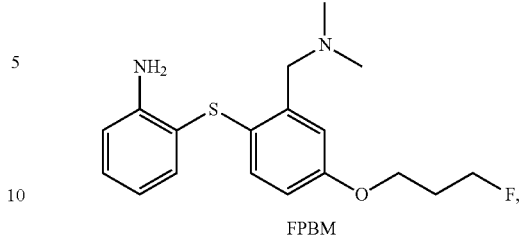

A mixture of compound III-1-1 (50 mg, 0.18 mmol) and K$_2$CO$_3$ (76 mg, 0.55 mmol) was stirred in anhydrous DMF (3 mL) at 65° C. for 1.5 hours. Then 3-fluoropropyl-4-methylbenzenesulfonate (64 mg, 0.27 mmol) was added. The mixture was stirred for another 2 hours, cooled to room temperature and saturated solution of NaCl (12 mL) was added. The mixture was extracted with EA (15 mL×3). The organic layers were combined and dried over MgSO$_4$ and filtered. The filtrate was dried under vacuum, purified by flash chromatography (silica gel) (MeOH/DCM, 0% to 10%, vol/vol) to get product FPBM, III-1 (38 mg, yield 62%) as a colorless waxy material. $^1$H NMR (400 MHz, Acetone) δ 7.33 (dd, J=7.7, 1.5 Hz, 1H), 7.15-7.09 (m, 1H), 6.98 (t, J=5.1 Hz, 2H), 6.79-6.74 (m, 2H), 6.63-6.59 (m, 2H), 5.26 (s, 2H), 4.69 (t, J=5.9 Hz, 1H), 4.57 (t, J=5.9 Hz, 1H), 4.09 (t, J=6.2 Hz, 2H), 3.55 (s, 2H), 2.26 (s, 6H), 2.21-2.06 (m, 2H). $^{13}$C NMR (100 MHz, Acetone) δ 157.53, 149.70, 139.69, 136.17, 131.11, 130.00, 127.37, 116.71, 116.25, 116.04, 114.80, 113.90, 81.36, 79.75, 63.63, 63.57, 61.88, 44.53. HRMS calcd. for C$_{18}$H$_{23}$FN$_{20}$S [M+H]$^+$ 335.1593. Found 335.1603.

Example 13

Synthesis of Compound FPBM-D6 (III-2)

Scheme 13

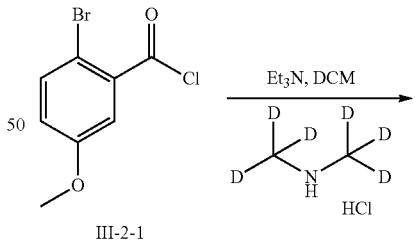

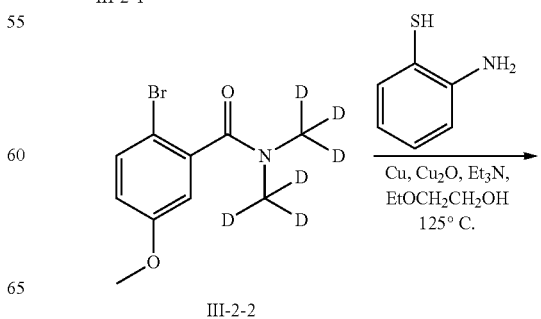

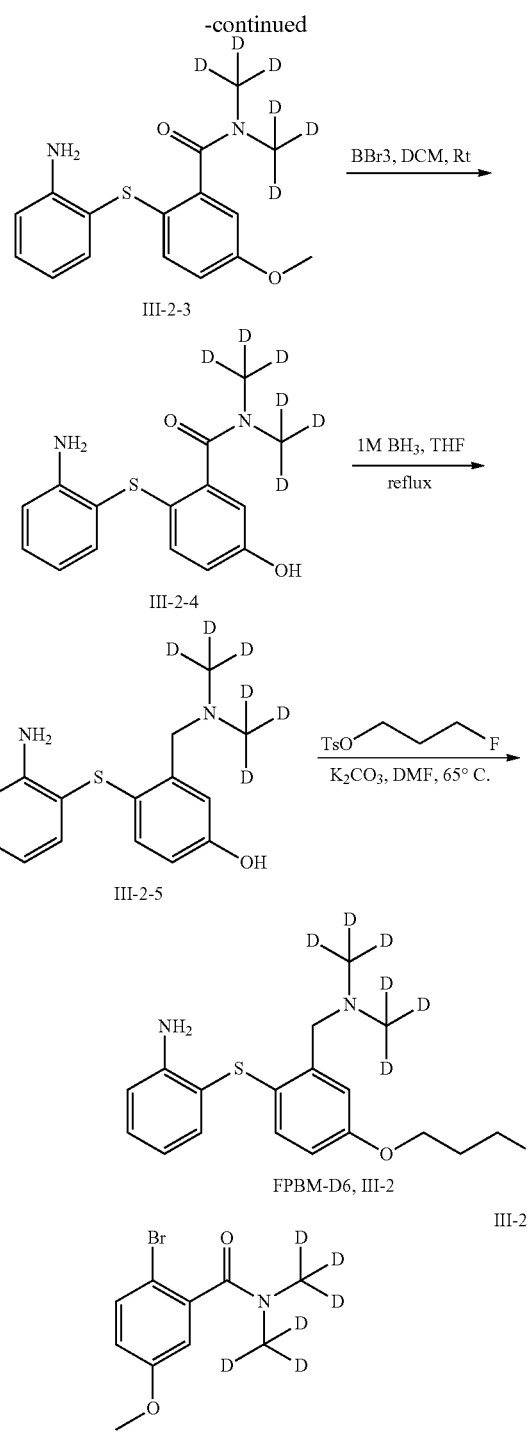

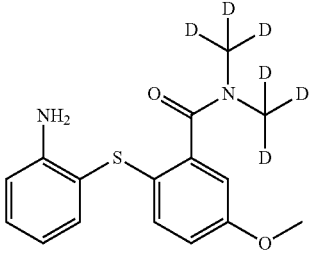

CDCl₃) δ 7.45 (d, J=8.3 Hz, 1H), 6.83-6.79 (m, 2H), 3.81 (s, 3H). ¹³C NMR (100 MHz, CDCl₃) δ 159.16, 139.29, 133.52, 116.55, 112.87, 109.38, 55.59. HRMS calcd. for $C_{10}H_6D_6BrNO_2$ [M+H]⁺264.0506. Found 264.0529.

A mixture of compound III-2-2 (510 mg, 1.94 mmol), Cu (25 mg, 0.39 mmol), Cu₂O (27 mg, 0.19 mmol), 2-aminothiophenol (364 mg, 2.91 mmol) and Et₃N (1.96 g, 19.40 mmol) was stirred in 2-ethoxyethanol (8 mL) at 125° C. for 40 hours. The mixture was then filtered and washed with methanol (20 mL) and DCM (20 mL). The filtrate was evaporated in vacuum, purified by flash chromatography (silica gel) (EA/Hexane, 0% to 60%, vol/vol) to get product III-2-3 (370 mg, yield 62%) as a colorless stick oil. ¹H NMR (400 MHz, CDCl₃) δ 7.46 (d, J=7.6 Hz, 1H), 7.21-7.09 (m, 2H), 6.84-6.66 (m, 4H), 3.78 (s, 3H). ¹³C NMR (100 MHz, CDCl₃) δ 158.71, 148.65, 138.91, 136.72, 132.33, 130.62, 123.43, 118.02, 115.94, 115.80, 115.37, 111.54, 55.47. HRMS calcd. for $C_{16}H_{12}D_6N_2O_2S$ [M+H]⁺ 309.1544. Found 309.1640.

A mixture of dimethyl-d6-amine hydrochloride (0.53 g, 6.50 mmol) (99 atom % D) and Et₃N (1.32 g, 12.99 mmol) was stirred in anhydrous DCM (20 mL) at 0° C. Then compound III-2-1 (1.08 g, 4.33 mmol) in anhydrous DCM (15 mL) was added dropwise. After addition the reaction was stirred at room temperature for 5 hours. Then water (30 mL) was added and extracted with DCM (20 mL×2). The organic layers were combined and dried over anhydrous MgSO₄, filtered and the filtrate was evaporated in vacuum, purified by flash chromatography (silica gel) (EA/Hexane, 0% to 60%, vol/vol) to get product III-2-2 (0.95 g, yield 83%) as a colorless waxy material. ¹H NMR (400 MHz, A solution of compound III-2-3 (300 mg, 0.97 mmol) was stirred in anhydrous DCM (15 mL) at 0° C., Then 1M BBr₃ in DCM (2.92 mL, 2.92 mmol) was added drop wise under N₂. After complete addition the reaction mixture was stirred at room temperature. A saturated solution of NaHCO₃ was added and extracted with DCM (20 mL×2). The organic layers were combined and dried over anhydrous MgSO₄, filtered and the filtrate was evaporated in vacuum and purified by flash chromatography (silica gel) (EA/Hexane, 0% to 80%, vol/vol) to get product III-2-4 (200 mg, yield 70%) as a colorless stick oil. ¹H NMR (400 MHz, CDCl₃) δ 7.40 (dd, J=7.6, 1.5 Hz, 1H), 7.18-7.14 (m, 1H), 6.89 (d, J=8.6 Hz, 1H), 6.73-6.54 (m, 4H), 4.44 (brs, 2H). HRMS calcd. for $C_{15}H_{10}D_6N_2O_2S$ [M+H]⁺295.1387. Found 295.1304.

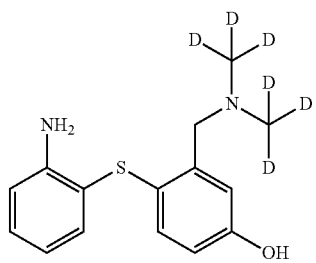

III-2-5

A solution of compound III-2-4 (200 mg, 0.68 mmol) was stirred in anhydrous THF (4 mL) at room temperature. Then 1M BH$_3$ in THF (3.4 mL, 3.40 mmol) was added. The reaction mixture was refluxed for 8 hours. When finished, the mixture was cooled and 0.5 mL concentrated HCl (0.5 mL) was cautiously added and the solvent was removed in vacuum. 10 mL of 1M HCl solution was added, then refluxed for 1 hour, cooled to room temperature and pH was adjusted to 8 with saturated solution of Na$_2$CO$_3$. The solution was extracted with EA (20 mL×3), the organic layers were combined and dried over anhydrous MgSO$_4$, filtered and the filtrate was evaporated in vacuum. It was purified by flash chromatography (silica gel) (methanol/EA, 0% to 10%, vol/vol) to get product III-2-5 (135 mg, yield 71%) as a colorless waxy material. $^1$H NMR (400 MHz, MeOD) δ 7.16 (dd, J=7.7, 1.5 Hz, 1H), 7.12-7.08 (m, 1H), 6.93 (d, J=8.5 Hz, 1H), 6.83 (d, J=2.7 Hz, 1H), 6.78 (dd, J=8.1, 1.3 Hz, 1H), 6.66-6.61 (m, 2H), 3.60 (s, 2H). $^{13}$C NMR (100 MHz, MeOD) δ 156.32, 148.33, 138.51, 134.51, 131.68, 129.18, 124.90, 117.71, 117.41, 117.33, 115.20, 115.15, 60.85. HRMS calcd. for C$_{15}$H$_{12}$D$_6$N$_2$OS [M+H]$^+$ 281.1595. Found 281.1210.

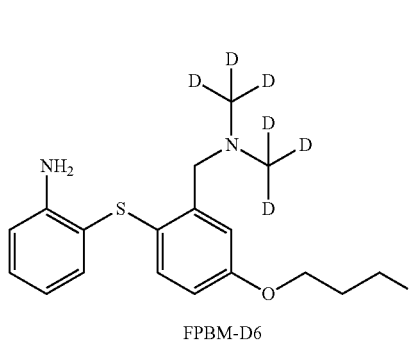

III-2
FPBM-D6

A mixture of compound III-2-5 (15 mg, 0.05 mmol) and K$_2$CO$_3$ (22 mg, 0.16 mmol) was stirred in anhydrous DMF (3 mL) at 65° C. for 1.5 hours. Then 3-fluoropropyl-4-methylbenzenesulfonate (25 mg, 0.10 mmol) was added and the mixture was stirred for another 2 hours, cooled to room temperature and a saturated solution of NaCl (12 mL) was added. The mixture was extracted with EA (15 mL×3), the organic layers were combined and dried over MgSO$_4$, filtered and the filtrate was evaporated in vacuum, purified by flash chromatography (silica gel) (THF/Hexane, 0% to 60%, vol/vol) to get product FPBM-D6, III-2 (6 mg, yield 35%) as a colorless waxy material. $^1$H NMR (400 MHz, Acetone) δ 7.33 (dd, J=7.7, 1.5 Hz, 1H), 7.15-7.10 (m, 1H), 6.98 (t, J=5.1 Hz, 2H), 6.79-6.73 (m, 2H), 6.61 (d, J=1.1 Hz, 1H), 5.24 (d, J=13.6 Hz, 2H), 4.69 (t, J=5.9 Hz, 1H), 4.57 (t, J=5.9 Hz, 1H), 4.09 (t, J=6.2 Hz, 2H), 3.55 (s, 2H), 2.26 (s, 6H), 2.21-2.08 (m, 2H). $^{13}$C NMR (100 MHz, Acetone) δ157.53, 149.70, 139.69, 136.17, 131.11, 130.00, 127.37, 116.71, 116.25, 116.04, 114.80, 113.90, 81.36, 79.75, 63.63, 63.57, 61.88, 44.53. HRMS calcd. for C$_{18}$H$_{17}$D$_6$FN$_2$OS [M+H]$^+$ 341.1970. Found 341.1912.

Example 14

Synthesis of Compound FPBM-D12 (III-3)

Scheme 14

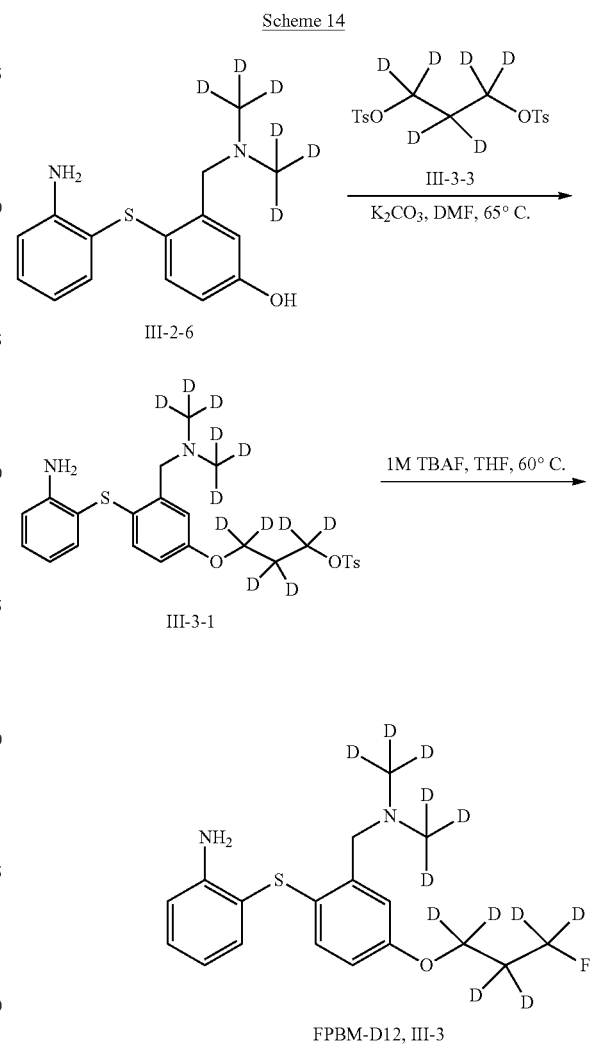

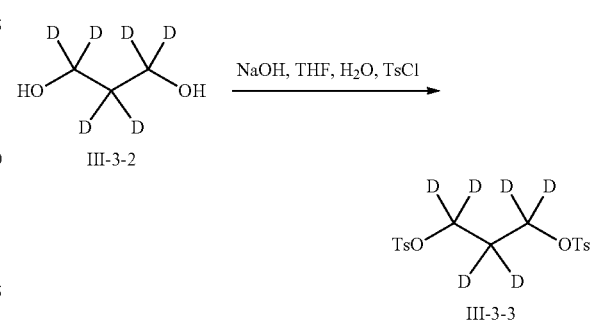

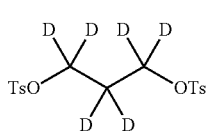

III-3-3

To a solution of compound III-3-2 (270 mg, 3.29 mmol) (99 atom % D) in THF (10 mL) was added NaOH (527 mg, 13.17 mmol) in water (5 mL) at 0° C. The reaction mixture was stirred at room temperature for 1 hour. TsCl (1.88 g, 9.88 mmol) in THF (10 mL) was then added drop wise. The reaction was stirred at room temperature for 24 hours. H$_2$O (20 mL) was added and the mixture was extracted with ethyl acetate (3×30 mL). The organic layers were combined and dried over anhydrous MgSO$_4$, filtered and the filtrate was evaporated in vacuum, purified by flash chromatography (silica gel) (EA/Hexane, 0% to 60%, vol/vol) to give [1,1,2,2,3,3-D$_6$]-propane-1,3-diylbis(4-methylbenzene-sulfonate), III-3-3, (970 mg, 76%) as a white solid. $^1$HNMR (400 MHz, CDCl$_3$) δ 7.78-7.76 (m, 4H), 7.38-7.36 (m, 4H), 2.483 (s, 6H), HRMS calcd. for C$_{17}$H$_{14}$D$_6$O$_6$S$_2$ [M+H]$^+$ 391.1156. Found 391.1140.

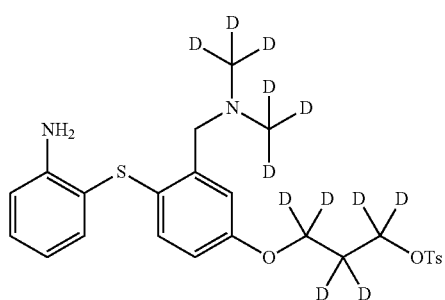

III-3-1

A mixture of compound III-2-6 (40 mg, 0.14 mmol) and K$_2$CO$_3$ (59 mg, 0.43 mmol) was stirred in anhydrous DMF (3 mL) at 65° C. for 1.5 hours. Then compound III-3-3 (67 mg, 0.17 mmol) was added and the mixture was stirred for another 2 h, cooled to room temperature and a saturated solution of NaCl (12 mL) was added. The mixture was extracted with EA (15 mL×3), the organic layers were combined and dried over MgSO$_4$, filtered and the filtrate was evaporated in vacuum, purified by flash chromatography (silica gel) (MeOH/DCM, 0% to 10%, vol/vol) to get product III-3-1 (38 mg, yield 54%) as a colorless waxy material. $^1$H NMR (400 MHz, Acetone) δ 7.76 (d, J=8.2 Hz, 2H), 7.39-7.33 (m, 3H), 7.12 (t, J=7.6 Hz, 1H), 6.95 (d, J=8.6 Hz, 1H), 6.87 (d, J=2.6 Hz, 1H), 6.77 (d, J=8.0 Hz, 1H), 6.63-6.59 (m, 2H), 5.31 (s, 1H), 3.55 (s, 2H), 2.37 (s, 3H). $^{13}$C NMR (100 MHz, Acetone) δ 157.30, 149.78, 144.89, 139.61, 136.24, 133.20, 131.03, 130.03, 129.94, 127.69, 127.34, 116.66, 116.03, 114.80, 113.94, 61.74, 20.62. HRMS calcd. for C$_{25}$H$_{18}$D$_{12}$N$_2$O$_4$S$_2$ [M+H]+ 499.2478. Found 499.2432.

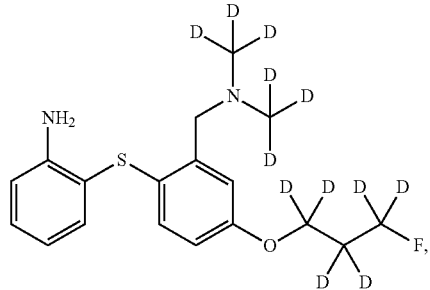

FPBM-D12

A mixture of compound III-3-1 (20 mg, 0.04 mmol) was stirred in anhydrous THF (3 mL) at 65° C. Then 1M TBAF in THF (0.2 mL, 0.20 mmol) was added, the reaction mixture was stirred for 3 h at 65° C., then the solvent was evaporated in vacuum. Water (8 mL) was added and the mixture was extracted with EA (15 mL×3). The organic layers were combined and dried over MgSO$_4$, filtered and the filtrate was evaporated in vacuum, purified by flash chromatography (silica gel) (THF/Hexane, 0% to 60%, vol/vol) to get product FPBM-D12, III-3 (7 mg, yield 50%) as a colorless waxy material. $^1$H NMR (400 MHz, CDCl$_3$) δ 7.41 (dd, J=8.0, 1.6 Hz, 1H), 7.20-7.14 (m, 1H), 6.96 (d, J=8.6 Hz, 1H), 6.90 (d, J=2.8 Hz, 1H), 6.76-6.66 (m, 3H), 4.55 (brs, 1H), 3.56 (s, 2H). $^{13}$C NMR (100 MHz, CDCl$_3$) δ 157.34, 148.29, 139.31, 136.33, 130.76, 130.08, 127.22, 118.21, 117.09, 116.39, 115.23, 114.08, 62.22. HRMS calcd. for C$_{18}$H$_{11}$D$_{12}$FN$_2$OS [M+H]$^+$ 347.2347. Found 347.24.

Example 15

Synthesis of Compound FPBM-D6 (III-4-2)

Scheme 15

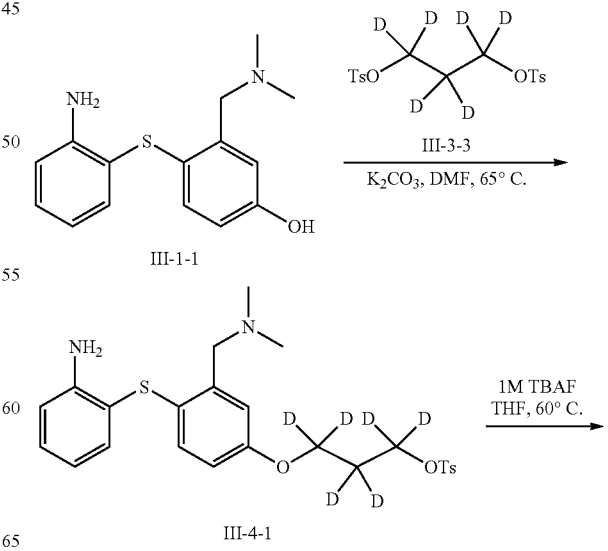

-continued

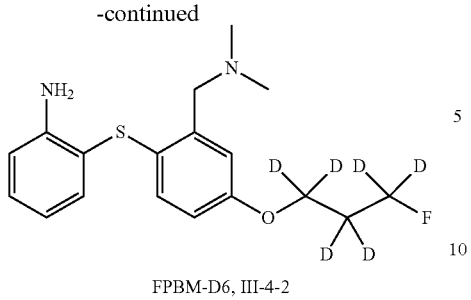

FPBM-D6, III-4-2

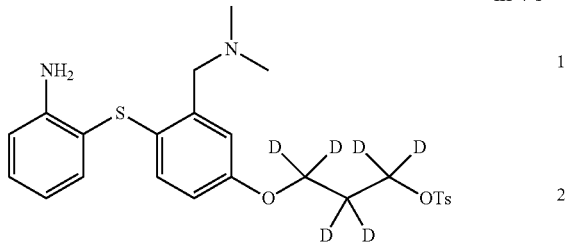

III-4-1

A mixture of compound III-1-1 (40 mg, 0.15 mmol) and K$_2$CO$_3$ (61 mg, 0.44 mmol) was stirred in anhydrous DMF (3 mL) at 65° C. for 1.5 h. Then compound III-3-3 (68 mg, 0.18 mmol) was added and the mixture was stirred for another 2 h, cooled to room temperature and a saturated solution of NaCl (10 mL) was added. The mixture was extracted with EA (15 mL×3), the organic layers were combined and dried over MgSO$_4$, filtered and the filtrate was evaporated in vacuum, purified by flash chromatography (silica gel) (MeOH/DCM, 0% to 10%, vol/vol) to get product III-4-1 (45 mg, 63%) as a colorless waxy material. $^1$H NMR (400 MHz, CDCl$_3$) δ 7.76 (d, J=8.3 Hz, 2H), 7.41 (dd, J=8.0, 1.5 Hz, 1H), 7.28-7.26 (m, 2H), 7.20-7.16 (m, 1H), 6.92 (d, J=8.6 Hz, 1H), 6.79 (d, J=2.8 Hz 1H), 6.74-6.70 (m, 2H), 6.53 (dd, J=8.6, 2.8 Hz, 1H), 4.56 (brs, 2H), 3.55 (s, 2H), 2.39 (s, 3H), 2.32 (s, 6H). $^{13}$C NMR (100 MHz, CDCl$_3$) δ 157.02, 148.36, 144.76, 139.21, 136.40, 132.86, 130.65, 130.16, 129.83, 127.84, 127.39, 118.20, 116.97, 116.18, 115.24, 114.10, 62.31, 45.33, 21.59. HRMS calcd. for C$_{25}$H$_{24}$D$_6$N$_2$O$_4$S$_2$ [M+H]$^+$ 493.2102. Found 493.2013.

III-4-2

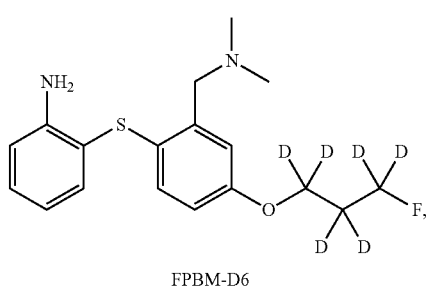

FPBM-D6

A mixture of compound III-4-1 (20 mg, 0.04 mmol) was stirred in anhydrous THF (5 mL) at 65° C. then 1M TBAF in THF (0.12 mL, 0.12 mmol) was added, the reaction mixture was stirred for 3 h at 65° C., then the solvent was evaporated in vacuum. Water (8 mL) was added and the mixture was extracted with EA (10 mL×3). The organic layers were combined and dried over MgSO$_4$, filtered and the filtrate was evaporated in vacuum, purified by flash chromatography (silica gel) (MeOH/DCM, 0% to 10%, vol/vol) to get product FPBM-D6, III-4-2 (7 mg, 51%) as a colorless waxy material. $^1$H NMR (400 MHz, CDCl$_3$) δ 7.39 (dd, J=8.1, 1.5 Hz, 1H), 7.19-7.14 (m, 1H), 6.97 (d, J=8.6 Hz, 1H), 6.93 (d, J=2.3 Hz, 1H), 6.75-6.66 (m, 3H), 3.59 (s, 2H), 2.33 (s, 6H). HRMS calcd. for C$_{18}$H$_{17}$D$_6$FN$_2$OS [M+H]$^+$ 341.1970. Found 341.2005.

Example 16

Synthesis of Compounds III-4-25 to III-4-28

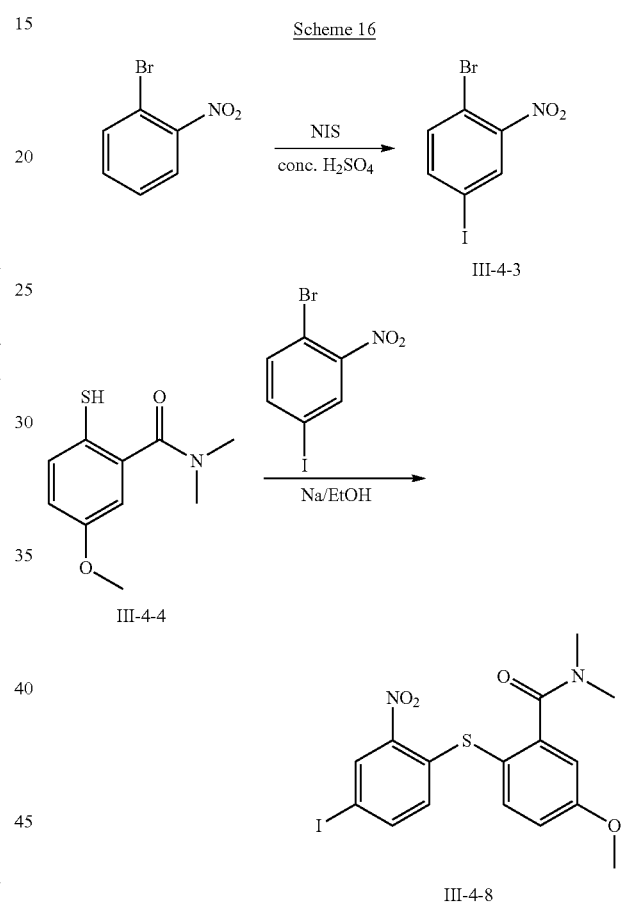

Scheme 17

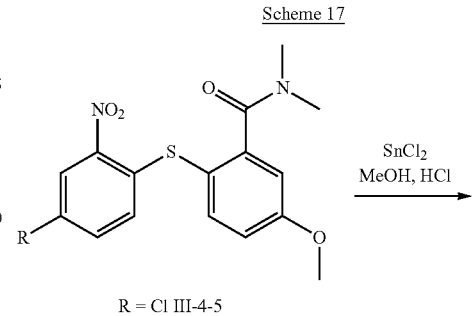

R = Cl III-4-5
R = Br III-4-6
R = F III-4-7
R = I III-4-8

-continued

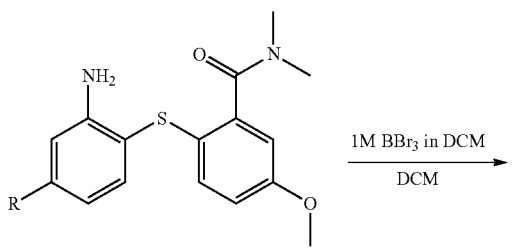

R = Cl  III-4-9
R = Br  III-4-10
R = F   III-4-11
R = I   III-4-12

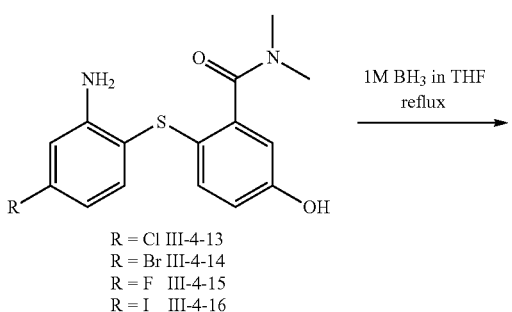

R = Cl  III-4-13
R = Br  III-4-14
R = F   III-4-15
R = I   III-4-16

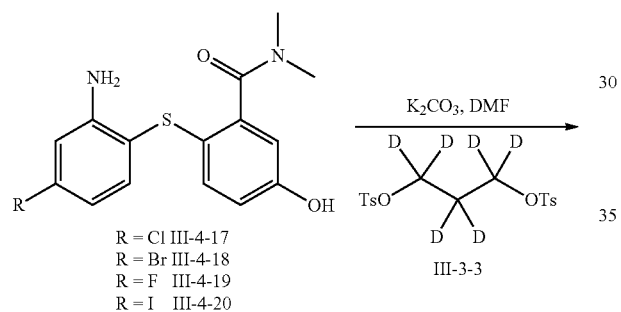

R = Cl  III-4-17
R = Br  III-4-18
R = F   III-4-19
R = I   III-4-20

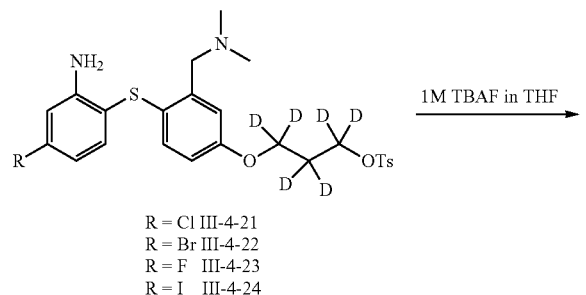

R = Cl  III-4-21
R = Br  III-4-22
R = F   III-4-23
R = I   III-4-24

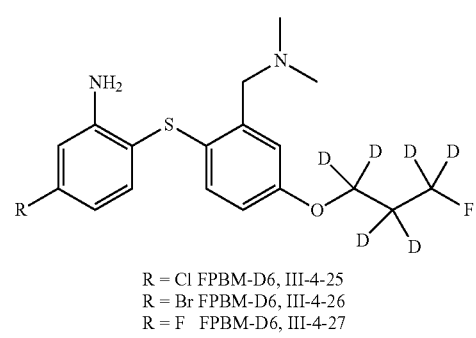

R = Cl  FPBM-D6, III-4-25
R = Br  FPBM-D6, III-4-26
R = F   FPBM-D6, III-4-27
R = I   FPBM-D6, III-4-28

-continued

III-4-3

A mixture of 1-bromo-2-nitrobenzene (1 g, 4.95 mmol) was stirred in concentrated $H_2SO_4$ (10 mL) at 0° C., NIS (1.23 g, 5.45 mmol) was added slowly. After complete addition, the reaction mixture was stirred at room temperature for 5 h, then ice water (30 mL) was added and extracted with EA (30 mL×3). The organic layers were combined and dried over $MgSO_4$, filtered and the filtrate was evaporated in vacuum, purified by flash chromatography (silica gel) (EA/Hexane, 0% to 15%, vol/vol) to get product III-4-3 (1.35 g, yield 84%) as a white solid. $^1$H NMR (400 MHz, $CDCl_3$) δ 8.15 (d, J=2.0 Hz, 1H), 7.75 (dd, J=8.4, 2.0 Hz, 1H), 7.47 (d, J=8.4 Hz, 1H).

III-4-8

Ethanol (20 mL) was stirred at 0° C., then sodium (356 mg, 15.48 mmol) was added slowly. After all sodium was consumed and become sodium ethoxide, the solvent was warmed to 80° C., and compound III-4-4 (1.31 g, 6.19 mmol) in ethanol (10 mL) was added and the reaction mixture was stirred at 80° C. for 1 h under $N_2$. Then compound III-4-3 (2.63 g, 8.05 mmol) was added and refluxed for 2 h. The solvent was evaporated and $H_2O$ (30 mL) was added, neutralized pH=5 with concentrated HCl, and extracted with EA (30 mL×3). The organic layers were combined and dried over anhydrous $MgSO_4$, filtered and the filtrate was evaporated in vacuum and purified by flash chromatography (silica gel) (EA/Hexane, 0% to 60%, vol/vol) to get product III-4-8 (1.6 g, 57%) as a yellow solid. $^1$H NMR (400 MHz, $CDCl_3$) δ 8.49 (d, J=1.8 Hz, 1H), 7.62 (dd, J=8.7, 1.8 Hz, 1H), 7.50 (d, J=8.6 Hz, 1H), 7.01 (dd, J=8.6, 2.6 Hz, 1H), 6.95 (d, J=2.7 Hz, 1H), 6.67 (d, J=8.7 Hz, 1H), 3.89 (s, 3H), 3.04 (s, 3H), 2.87 (s, 3H). $^{13}$C NMR (100 MHz, $CDCl_3$) δ 168.81, 161.87, 145.30, 145.07, 142.07, 139.17, 139.03, 133.87, 130.68, 116.97, 116.55, 112.72, 87.77, 55.68, 38.53, 34.60. HRMS calcd. for $C_{16}H_{15}IN_2O_4S$ [M+H]+ 458.9875. Found 458.9828.

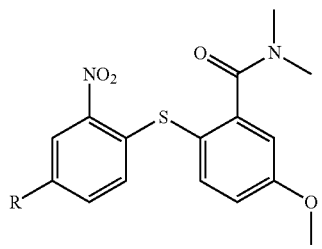

R = Cl   III-4-5
R = Br   III-4-6
R = F    III-4-7
R = I    III-4-8

General Procedure a for the Preparation of Compound III-4-9 to III-4-12

Compounds III-4-5 to III-4-8 (2 mmol) was stirred in methanol (10 mL) at 0° C. and concentrated HCl (5 mL) was added. Then $SnCl_2$ (1.52 g, 8 mmol) was added and the reaction mixture was stirred at room temperature overnight. After completion the mixture was diluted with water (30 mL) and basified to pH=10 with 2M aqueous solution of NaOH, and extracted with EA (30 mL×3). The organic layers were combined and dried over anhydrous $MgSO_4$, filtered and the filtrate was evaporated in vacuum and purified by flash chromatography (silica gel) (EA/Hexane, 0% to 80%, vol/vol) to get products III-4-9 to III-4-12 as a colorless waxy oil.

III-4-9

Compound III-4-9 was prepared from compound III-4-5 according to procedure A to give III-4-9 as a colorless waxy material, yield 68%. $^1$H NMR (400 MHz, $CDCl_3$) δ 7.38 (d, J=8.1 Hz, 1H), 7.13 (d, J=8.7 Hz, 1H), 6.81 (dd, J=8.7, 2.6 Hz, 1H), 6.74 (d, J=2.6 Hz, 1H), 6.69-6.61 (m, 2H), 4.67 (s, 2H), 3.79 (s, 3H), 3.16 (s, 3H), 2.87 (s, 3H). $^{13}$C NMR (100 MHz, $CDCl_3$) δ 170.01, 158.97, 149.65, 139.19, 137.61, 136.33, 132.75, 122.73, 117.72, 115.92, 114.74, 114.42, 111.45, 55.49, 38.53, 34.64. HRMS calcd. for $C_{16}H_{17}ClN_2O_2S$ [M+H]+ 337.0778. Found 337.0855.

III-4-10

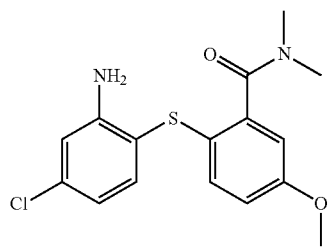

Compound III-4-10 was prepared from compound III-4-6 according to procedure A to give III-4-10 as a colorless waxy material, yield 69%. $^1$H NMR (400 MHz, $CDCl_3$) δ 7.30 (d, J=8.3 Hz, 1H), 7.11 (d, J=8.7 Hz, 1H), 6.87-6.74 (m, 4H), 4.76 (s, 2H), 3.79 (s, 3H), 3.17 (s, 3H), 2.88 (s, 3H). $^{13}$C NMR (100 MHz, $CDCl_3$) δ 170.42, 158.94, 149.66, 138.29, 137.76, 132.46, 124.61, 122.65, 120.82, 117.78, 116.17, 114.72, 111.61, 55.51, 38.63, 34.86. HRMS calcd. for $C_{16}H_{17}BrN_2O_2S$ [M+H]$^+$ 381.0272, 383.0252. Found 381.0183, 383.0162.

III-4-11

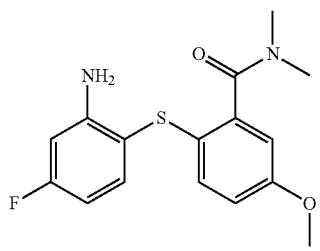

Compound III-4-11 was prepared from compound III-4-7 according to procedure A to give III-4-11 as a colorless waxy material, yield 71%. $^1$H NMR (400 MHz, $CDCl_3$) δ 7.48-7.40 (m, 1H), 7.10 (d, J=8.7 Hz, 1H), 6.80 (dd, J=8.7, 2.8 Hz, 1H), 6.74 (d, J=2.8 Hz, 1H), 6.43-6.35 (m, 2H), 4.71 (s, 2H), 3.78 (s, 3H), 3.17 (s, 3H), 2.88 (s, 3H). HRMS calcd. for $C_{16}H_{17}FN_2O_2S$ [M+H]$^+$ 321.1073. Found 321.1117.

III-4-12

Compound III-4-12 was prepared from compound III-4-8 according to procedure A to give III-4-12 as a colorless waxy material, yield 68%. $^1$H NMR (400 MHz, $CDCl_3$) δ 7.13 (dd, J=8.3, 6.5 Hz, 2H), 7.03 (d, J=1.5 Hz, 1H), 6.98 (dd, J=8.1, 1.6 Hz, 1H), 6.80 (dd, J=8.7, 2.6 Hz, 1H), 6.74 (d, J=2.6 Hz, 1H), 3.78 (s, 3H), 3.15 (s, 3H), 2.85 (s, 3H). $^{13}$C NMR (100 MHz, $CDCl_3$) δ 169.98, 159.00, 149.74, 139.27, 137.74, 132.91, 126.63, 123.65, 122.46, 115.93, 111.48, 96.47, 55.50, 38.54, 34.65. HRMS calcd. for $C_{16}H_{17}IN_2O_2S$ [M+H]$^+$429.0134. Found 429.0038.

General Procedure B for the Preparation of Compound III-4-13 to III-4-16

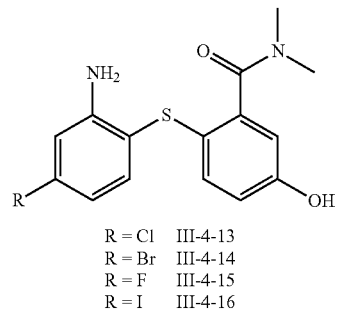

R = Cl  III-4-13
R = Br  III-4-14
R = F   III-4-15
R = I   III-4-16

A mixture of compound III-4-9 to III-4-12 (2 mmol) was stirred in anhydrous DCM (15 mL) at 0° C. Then 1M BBr$_3$ in DCM (6 mL, 6 mmol) was added drop wise under N$_2$. After complete addition the reaction mixture was stirred at room temperature overnight. After reaction, saturated solution of NaHCO$_3$ was added and the mixture was extracted with DCM (20 mL×2). The organic layers were combined and dried over anhydrous MgSO$_4$, filtered and the filtrate was evaporated in vacuum and purified by flash chromatography (silica gel) (EA/Hexane, 0% to 80%, vol/vol) to get product III-4-13 to III-4-16 as a colorless waxy material.

III-4-13

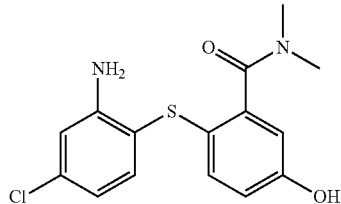

Compound III-4-13 was prepared from compound III-4-9 according to procedure B to give III-4-13 as a colorless waxy material, yield 68%. $^1$H NMR (400 MHz, MeOD) δ 7.27 (d, J=8.3 Hz, 1H), 7.12 (d, J=8.6 Hz, 1H), 6.78-6.76 (m, 2H), 6.65 (d, J=2.7 Hz, 1H), 6.58 (dd, J=8.3, 2.3 Hz, 1H), 3.08 (s, 3H), 2.78 (s, 3H). $^{13}$C NMR (100 MHz, MeOD) δ 170.69, 157.12, 150.35, 138.98, 136.85, 135.62, 132.88, 120.85, 116.81, 116.68, 114.20, 114.05, 113.12, 37.56, 33.50. HRMS calcd. for C$_{15}$H$_{15}$ClN$_2$O$_2$S [M+H]$^+$ 323.0621. Found 323.0658.

III-4-14

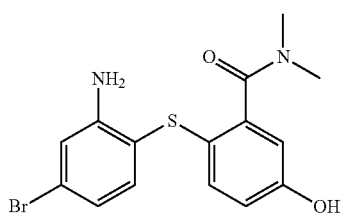

Compound III-4-14 was prepared from compound III-4-10 according to procedure B to give III-4-14 as a colorless waxy material, yield 71%. $^1$H NMR (400 MHz, CDCl$_3$) δ 7.26 (d, J=8.2 Hz, 1H), 6.87 (dd, J=7.9, 5.3 Hz, 2H), 6.80 (dd, J=8.2, 2.0 Hz, 1H), 6.64 (d, J=2.6 Hz, 1H), 6.60 (dd, J=8.6, 2.6 Hz, 1H), 3.14 (s, 3H), 2.85 (s, 3H). HRMS calcd. for C$_{15}$H$_{15}$BrN$_2$O$_2$S [M+H]$^+$ 367.0116, 369.0095. Found 367.0147, 369.0127.

III-4-15

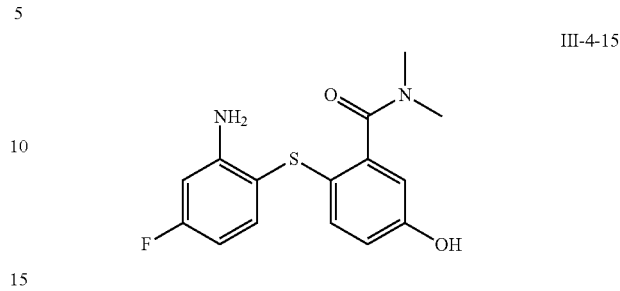

Compound III-4-15 was prepared from compound III-4-11 according to procedure B to give III-4-15 as a colorless waxy material, yield 69%. $^1$H NMR (400 MHz, CDCl$_3$) δ 7.40 (dd, J=9.2, 6.4 Hz, 1H), 6.87 (d, J=8.6 Hz, 1H), 6.66 (d, J=2.6 Hz, 1H), 6.60 (dd, J=8.5, 2.4 Hz, 1H), 6.44-6.35 (m, 2H), 3.17 (s, 3H), 2.89 (s, 3H). HRMS calcd. for C$_{15}$H$_{15}$FN$_2$O$_2$S [M+H]$^+$ 307.0917. Found 307.0947.

III-4-16

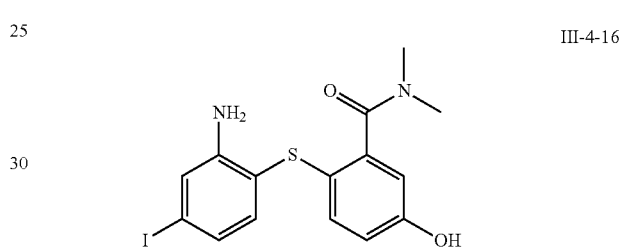

Compound III-4-16 was prepared from compound III-4-12 according to procedure B to give III-4-16 as a colorless waxy material, yield 68%. $^1$H NMR (400 MHz, CDCl$_3$) δ 7.08 (dd, J=16.6, 4.8 Hz, 2H), 7.02-6.99 (m, 1H), 6.87 (d, J=8.6 Hz, 1H), 6.64 (d, J=2.5 Hz, 1H), 6.58 (dd, J=8.6, 2.6 Hz, 1H), 4.48 (s, 2H), 3.16 (s, 3H), 2.86 (s, 3H). HRMS calcd. for C$_{15}$H$_{15}$IN$_2$O$_2$S [M+H]$^+$ 414.9977. Found 414.9912.

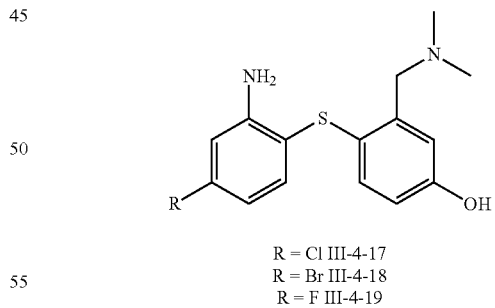

R = Cl III-4-17
R = Br III-4-18
R = F  III-4-19
R = I  III-4-20

General Procedure C for the Preparation of Compound III-4-17 to III-4-20

Compound III-4-13 to III-4-16 (1 mmol) was stirred in anhydrous THF (5 mL) at room temperature. Then 1M BH$_3$ in THF (3 mL, 3 mmol) was added, the reaction mixture was refluxed for 8 h. The mixture was cooled and 0.5 mL concentrate HCl was cautiously added. The solvent was removed in vacuum, and 1M HCl solution (10 mL) was added and refluxed for 1 h, cooled to room temperature and pH was adjusted to 8 with a saturated solution of Na₂CO₃, The mixture was extracted with EA (20 mL×3), the organic layers were combined and dried over anhydrous MgSO₄, filtered and the filtrate was evaporated in vacuum and purified by flash chromatography (silica gel) (EA/methanol, 0% to 10%, vol/vol) to get product III-4-17 to III-4-20 as a colorless waxy oil.

III-4-17

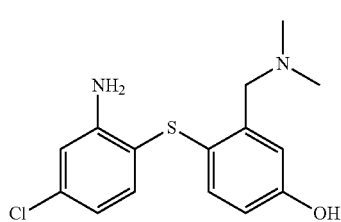

Compound III-4-17 was prepared from compound III-4-13 according to procedure C to give III-4-17 as a colorless waxy oil, yield 66%. ¹H NMR (400 MHz, CDCl₃) δ 7.24 (d, J=8.2 Hz, 1H), 6.87 (d, J=8.5 Hz, 1H), 6.73 (d, J=2.7 Hz, 1H), 6.70 (d, J=2.1 Hz, 1H), 6.66 (dd, J=8.2, 2.2 Hz, 1H), 6.59 (dd, J=8.5, 2.8 Hz, 1H), 3.56 (s, 2H), 2.32 (s, 6H). ¹³C NMR (100 MHz, CDCl₃) 155.25, 149.02, 138.47, 136.94, 135.69, 131.32, 125.79, 118.30, 118.04, 116.18, 115.61, 114.81, 61.60, 45.08. HRMS calcd. for $C_{15}H_{17}ClN_2OS$ [M+H]⁺309.0828. Found 309.0780.

III-4-18

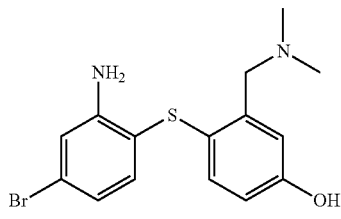

Compound III-4-18 was prepared from compound III-4-14 according to procedure C to give III-4-18 as a colorless waxy oil, yield 69%. ¹H NMR (400 MHz, CDCl₃) δ 7.17 (d, J=8.2 Hz, 1H), 6.91 (d, J=8.6 Hz, 1H), 6.85 (d, J=2.0 Hz, 1H), 6.83-6.77 (m, 2H), 6.62 (dd, J=8.6, 2.8 Hz, 1H), 4.79 (brs, 2H), 3.58 (s, 2H), 2.33 (s, 6H). ¹³C NMR (100 MHz, CDCl₃) δ 155.32, 149.13, 138.47, 136.98, 131.66, 125.56, 123.77, 121.13, 117.94, 117.70, 116.32, 116.16, 61.61, 45.02. HRMS calcd. for $C_{15}H_{17}BrN_2OS$ [M+H]⁺ 353.0323, 355.0303. Found 353.0284, 355.0277.

III-4-19

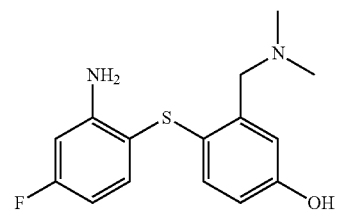

Compound III-4-19 was prepared from compound III-4-15 according to procedure C to give III-4-19 as a colorless waxy oil, yield 63%. ¹H NMR (400 MHz, MeOD) δ 7.26 (dd, J=8.5, 6.5 Hz, 1H), 6.85 (d, J=8.5 Hz, 1H), 6.78 (d, J=2.7 Hz, 1H), 6.61 (dd, J=8.5, 2.8 Hz, 1H), 6.48 (dd, J=11.2, 2.7 Hz, 1H), 6.37-6.32 (m, 1H), 3.57 (s, 2H), 2.31 (s, 6H). 13C NMR (100 MHz, MeOD) δ 165.75, 163.33, 155.92, 151.27, 151.14, 138.01, 137.47, 137.37, 130.55, 125.54, 117.35, 115.08, 111.68, 103.76, 103.54, 100.88, 100.63, 61.20, 44.02. HRMS calcd. for $C_{15}H_{17}FN_2OS$ [M+H]⁺ 293.1124. Found 293.0578.

III-4-20

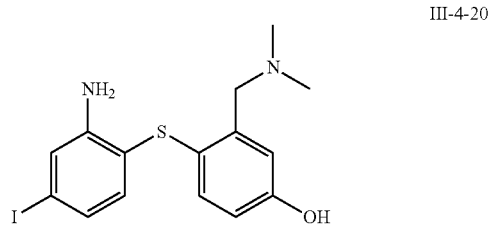 [SMILES: CN(C)Cc1cc(O)ccc1Sc1ccc(I)cc1N]

Compound III-4-20 was prepared from compound III-4-16 according to procedure C to give III-4-20 as a colorless waxy oil, yield 67%. ¹H NMR (400 MHz, MeOD) δ 7.13 (d, J=1.8 Hz, 1H), 7.00 (d, J=8.5 Hz, 1H), 6.91 (dd, J=8.1, 1.8 Hz, 1H), 6.84 (dd, J=5.4, 2.7 Hz, 2H), 6.68 (dd, J=8.5, 2.7 Hz, 1H), 3.67 (s, 2H), 2.37 (s, 6H). HRMS calcd. for $C_{15}H_{17}IN_2OS$ [M+H]⁺ 401.0185. Found 401.0158.

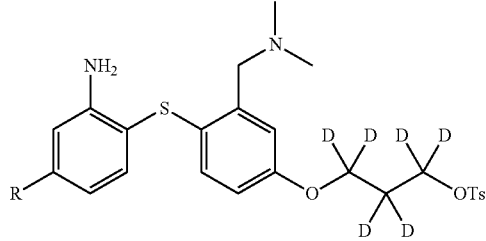

R = Cl III-4-21
R = Br III-4-22
R = F III-4-23
R = I III-4-24

General Procedure D for the Preparation of Compound III-4-21 to III-4-24

Compound III-4-17 to III-4-20 (0.1 mmol) and K₂CO₃ (41 mg, 0.3 mmol) were stirred in anhydrous DMF (3 mL) at 65° C. for 1.5 h, then compound II-3-3 (39 mg, 0.1 mmol) was added and the mixture was stirred for another 2 h, cooled to room temperature and saturated solution of NaCl (10 mL) was added. The mixture was extracted with EA (15 mL×3), the organic layers were combined and dried over MgSO₄, filtered and the filtrate was evaporated in vacuum, purified by flash chromatography (silica gel) (MeOH/DCM, 0% to 10%, vol/vol) to get compound III-4-21 to III-4-24 as a colorless oil.

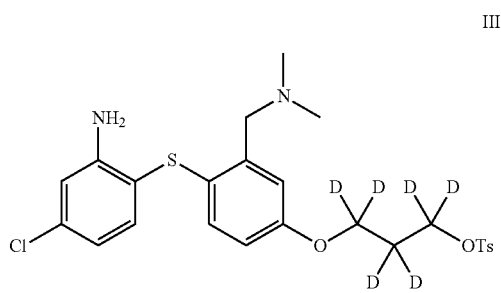

III-4-21

Compound III-4-21 was prepared from compound III-4-17 according to procedure D to give III-4-21 as a colorless oil, yield 50%. HRMS calcd. for $C_{25}H_{23}D_6ClN_2O_4S_2$ [M+H]$^+$ 527.1712. Found 527.1637.

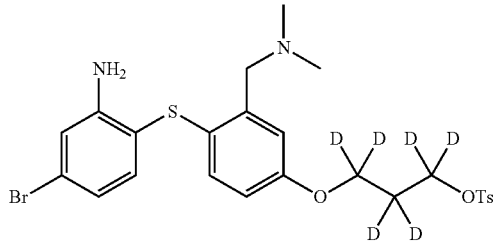

III-4-22

Compound III-4-22 was prepared from compound III-4-18 according to procedure D to give III-4-22 as a colorless oil, yield 51%. HRMS calcd. for $C_{25}H_{23}D_6BrN_2O_4S_2$ [M+H]$^+$ 571.1207, 573.1187. Found 571.1311, 573.1288.

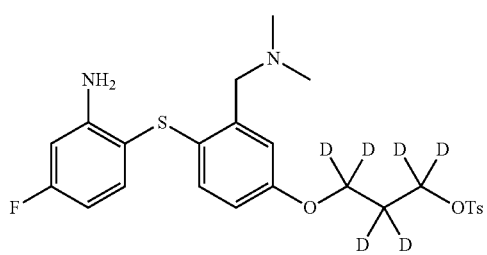

III-4-23

Compound III-4-23 was prepared from compound III-4-19 according to procedure D to give III-4-23 as a colorless oil, yield 58%. HRMS calcd. for $C_{25}H_{23}D_6FN_2O_4S_2$ [M+H]$^+$ 511.2008. Found 511.1965.

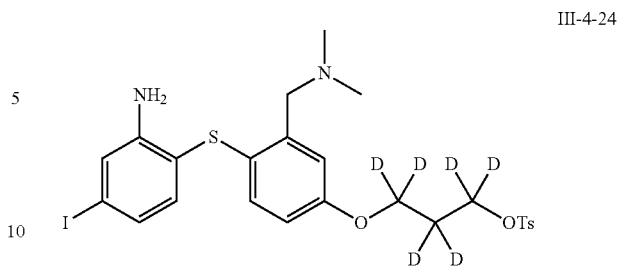

III-4-24

Compound III-4-24 was prepared from compound III-4-20 according to procedure D to give III-4-24 as a colorless oil, yield 53%. HRMS calcd. for $C_{25}H_{23}D_6IN_2O_4S_2$ [M+H]$^+$ 619.1068. Found 619.1003.

General Procedure E for the Preparation of Compound II-4-25 to II-4-28

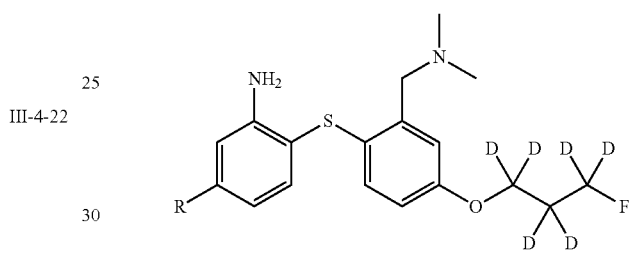

R = Cl FPBM-D6, III-4-25
R = Br FPBM-D6, III-4-26
R = F FPBM-D6, III-4-27
R = I FPBM-D6, III-4-28

Compound III-4-21 to III-4-24 (0.2 mmol) was stirred in anhydrous THF (5 mL) at 65° C. Then 1M TBAF in THF (0.6 mL, 0.6 mmol) was added. The reaction mixture was stirred for 3 h at 65° C., then the solvent was evaporated in vacuum, water (8 mL) was added. The mixture was extracted with EA (15 mL×3), the organic layers were combined and dried over MgSO$_4$, filtered and the filtrate was evaporated in vacuum, purified by flash chromatography (silica gel) (MeOH/DCM, 0% to 10%, vol/vol) to get product III-4-25 to III-4-28 as a colorless oil.

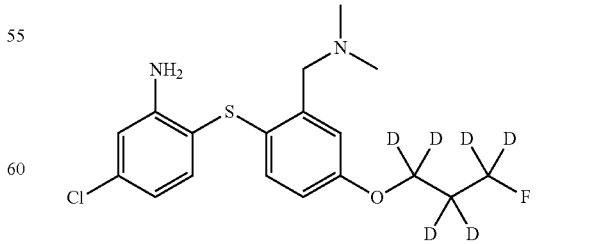

III-4-25

Compound III-4-25 was prepared from compound III-4-21 according to procedure E to give III-4-25 as a colorless oil, yield 60%. $^1$H NMR (400 MHz, CDCl$_3$) δ 7.35 (dd, J=7.8, 0.6 Hz, 1H), 6.97 (d, J=8.6 Hz, 1H), 6.86 (d, J=2.8 Hz, 1H), 6.74-6.65 (m, 3H), 4.79 (s, 2H), 3.54 (s, 2H), 2.31 (s, 6H). $^{13}$C NMR (100 MHz, CDCl$_3$) δ 157.47 149.38, 139.36, 137.43, 135.80, 131.13, 126.85, 117.91, 116.65, 115.56, 114.66, 114.17, 62.51, 45.25. HRMS calcd. for C$_{18}$H$_{16}$D$_6$ClFN$_2$OS [M+H]$^+$ 375.1580. Found 375.1649.

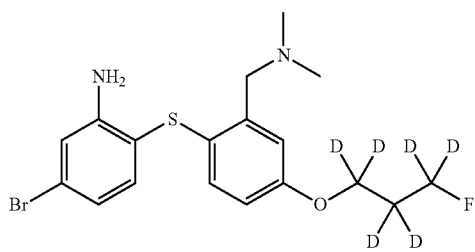

III-4-26

Compound III-4-26 was prepared used compound III-4-22 according to procedure E to give III-4-26 as a colorless oil, yield 57%. $^1$H NMR (400 MHz, CDCl$_3$) δ 7.26 (s, 1H), 6.98 (d, J=8.6 Hz, 1H), 6.85 (dd, J=5.3, 2.4 Hz, 2H), 6.81 (dd, J=8.1, 2.1 Hz, 1H), 6.70 (dd, J=8.6, 2.9 Hz, 1H), 4.78 (s, 2H), 3.54 (s, 2H), 2.31 (s, 6H). $^{13}$C NMR (100 MHz, CDCl$_3$) δ 157.51, 149.52, 139.45, 137.53, 131.26, 126.66, 123.93, 120.79, 117.56, 116.66, 116.21, 114.17, 62.52, 45.25. HRMS calcd. for C$_{18}$H$_{16}$D$_6$BrFN$_2$OS [M+H]$^+$ 419.1075, 421.1055. Found 419.1050, 421.1030.

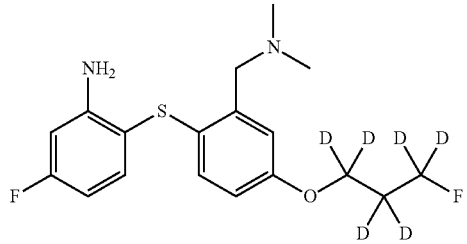

III-4-27

Compound III-4-27 was prepared from compound III-4-23 according to procedure E to give III-4-27 as a colorless oil, yield 52%. $^1$H NMR (400 MHz, CDCl$_3$) δ 7.43 (dd, J=8.2, 6.6 Hz, 1H), 6.93 (d, J=8.6 Hz, 1H), 6.85 (d, J=2.8 Hz, 1H), 6.70 (dd, J=8.6, 2.8 Hz, 1H), 6.45-6.38 (m, 2H), 4.86 (s, 2H), 3.55 (s, 2H), 2.32 (s, 6H). $^{13}$C NMR (100 MHz, CDCl$_3$) δ 165.84, 163.40, 157.25, 150.43, 150.31, 138.90, 138.54, 138.44, 130.48, 127.56, 116.63, 114.13, 112.03, 105.06, 104.84, 101.70, 101.45, 62.49, 45.25. HRMS calcd. for C$_{18}$H$_{16}$D$_6$F$_2$N$_2$OS [M+H]$^+$ 359.1876. Found 359.1793.

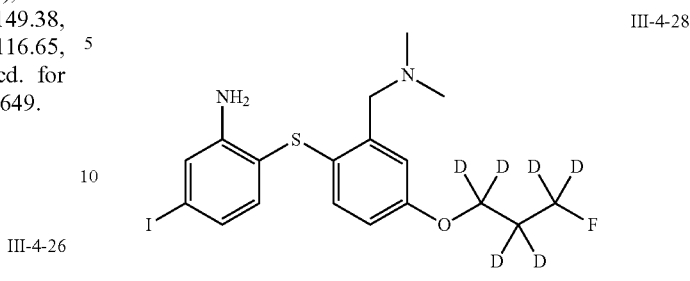

III-4-28

Compound III-4-28 was prepared from compound III-4-24 according to procedure F to give III-4-28 as a colorless oil, yield 55%. $^1$H NMR (400 MHz, MeOD) δ 7.14 (d, J=0.9 Hz, 1H), 6.99 (d, J=8.7 Hz, 1H), 6.95 (d, J=2.8 Hz, 1H), 6.92 (d, J=0.9 Hz, 2H), 6.79 (dd, J=8.7, 2.8 Hz, 1H), 3.60 (s, 2H), 2.31 (s, 6H). $^{13}$C NMR (100 MHz, MeOD) δ 157.92, 150.20, 138.69, 136.34, 131.21, 126.28, 125.91, 123.25, 116.58, 116.37, 114.19, 94.78, 61.17, 44.03. HRMS calcd. for C$_{18}$H$_{16}$D$_6$FIN$_2$OS [M+H]$^+$ 467.0936. Found 467.0887.

Example 17

Synthesis of Compound III-5-5

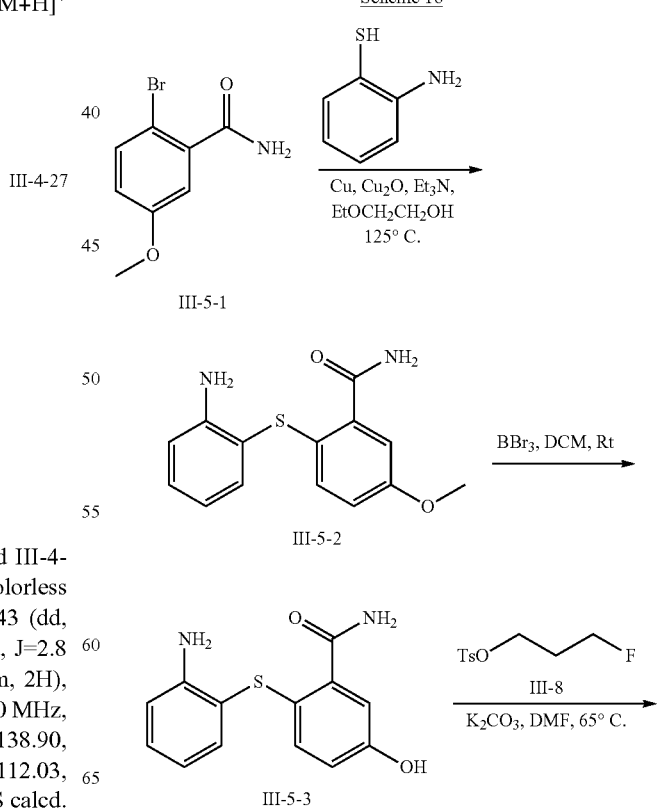

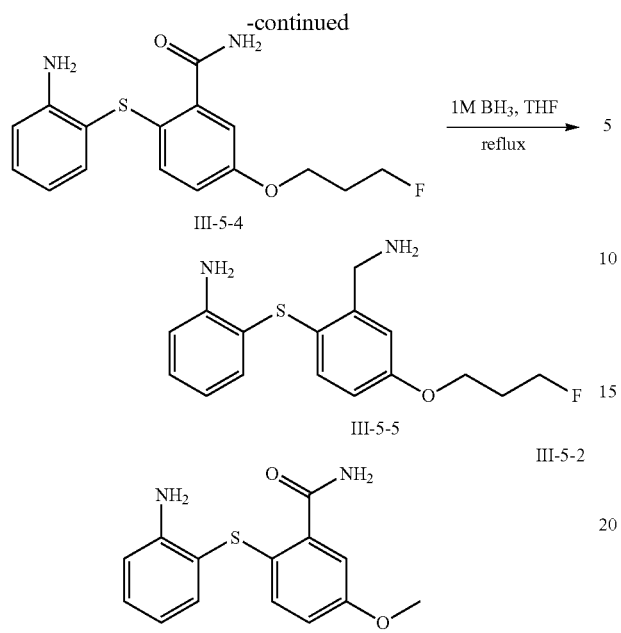

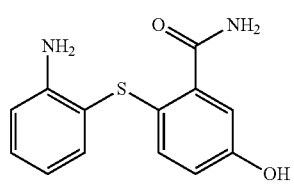

A mixture of compound III-5-1 (500 mg, 2.17 mmol), Cu (28 mg, 0.43 mmol), Cu$_2$O (31 mg, 0.22 mmol), 2-aminothiophenol (408 mg, 3.26 mmol) and Et$_3$N (2.20 g, 21.74 mmol) was stirred in 2-ethoxyethanol (8 mL) at 125° C. for 40 h. The mixture was filtered and washed with methanol (20 mL) and DCM (20 mL). The filtrate was evaporated in vacuum, purified by flash chromatography (silica gel) (EA/Hexane, 0% to 60%, vol/vol) to get product III-5-2 (350 mg, yield 59%) as a white solid. $^1$H NMR (400 MHz, MeOD) δ 7.36 (d, J=7.7 Hz, 1H), 7.18 (t, J=7.7 Hz, 1H), 7.07 (d, J=2.2 Hz, 1H), 6.90-6.79 (m, 3H), 6.67 (t, J=7.5 Hz, 1H), 3.79 (s, 3H). $^{13}$C NMR (100 MHz, MeOD) δ 172.24, 157.78, 149.77, 136.67, 136.00, 130.47, 129.60, 126.16, 117.51, 116.24, 115.11, 115.03, 112.96, 54.58. HRMS calcd. for C$_{14}$H$_{14}$N$_2$O$_2$S [M+H]$^+$ 275.0854. Found 275.0821.

Compound III-5-2 (350 mg, 1.28 mmol) was stirred in anhydrous DCM (15 mL) at 0° C., then 1M BBr$_3$ in DCM (3.83 mL, 3.83 mmol) was added drop wise under nitrogen. After addition the reaction mixture was refluxed for 5 h, cooled and a saturated solution of NaHCO$_3$ was added. The mixture was extracted with a solution of DCM/MeOH (10/1) (20 mL×3). The organic layers were combined and dried over anhydrous MgSO$_4$, filtered and the filtrate was evaporated in vacuum and purified by flash chromatography (silica gel) (EA/Hexane, 0% to 80%, vol/vol) to get product III-5-3 (230 mg, yield 69%) as a white solid. $^1$H NMR (400 MHz, MeOD) δ 7.35 (d, J=7.7 Hz, 1H), 7.16 (t, J=7.7 Hz, 1H), 6.93 (d, J=2.6 Hz, 1H), 6.81 (dd, J=10.4, 8.4 Hz, 2H), 6.73-6.63 (m, 2H). $^{13}$C NMR (100 MHz, MeOD) δ 172.54, 155.62, 149.51, 136.76, 136.38, 130.30, 130.21, 123.93, 117.52, 117.48, 115.70, 115.11, 114.30. HRMS calcd. for C$_{13}$H$_{12}$N$_2$O$_2$S [M+H]$^+$ 261.0698. Found 261.0687.

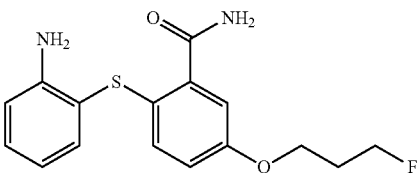

A mixture of compound III-5-3 (40 mg, 0.15 mmol) and K$_2$CO$_3$ (64 mg, 0.46 mmol) was stirred in anhydrous DMF (4 mL) at 65° C. for 1.5 h, then compound 3-fluoropropyl-4-methylbenzenesulfonate (71 mg, 0.30 mmol) was added and the mixture was stirred for another 2 h, cooled to room temperature and a saturated solution of NaCl (12 mL) was added. The mixture was extracted with EA (15 mL×3), the organic layers were combined and dried over MgSO$_4$, filtered and the filtrate was evaporated in vacuum, purified by flash chromatography (silica gel) (EA/Hexane, 0% to 70%, vol/vol) to get product III-5-4 (30 mg, yield 61%) as a white solid. $^1$H NMR (400 MHz, CDCl$_3$) δ 7.41 (dd, J=7.6, 1.4 Hz, 1H), 7.25-7.18 (m, 2H), 6.96 (d, J=8.8 Hz, 1H), 6.87-6.84 (m, 1H), 6.78-6.73 (m, 2H), 4.69 (t, J=5.7 Hz, 1H), 4.57 (t, J=5.7 Hz, 1H), 4.38 (brs, 2H), 4.09 (t, J=6.1 Hz, 2H), 2.22-2.10 (m, 2H). $^{13}$C NMR (100 MHz, CDCl$_3$) δ 169.62, 157.17, 148.61, 136.65, 135.07, 130.88, 126.27, 118.74, 117.89, 115.61, 115.46, 114.61, 81.28, 79.64, 63.94, 63.88, 30.39, 30.19. HRMS calcd. for C$_{16}$H$_{17}$FN$_2$O$_2$S [M+H]$^+$ 321.1073. Found 321.1120.

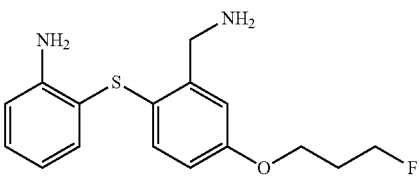

Compound III-5-4 (25 mg, 0.68 mmol) was stirred in anhydrous THF (4 mL) at room temperature. 1M BH$_3$ in THF (3.4 mL, 3.40 mmol) was added and the reaction mixture was refluxed for 8 h. The mixture was cooled and 0.5 mL concentrated HCl (0.2 mL) was cautiously added and the solvent was removed in vacuum. 1M HCl solution (5 mL) was added then refluxed for 1 h, cooled to room temperature and pH was adjusted to 8 with a saturated solution of Na$_2$CO$_3$. The mixture was extracted with EA (20 mL×3), the organic layers were combined and dried over anhydrous MgSO$_4$, filtered and the filtrate was evaporated in vacuum and purified by flash chromatography (silica gel) (methanol/DCM, 0% to 13%, vol/vol) to get product III-5-5 (12.5 mg, yield 52%) as a white solid. $^1$H NMR (400 MHz, CDCl$_3$) δ 7.29-7.25 (m, 1H), 7.19-7.15 (m, 1H), 7.02-6.97 (m, 2H), 6.78-6.68 (m, 3H), 4.70 (t, J=5.8 Hz, 1H), 4.59 (t, J=5.8 Hz, 1H), 4.09 (t, J=6.1 Hz, 2H), 3.99 (s, 2H), 2.26-2.07 (m, 2H). $^{13}$C NMR (100 MHz, CDCl$_3$) δ 158.18, 147.53, 143.82, 135.10, 131.30, 129.85, 124.73, 118.86, 116.79, 115.41, 114.89, 113.64, 81.46, 79.82, 63.64, 63.59, 62.74, 44.90. HRMS calcd. for C$_{16}$H$_{19}$FN$_2$OS [M+H]$^+$ 307.1280. Found 307.1291.

Example 18

Synthesis of Compound III-5-8

Scheme 19

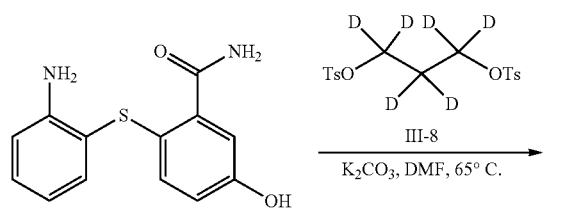

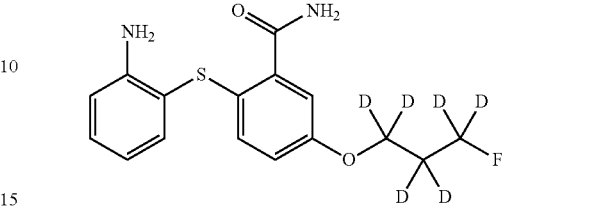

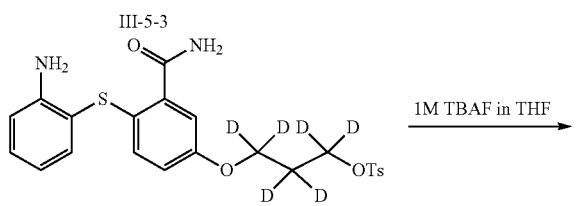

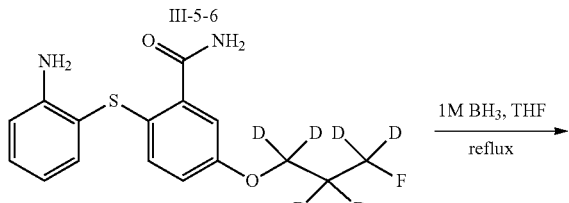

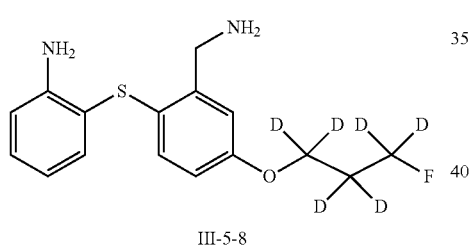

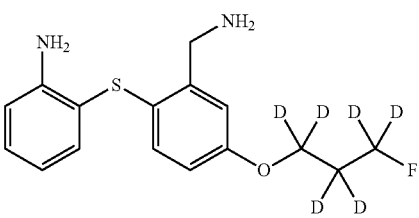

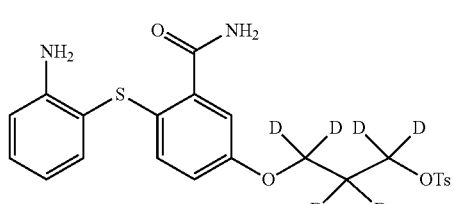

A mixture of compound III-5-3 (40 mg, 0.15 mmol) and K$_2$CO$_3$ (64 mg, 0.46 mmol) was stirred in anhydrous DMF (4 mL) at 65° C. for 1.5 h. Then compound III-8 (72 mg, 0.18 mmol) was added and the mixture was stirred for another 2 h, cooled to room temperature and a saturated solution of NaCl (12 mL) was added. The mixture was extracted with EA (15 mL×3), the organic layers were combined and dried over MgSO$_4$, filtered and the filtrate was evaporated in vacuum, purified by flash chromatography (silica gel) (EA/Hexane, 0% to 70%, vol/vol) to get product III-5-6 (37 mg, yield 50%) as a white solid. HRMS calcd. for C$_{23}$H$_{18}$D$_6$N$_2$O$_5$S$_2$ [M+H]$^+$ 479.1581. Found 479.1566.

Compound III-5-6 (37 mg, 0.08 mmol) was stirred in anhydrous THF (5 mL) at 65° C., then 1M TBAF in THF (0.23 mL, 0.23 mmol) was added. The reaction mixture was stirred for 3 h at 65° C., then the solvent was evaporated in vacuum, H$_2$O (8 mL) was added and the mixture was extracted with EA (15 mL×3). The organic layers were combined and dried over MgSO$_4$, filtered and the filtrate was evaporated in vacuum, purified by flash chromatography (silica gel) (EA/Hexane, 0% to 70%, vol/vol) to get product III-5-7 (14 mg, yield 56%) as a white solid. $^1$H NMR (400 MHz, MeOD) δ 7.36 (dd, J=7.7, 1.4 Hz, 1H), 7.20-7.16 (m, 1H), 7.10-7.09 (m, 1H), 6.86-6.80 (m, 3H), 6.89-6.65 (m, 1H).

Compound III-5-7 (14 mg, 0.04 mmol) was stirred in anhydrous THF (2 mL) at room temperature, then 1M BH$_3$ in THF (0.43 mL, 0.43 mmol) was added. The reaction mixture was refluxed for 8 h. The mixture was cooled and 0.5 mL concentrated HCl (0.2 mL) was cautiously added and the solvent was removed in vacuum. 1M HCl solution (5 mL) was added and refluxed for 1 h, cooled to room temperature and pH was adjusted to 8 with a saturated solution of Na$_2$CO$_3$. The mixture was extracted with EA (20 mL×3). The organic layers were combined and dried over anhydrous MgSO$_4$, filtered and the filtrate was evaporated in vacuum, purified by flash chromatography (silica gel) (methanol/DCM, 0% to 13%, vol/vol) to get product III-5-8 (7 mg, yield 52%) as a white solid. $^1$H NMR (400 MHz, CDCl$_3$) δ 7.26 (dd, J=7.7, 1.4 Hz, 1H), 7.19-7.15 (m, 1H), 7.04-6.97 (m, 2H), 6.79-6.70 (m, 3H), 4.02 (s, 2H), 3.52 (brs, 4H). $^{13}$C NMR (100 MHz, CDCl$_3$) δ 158.25, 147.50, 143.18, 135.05, 131.51, 129.89, 124.81, 118.93, 116.75, 115.49, 115.13, 113.96, 44.40. HRMS calcd. for C$_{16}$H$_{13}$D$_6$FN$_2$OS [M+H]$^+$ 313.1657. Found 313.1716.

Example 19

Synthesis of Compound III-6-5

Scheme 20

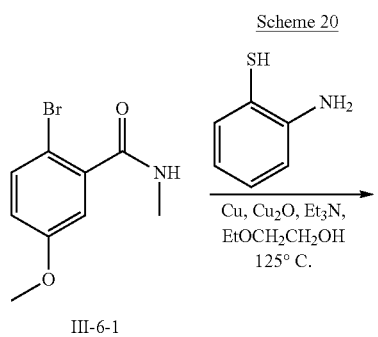

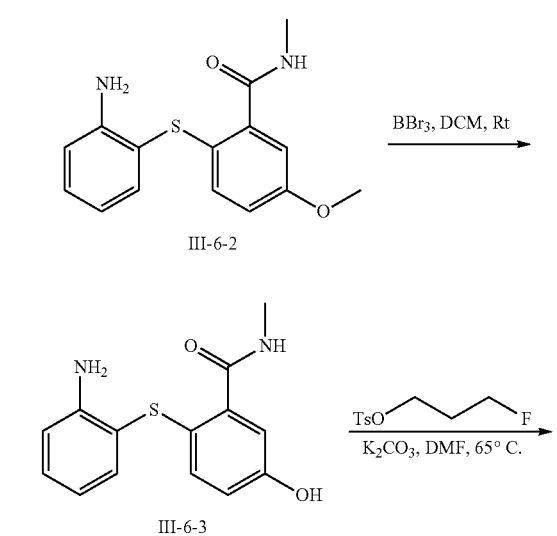

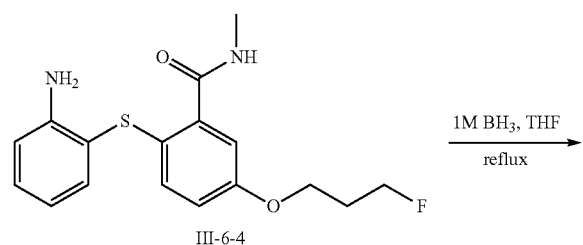

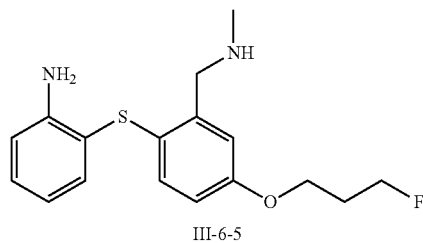

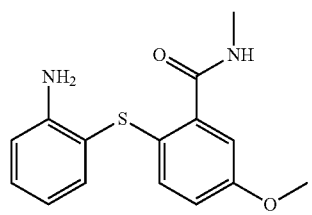

A mixture of compound III-6-1 (500 mg, 2.05 mmol), Cu (26 mg, 0.41 mmol), Cu$_2$O (29 mg, 0.21 mmol), 2-aminothiophenol (384 mg, 3.07 mmol) and Et$_3$N (2.07 g, 20.49 mmol) was stirred in 2-ethoxyethanol (8 mL) at 125° C. for 40 h. The mixture was filtered and washed with methanol (20 mL) and DCM (20 mL). The filtrate was evaporated in vacuum, purified by flash chromatography (silica gel) (EA/Hexane, 0% to 60%, vol/vol) to get product III-6-2 (350 mg, yield 59%) as a slight yellow solid. III-6-2 $^1$H NMR (400 MHz, MeOD) δ 7.34 (d, J=7.7 Hz, 1H), 7.17 (dd, J=10.7, 4.7 Hz, 1H), 6.98 (d, J=2.6 Hz, 1H), 6.94-6.78 (m, 3H), 6.66 (t, J=7.5 Hz, 1H), 3.78 (s, 3H), 2.92 (s, 3H). $^{13}$C NMR (100 MHz, MeOD) δ 170.43, 157.99, 149.64, 136.92, 136.47, 130.38, 129.99, 125.74, 117.50, 115.99, 115.11, 112.92, 54.59, 25.32. HRMS calcd. for C$_{15}$H$_{16}$N$_2$O$_2$S [M+H]$^+$ 289.1011. Found 289.1088.

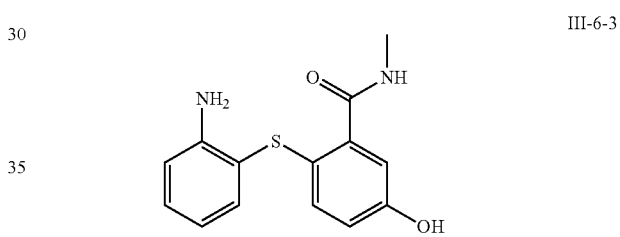

Compound III-6-2 (300 mg, 1.04 mmol) was stirred in anhydrous DCM (15 mL) at 0° C. Then 1M BBr$_3$ in DCM (3.13 mL, 3.13 mmol) was added drop wise under nitrogen. After addition the reaction mixture was stirred at room temperature; then a saturated solution of NaHCO$_3$ was added and extracted with DCM (20 mL×2). The organic layers were combined and dried over anhydrous MgSO$_4$, filtered and the filtrate was evaporated in vacuum and purified by flash chromatography (silica gel) (EA/Hexane, 0% to 70%, vol/vol) to get product III-6-3 (190 mg, yield 67%) as a colorless stick oil. $^1$H NMR (400 MHz, CDCl$_3$) δ 7.36 (dd, J=8.0, 1.5 Hz, 1H), 7.19-7.15 (m, 1H), 6.86 (dd, J=16.0, 5.7 Hz, 2H), 6.76-6.70 (m, 2H), 6.66 (dd, J=8.6, 2.7 Hz, 1H), 6.60 (d, J=4.8 Hz, 1H), 4.41 (brs, 2H). HRMS calcd. for C$_{14}$H$_{14}$N$_2$O$_2$S [M+H]$^+$ 275.0854. Found 275.0867.

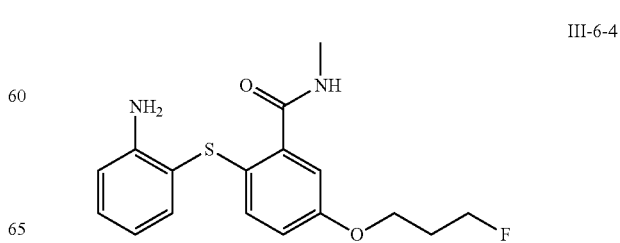

A mixture of compound III-6-3 (40 mg, 0.15 mmol) and K$_2$CO$_3$ (61 mg, 0.44 mmol) was stirred in anhydrous DMF (3 mL) at 65° C. for 1.5 h. Compound 3-fluoropropyl-4-methylbenzenesulfonate (68 mg, 0.30 mmol) was added and the mixture was stirred for another 2 h, cooled to room temperature and saturated solution of NaCl (12 mL) was added. The mixture was extracted with EA (15 mL×3). The organic layers were combined and dried over MgSO$_4$, filtered and the filtrate was evaporated in vacuum, purified by flash chromatography (silica gel) (EA/Hexane, 0% to 80%, vol/vol) to get product III-6-4 (30 mg, yield 61%) as a colorless stick oil. HRMS calcd. for C$_{17}$H$_{19}$FN$_2$O$_2$S [M+H]$^+$ 335.1230. Found 335.1185.

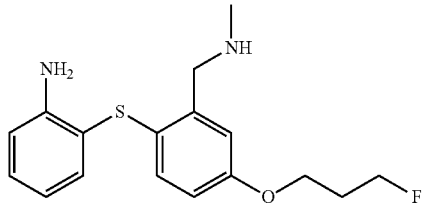

III-6-5

A mixture of compound III-6-4 (30 mg, 0.09 mmol) was stirred in anhydrous THF (4 mL) at room temperature. Then 1M BH$_3$ in THF (0.9 mL, 0.90 mmol) was added. The reaction mixture was refluxed for 8 h. The mixture was cooled and 0.5 mL concentrated HCl (0.5 mL) was cautiously added and the solvent was removed in vacuum. 1M HCl solution (10 mL) was added then refluxed for 1 h, cooled to room temperature and pH adjusted to 8 with a saturated solution of Na$_2$CO$_3$. The mixture was extracted with EA (20 mL×3). The organic layers were combined and dried over anhydrous MgSO$_4$, filtered and the filtrate was evaporated in vacuum, purified by flash chromatography (silica gel) (Methanol/DCM, 0% to 13%, vol/vol) to get product, III-6-5 (15 mg, yield 52%) as a colorless stick oil. $^1$H NMR (400 MHz, CDCl$_3$) δ 7.31 (dd, J=7.7, 1.4 Hz, 1H), 7.19-7.15 (m, 1H), 6.97 (dd, J=11.8, 5.7 Hz, 2H), 6.78-6.69 (m, 3H), 4.70 (t, J=5.8 Hz, 1H), 4.57 (d, J=5.8 Hz, 1H), 4.08 (t, J=6.1 Hz, 2H), 3.90 (s, 2H), 2.50 (s, 3H), 2.21-2.11 (m, 2H). $^{13}$C NMR (100 MHz, CDCl$_3$) δ 157.80, 147.73, 140.44, 135.43, 131.05, 129.93, 125.66, 118.69, 116.84, 115.87, 115.37, 114.08, 81.48, 79.84, 63.63, 63.58, 54.07, 36.02, 30.50, 30.30. HRMS calcd. for C$_{17}$H$_{21}$FN$_2$OS [M+H]$^+$ 321.1437. Found 321.1451.

Example 20

Synthesis of Compound III-6-8

Scheme 20

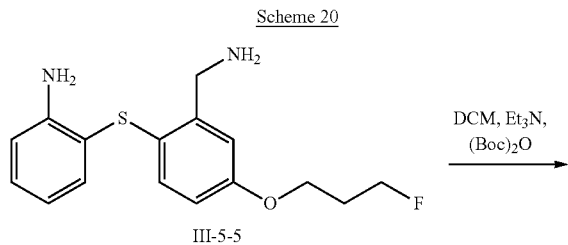

III-5-5 → (DCM, Et$_3$N, (Boc)$_2$O) → III-6-6

-continued

III-6-6 → (60% NaH, DMF, Deuterated iodomethane) → III-6-7

III-6-7 → (CF$_3$COOH) → III-6-8

III-6-6

A mixture of compound III-5-5 (20 mg, 0.07 mmol) and Et$_3$N (33 mg, 0.33 mmol) was stirred in anhydrous DCM (7 mL) at 0° C. (Boc)$_2$O (30 mg, 0.14 mmol) was added drop wise. After addition the reaction was stirred at room temperature for 3 h. Then H$_2$O (30 mL) was added. The mixture was extracted with DCM (10 mL×2), the organic layers were combined and dried over anhydrous MgSO$_4$, filtered and the filtrate was evaporated in vacuum, purified by flash chromatography (silica gel) (EA/Hexane, 0% to 70%, vol/vol) to get product III-6-6 (17 mg, 64%) as a colorless oil. $^1$H NMR (400 MHz, CDCl$_3$) δ 7.24 (d, J=7.7 Hz, 1H), 7.19-7.13 (m, 1H), 7.03 (d, J=8.6 Hz, 1H), 6.96 (d, J=2.4 Hz, 1H), 6.77-6.70 (m, 3H), 4.96 (s, 1H), 4.70 (t, J=5.8 Hz, 1H), 4.58 (t, J=5.8 Hz, 1H), 4.44 (d, J=5.6 Hz, 2H), 4.22 (s, 2H), 4.08 (t, J=6.1 Hz, 2H), 2.24-2.04 (m, 2H), 1.47 (s, 9H). $^{13}$C NMR (100 MHz, CDCl$_3$) 158.16, 155.79, 147.36, 139.82, 134.90, 131.60, 129.84, 118.96, 115.48, 115.36, 114.30, 81.43, 79.79, 77.32, 63.66, 63.60, 42.97, 30.45, 30.25, 28.41. HRMS calcd. for C$_{21}$H$_{27}$FN$_2$O$_3$S [M+H]$^+$ 407.1805. Found 407.1763.

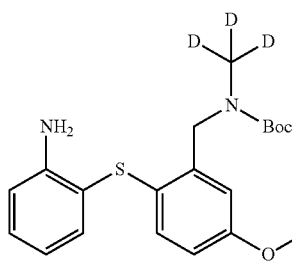

III-6-7

Compound III-6-6 (17 mg, 0.04 mmol) was stirred in anhydrous DMF (2 mL) at 0° C., then 60% NaH (3.3 mg, 0.08 mmol) was added slowly. After addition, the reaction was stirred at 0° C. for 30 min. Deuterated iodomethane (9 mg, 0.06 mmol) was added and stirred for another 1 h at 0° C. Saturated solution of NaCl (15 mL) was added and the mixture was extracted with EA (20 mL×2). The organic layers were combined and dried over anhydrous $MgSO_4$, filtered and the filtrate was evaporated in vacuum, purified by flash chromatography (silica gel) (EA/Hexane, 0% to 50%, vol/vol) to get product III-6-7 (13 mg, 73%) as a white solid. $^1H$ NMR (400 MHz, $CDCl_3$) δ 7.18-7.14 (m, 2H), 7.04-6.94 (m, 1H), 6.77-6.70 (m, 4H), 4.70 (t, J=5.8 Hz, 1H), 4.58 (t, J=5.8 Hz, 1H), 4.19 (brs, 2H), 4.07 (t, J=6.1 Hz, 2H), 2.22-2.10 (m, 2H), 1.52-1.46 (m, 9H). HRMS calcd. for $C_{22}H_{26}D_3FN_2O_3S$ [M+H]$^+$ 424.2149. Found 424.2158.

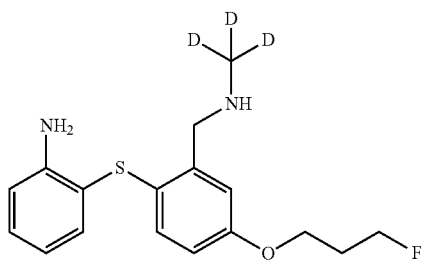

III-6-8

Compound III-6-7 (13 mg, 0.03 mmol) was stirred in $CF_3COOH$ (3 mL) at room temperature overnight, then the solvent was evaporated in vacuum. The pH was adjusted to 8 with a saturated solution of $Na_2CO_3$ The mixture was extracted with EA (10 mL×3), the organic layers were combined and dried over anhydrous $MgSO_4$, filtered and the filtrate was evaporated in vacuum, purified by flash chromatography (silica gel) (EA/Methanol, 0% to 10%, vol/vol) to get product III-6-8 (5 mg, 50%) as a colorless oil. $^1H$ NMR (400 MHz, $CDCl_3$) δ 7.29-7.27 (m, 1H), 7.20-7.15 (m, 1H), 7.04-7.01 (m, 2H), 6.77-6.71 (m, 3H), 4.69 (t, J=5.8 Hz, 1H), 4.57 (t, J=5.8 Hz, 1H), 4.08 (t, J=6.1 Hz, 2H), 3.99 (s, 2H), 2.23-2.04 (m, 2H). $^{13}C$ NMR (100 MHz, $CDCl_3$) δ 157.99, 147.71, 137.89, 135.36, 131.44, 130.08, 126.01, 118.86, 116.50, 116.27, 115.55, 114.97, 81.43, 79.79, 63.70, 63.65, 52.86, 30.44, 30.24. HRMS calcd. for $C_{17}H_{18}D_3FN_2OS$ [M+H]$^+$ 324.1625. Found 324.1628.

Example 21

Radiolabeling of $^{18}F$-III-3 ($^{18}F$—FPBM-D12)

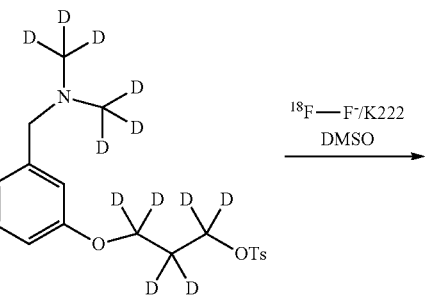

FPBM-D12, III-3-1

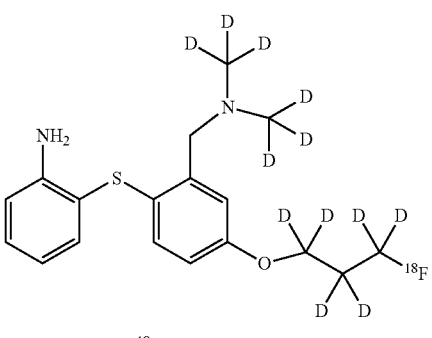

$^{18}F$-FPBM-D12, III-3

Preparation of $^{18}F$-III-3 ($^{18}F$—FPBM-$D_{12}$) by radiolabeling was accomplished by the following steps. $^{18}F$ fluoride was loaded on an activated QMA light cartridge and eluted with 0.7 mL $K_{222}/K_2CO_3$ solution (40 mg $K_2CO_3$, 220 mg $K_{222}$, 3.6 mL water, 18.4 mL ACN) into a conical vial. The solution was dried under a flow of argon at 80° C. and azeotropically dried twice with 1 mL acetonitrile. 2 mg precursor was dissolved in 0.5 ml acetonitrile (anhydrous) and added to dried $^{18}F$ $F^-/K_{222}/K_2CO_3$ complex. The reaction mixture, containing III-3-1, was heated for 15 min at 80° C. The resulting reaction mixture was cooled to room temperature and added to 8 mL water. The mixture was loaded onto an Oasis HLB (3 cc) cartridge. Cartridge was eluted and washed twice with 3 mL water. The desired $^{18}F$-III-3 was eluted with 1 ml acetonitrile (yield: 53%, RCP ~99% HPLC (Supelco Ascentis 150×4.6 mm, ACN/10 mM ammonium format buffer (AFB) 50/50, 1 mL/min). 1 mL of water was added to this solution and injected onto prep HPLC (Phenomenx Gemini 250×10 mm, ACN/water 60/40, 4 mL/min). The eluent of the desired $^{18}F$-III-3 was collected (14.5 mCi, retention time 21-22 min). The solution was mixed with 30 mL water and added onto an Oasis HLB 3 cc. The activity was eluted with 1 mL 100% ethanol (12.2 mCi). The solution was concentrated to about 200 μL volume and diluted with 1.8 mL buffer. Radio profile on HPLC (HPLC: Supelco Ascentis 150×4.6 mm, ACN/10 mM AFB 50/50, 1 mL/min) showed single peak at 4 minutes for $^{18}F$-III-3

(¹⁸F—FPBM-D12), RCY 32% (dc): RCP: 99%; SA~1700 Ci/mmol (determined at 280 nm). The retention time corresponded to cold III-3 confirming the chemical identity.

Example 22

In Vitro Binding Assays

The membrane homogenates of serotonin transporters (LLC-SERT, which were expressed in a common parental cell line LLC-PK1) were prepared and used for the binding assays. Competitive binding assays were performed in a final volume of 0.25 mL. Aliquots of membrane suspensions were mixed with 50 mM Tris-HCl, pH 7.4, 120 mM NaCl and 0.1% bovine serum albumin, 0.2 nM [$^{125}$I]IDAM, and 8-10 concentrations ($10^{-13}$ to $10^{-7}$M) of competing drugs. Nonspecific binding was defined with 10 μM citalopram. Incubation was carried out for 60 min at room temperature and the bound ligand was collected on glass fiber filters presoaked with 1% polyethylenimine (SIGMA, St. Louis, Mo.) and counted in a gamma counter (Wizard², Perkin Elmer). Data were analyzed using the nonlinear least-square curve fitting program LIGAND to determine $IC_{50}$ and Ki was calculated by Cheng-Prusoff equation using 0.2 nM as Kd of [$^{125}$I]IDAM.

TABLE 3a

A ring halogen (X) substitution on SERT binding affinity.

| X | | Ki (nM) |
|---|---|---|
| H | III-1-1 | 1.21 ± 0.15 |
| F | III-4-19 | 0.22 ± 0.06 |
| Cl | III-4-17 | 0.03 ± 0.01 |
| Br | III-4-18 | 0.02 ± 0.002 |
| H | III-4-2 | 0.14 ± 0.06 |
| F | III-4-27 | 0.024 ± 0.004 |
| Cl | III-4-25 | 0.009 ± 0.004 |
| Br | III-4-26 | 0.021 ± 0.003 |
| I | III-4-28 | 0.008 ± 0.003 |

Deuterated

The binding affinity of deuterated agents in this series showed very high binding affinity. Adding fluoropropyl-D6 group showed comparable binding affinity.

TABLE 3b

The effect of N-methyl substitution groups on SERT binding affinity.

| | Ki (nM) | Deuterated | | Ki (nM) |
|---|---|---|---|---|
| III-1 (FPBM) | 0.052 ± 0.007 | | III-4-2 | 0.14 ± 0.06 |
| III-6-5 | 5.26 ± 0.66 | | III-6-8 | 3.05 ± 0.81 |
| III-5-5 | 39.3 ± 11.9 | | III-5-8 | 44.9 ± 2.5 |

In this series of agents the binding affinity is dependent on the N,N-dimehtyl substitution with the di-substituted compound with or without deuterium show the highest binding affinity.

TABLE 3c

Hydrogen vs Deuterium substitution on SERT binding affinity.

| Structure | Compound | Ki (nM) | Deuterated Structure | Compound | Ki (nM) |
|---|---|---|---|---|---|
| (structure) | III-1-1 | 1.21 ± 0.15 | (structure) | III-2-4 | 2.02 ± 0.54 |
| (structure) | III-1 (FPBM) | 0.052 ± 0.007 | (structure) | III-2 | 0.032 ± 0.013 |
| | | | (structure) | III-3 (FPBM-D12) | 0.086 ± 0.029 |
| (structure) | | 0.022 ± 0.016 | (structure) | III-4-27 | 0.024 ± 0.004 |
| (structure) | III-5-5 | 39.3 ± 11.9 | (structure) | III-5-8 | 44.9 ± 2.5 |
| (structure) | III-6-5 | 5.26 ± 0.66 | (structure) | III-6-8 | 3.05 ± 0.81 |

Binding affinity study shows that the deuterated agents all display comparable binding affinity towards SERT binding sites when compared to the corresponding non-deuterated agents. The novel deuterated agents can be useful for binding to SERT binding sites.

Example 23

Biodistribution in Rats

Three rats per group were used for each biodistribution study. While under isoflurane anesthesia, 0.2 mL of a saline solution containing 20 µCi of radioactive tracer was injected into the femoral vein. The rats were sacrificed at the time indicated by cardiac excision while under isoflurane anesthesia. Organs of interest were removed and weighed, and the radioactivity was counted. The percent dose per organ was calculated by comparing the tissue counts to counts of 1% of the initial dose (100 times diluted aliquots of the injected material) measured at the same time. Regional brain distribution in rats was measured after an iv injection of the radioactive tracer. Samples from different brain regions [cortex, striatum, hippocampus, cerebellum and hypothalamus] were dissected, weighed and counted. The percentage dose/g of each sample was calculated by comparing sample counts with the counts of the diluted initial dose described above. The ratio was calculated by dividing the percentage dose/g of each region by that of the cerebellum. The cerebellum was used as the reference region for calculating the ratio of target to non-target binding, because only a trace amount of SERT is present in the cerebellum.

TABLE 3d

Biodistribution of $^{18}$F-III-3 ($^{18}$F-FPBM-D12) in normal rats at different time points after an i.v. injection % Dose/g (Avg ± SD of n = 3).

|  | 2 min | 30 min | 60 min | 120 min |
| --- | --- | --- | --- | --- |
| Blood | 0.25 ± 0.04 | 0.16 ± 0.03 | 0.10 ± 0.02 | 0.06 ± 0.00 |
| Heart | 1.19 ± 0.18 | 0.18 ± 0.02 | 0.09 ± 0.01 | 0.05 ± 0.01 |
| Muscle | 0.14 ± 0.02 | 0.09 ± 0.02 | 0.07 ± 0.01 | 0.03 ± 0.01 |
| Lung | 9.56 ± 2.29 | 1.86 ± 0.42 | 0.850.11 | 0.450.10 |
| Kidney | 3.02 ± 0.16 | 1.79 ± 0.38 | 1.29 ± 0.29 | 0.83 ± 0.39 |
| Spleen | 1.48 ± 0.31 | 0.88 ± 0.05 | 0.46 ± 0.10 | 0.21 ± 0.04 |
| Pancreas | 1.13 ± 0.02 | 0.27 ± 0.06 | 0.19 ± 0.02 | 0.13 ± 0.07 |
| Liver | 0.74 ± 0.16 | 0.30 ± 0.05 | 0.22 ± 0.02 | 0.16 ± 0.01 |
| Skin | 0.22 ± 0.04 | 0.19 ± 0.03 | 0.16 ± 0.01 | 0.10 ± 0.02 |
| Bone | 0.35 ± 0.06 | 0.19 ± 0.01 | 0.16 ± 0.02 | 0.13 ± 0.01 |
| Brain | 1.09 ± 0.06 | 0.81 ± 0.04 | 0.54 ± 0.05 | 0.31 ± 0.03 |

Region to Cerebellum Ratio $^{18}$F-III-3 ($^{18}$F-FPBM-D12)

|  | 2 min | 30 min | 60 min | 120 min |
| --- | --- | --- | --- | --- |
| Hypothalamus | 1.17 ± 0.21 | 2.99 ± 0.46 | 5.32 ± 0.45 | 7.55 ± 0.82 |
| Cerebellum | 1.00 ± 0.00 | 1.00 ± 0.00 | 1.00 ± 0.00 | 1.00 ± 0.00 |
| Hippocampus | 0.97 ± 0.13 | 2.04 ± 0.27 | 3.45 ± 0.42 | 3.85 ± 0.28 |
| Cortex | 1.44 ± 0.27 | 1.81 ± 0.30 | 2.68 ± 0.35 | 2.67 ± 0.50 |
| Striatum | 1.15 ± 0.18 | 2.43 ± 0.38 | 3.96 ± 0.62 | 4.69 ± 1.26 |
| Remainder | 1.21 ± 0.13 | 2.42 ± 0.13 | 3.77 ± 0.43 | 4.74 ± 0.71 |

Region to Cerebellum Ratio $^{18}$F-III-1 ($^{18}$F-FPBM) (Reported previously, Wang, J. Nucl. Med. 2009, 50:1509-17)

| Organ | 2 min | 30 min | 60 min | 120 min |
| --- | --- | --- | --- | --- |
| Hypothalamus | 1.14 ± 0.16 | 3.50 ± 0.67 | 4.69 ± 1.76 | 7.67 ± 2.60 |
| Cerebellum | 1.00 ± 0.15 | 1.00 ± 0.19 | 1.00 ± 0.46 | 1.00 ± 0.33 |
| Hippocampus | 0.88 ± 0.11 | 2.26 ± 0.44 | 2.82 ± 1.06 | 3.87 ± 1.00 |
| Cortex | 1.03 ± 0.13 | 2.87 ± 0.64 | 4.26 ± 1.58 | 4.53 ± 1.33 |
| Striatum | 0.90 ± 0.10 | 2.58 ± 0.59 | 3.19 ± 1.23 | 4.67 ± 1.51 |
| Remainder | 0.98 ± 0.14 | 2.54 ± 0.40 | 3.11 ± 1.22 | 4.49 ± 1.29 |

The biodistribution study in rats after an i.v. injection of $^{18}$F-III-3 ($^{18}$F—FPBM-D12) showed that the new deuterated agent penetrated the blood-brain-barrier and localized in the regions, where the concentration of serotonin transporter binding sites are high, i.e., hypothalamus and striatum regions (Table 3d). The regional distribution of deuterated, $^{18}$F-III-3 ($^{18}$F—FPBM-D12), in the brain is comparable to that of the non-deuterated $^{18}$F-III-1 ($^{18}$F—FPBM), reported previously.

The novel new deuterated compound, $^{18}$F-III-3 ($^{18}$F—FPBM-D12), can be useful for imaging patients before and after taking serotonin reuptake inhibitors (SSRIs) for monitoring the drug effects. The "cold" agent as described above may also be useful for specific therapy where blocking serotonin uptake is indicated.

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

REFERENCES

[1] Meanwell N A. Synopsis of some recent tactical application of bioisosteres in drug design. J. Med. Chem. 2011; 54:2529-91.

[2] Kuchar M and Mamat C. Methods to Increase the Metabolic Stability of (18)F-Radiotracers. Molecules 2015; 20:16186-220.

[3] Guengerich F P. Kinetic deuterium isotope effects in cytochrome P450 oxidation reactions. J Labelled Comp Radiopharm 2013; 56:428-31.

[4] Howland R H. Deuterated Drugs. J. Psychosoc. Nurs. Ment. Health Serv. 2015; 53:13-6.

[5] Gant T G. Using deuterium in drug discovery: leaving the label in the drug. J. Med. Chem. 2014; 57:3595-611.

[6] Jankovic J, Jimenez-Shahed J, Budman C, Coffey B, Murphy T, Shprecher D, et al. Deutetrabenazine in Tics Associated with Tourette Syndrome. Tremor Other Hyperkinet Mov (N Y) 2016; 6:422.

[7] Frank S, Testa C M, Stamler D, Kayson E, Davis C, Edmondson M C, et al. Effect of Deutetrabenazine on Chorea Among Patients With Huntington Disease: A Randomized Clinical Trial. JAMA 2016; 316:40-50.

[8] Garay R P and Grossberg G T. AVP-786 for the treatment of agitation in dementia of the Alzheimer type. Expert Opin. Investig. Drugs 2017; 26:121-32.

[9] Fowler J S, Wang G J, Logan J, Xie S, Volkow N D, MacGregor R R, et al. Selective reduction of radiotracer trapping by deuterium substitution: comparison of carbon-11-L-deprenyl and carbon-11-deprenyl-$D_2$ for MAO B mapping. J. Nucl. Med. 1995; 36:1255-62.

[10] Logan J, Fowler J S, Volkow N D, Wang G J, MacGregor R R, and Shea C. Reproducibility of repeated measures of deuterium substituted [11C]L-deprenyl ([11C]L-deprenyl-D2) binding in the human brain. Nucl. Med. Biol. 2000; 27:43-9.

[11] Fowler J S, Logan J, Volkow N D, and Wang G J. Translational Neuroimaging: Positron Emission Tomography Studies of Monoamine Oxidase. Mol. Imaging Biol. 2005; 7:1-11.

[12] Fowler J S, MacGregor R R, Wolf A P, Arnett C D, Dewey S L, Schlyer D, et al. Mapping human brain monoamine oxidase A and B with 11C-labeled suicide inactivators and PET. Science 1987; 235:481-5.

[13] Lin K S, Ding Y S, Kim S W, and Kil K E. Synthesis, enantiomeric resolution, F-18 labeling and biodistribution of reboxetine analogs: promising radioligands for imaging the norepinephrine transporter with positron emission tomography. Nucl. Med. Biol. 2005; 32:415-22.

[14] Ding Y-S, Lin K-S, and Logan J. PET imaging of norepinephrine transporters. Curr. Pharm. Des. 2006; 12:3831-45.

[15] Beauregard J M and Beaulieu A. How we read FCH-PET/C T for prostate cancer. Cancer Imaging 2016; 16:41.

[16] Nitsch S, Hakenberg O W, Heuschkel M, Drager D, Hildebrandt G, Krause B J, et al. Evaluation of Prostate Cancer with 11C- and 18F-Choline PET/C T: Diagnosis and Initial Staging. J. Nucl. Med. 2016; 57:38s-42s.

[17] Smith G, Zhao Y, Leyton J, Shan B, Nguyen Q D, Perumal M, et al. Radiosynthesis and preclinical evaluation of [(18)F]fluoro-[1,2-(2)H(4)]choline. Nucl. Med. Biol. 2011; 38:39-51.

[18] Witney T H, Alam I S, Turton D R, Smith G, Carroll L, Brickute D, et al. Evaluation of deuterated 18F- and 11C-labeled choline analogs for cancer detection by positron emission tomography. Clin. Cancer Res. 2012; 18:1063-72.

[19] Goswami R, Ponde D, Kung M, Hou C, Kilbourn M, and Kung H. Fluoroalkyl derivatives of dihydrotetrabenazine as positron emission tomography imaging agents targeting vesicular monoamine transporters. Nucl. Med. Biol. 2006; 33:685-94.

[20] Kilbourn M, Hockley B, Lee L, Hou C, Goswami R, Ponde D, et al. Pharmacokinetics of [(18)F]fluoroalkyl derivatives of dihydrotetrabenazine in rat and monkey brain. Nucl. Med. Biol. 2007; 34:233-7.

[21] Siderowf A, Pontecorvo M J, Shill H A, Mintun M A, Arora A, Joshi A D, et al. PET imaging of amyloid with Florbetapir F 18 and PET imaging of dopamine degeneration with 18F-AV-133 (florbenazine) in patients with Alzheimer disease and Lewy body disorders. BMC Neurol. 2014; 14:79.

[22] Hsiao I T, Weng Y H, Lin W Y, Hsieh C J, Wey S P, Yen T C, et al. Comparison of 99mTc-TRODAT-1 SPECT and 18 F-AV-133 PET imaging in healthy controls and Parkinson's disease patients. Nucl. Med. Biol. 2014; 41:322-9.

[23] Hsiao I T, Weng Y H, Hsieh C J, Lin W Y, Wey S P, Kung M P, et al. Correlation of Parkinson disease severity and 18F-DTBZ positron emission tomography. JAMA Neurol 2014; 71:758-66.

[24] Okamura N, Villemagne V, Drago J, Pejoska S, Dhamija R, Mulligan R, et al. In Vivo Measurement of Vesicular Monoamine Transporter Type 2 Density in Parkinson Disease with 18F-AV-133. J. Nucl. Med. 2010; 51:223-8.

[25] Villemagne V L, Okamura N, Pejoska S, Drago J, Mulligan R S, Chetelat G, et al. In vivo assessment of vesicular monoamine transporter type 2 in dementia with lewy bodies and Alzheimer disease. Arch. Neurol. 2011; 68:905-12.

[26] Kung M, Hou C, Lieberman B, Oya S, Ponde D, Blankemeyer E, et al. In Vivo Imaging of {beta}-Cell Mass in Rats Using 18F—FP-(+)-DTBZ: A Potential PET Ligand for Studying Diabetes Mellitus. J. Nucl. Med. 2008; 49:1171-6.

[27] Raffo A, Hancock K, Polito T, Xie Y, Andan G, Witkowski P, et al. Role of vesicular monoamine transporter type 2 in rodent insulin secretion and glucose metabolism revealed by its specific antagonist tetrabenazine. J. Endocrinol. 2008; 198:41-9.

[28] Harris P E, Ferrara C, Barba P, Polito T, Freeby M, and Maffei A. VMAT2 gene expression and function as it applies to imaging beta-cell mass. J. Mol. Med. 2008; 86:5-16.

[29] Harris P E, Farwell M D, and Ichise M. PET quantification of pancreatic VMAT 2 binding using (+) and (−) enantiomers of [(1)(8)F]FP-DTBZ in baboons. Nucl. Med. Biol. 2013; 40:60-4.

[30] Freeby M, Ichise M, and Harris P E. Vesicular monoamine transporter, type 2 (vmat2) expression as it compares to insulin and pancreatic polypeptide in the head, body and tail of the human pancreas. Islets 2012; 4:393-7.

[31] Normandin M D, Petersen K F, Ding Y S, Lin S F, Naik S, Fowles K, et al. In vivo imaging of endogenous pancreatic beta-cell mass in healthy and type 1 diabetic subjects using 18F-fluoropropyl-dihydrotetrabenazine and PET. J. Nucl. Med. 2012; 53:908-16.

[32] Eriksson O, Jahan M, Johnstrom P, Korsgren O, Sundin A, Halldin C, et al. In vivo and in vitro characterization of [18F]—FE-(+)-DTBZ as a tracer for beta-cell mass. Nucl. Med. Biol. 2010; 37:357-63.

[33] Jahan M, Eriksson O, Johnstrom P, Korsgren O, Sundin A, Johansson L, et al. Decreased defluorination using the novel beta-cell imaging agent [18F]F E-DTBZ-d4 in pigs examined by PET. EJNMMI Res 2011; 1:33.

[34] Gauthier S, Albert M, Fox N, Goedert M, Kivipelto M, Mestre-Ferrandiz J, et al. Why has therapy development for dementia failed in the last two decades? Alzheimers Dement 2016; 12:60-4.

[35] Harrison J R and Owen M J. Alzheimer disease: the amyloid hypothesis on trial. Br. J. Psychiatry 2016; 208: 1-3.

[36] Mathis C A, Mason N S, Lopresti B J, and Klunk W E. Development of positron emission tomography beta-amyloid plaque imaging agents. Semin. Nucl. Med. 2012; 42:423-32.

[37] Zeng F and Goodman M M. Fluorine-18 radiolabeled heterocycles as PET tracers for imaging beta-amyloid plaques in Alzheimer disease. Curr. Top. Med. Chem. 2013; 13:909-19.

[38] Kung H. The 0-amyloid hypothesis in Alzheimer disease: Seeing is believing. ACS Med Chem Lett 2012; 3:265-7.

[39] Villemagne V L, Dore V, Bourgeat P, Burnham S C, Laws S, Salvado O, et al. Abeta-amyloid and Tau Imaging in Dementia. Semin. Nucl. Med. 2017; 47:75-88.

[40] Rowe C C, Pejoska S, Mulligan R S, Jones G, Chan J G, Svensson S, et al. Head-to-Head Comparison of 11C-PiB and 18F-AZD4694 (NAV4694) for beta-Amyloid Imaging in Aging and Dementia. J. Nucl. Med. 2013; 54:880-6.

[41] Nelissen N, Van Laere K, Thurfjell L, Owenius R, Vandenbulcke M, Koole M, et al. Phase 1 study of the Pittsburgh compound B derivative 18F-flutemetamol in healthy volunteers and patients with probable Alzheimer disease. J. Nucl. Med. 2009; 50:1251-9.

[42] Rowe C C, Jones G, Dore V, Pejoska S, Margison L, Mulligan R S, et al. Standardized Expression of 18F-NAV4694 and 11C-PiB beta-Amyloid PET Results with the Centiloid Scale. J. Nucl. Med. 2016; 57:1233-7.

[43] Rowe C C, Pejoska S, Mulligan R S, Jones G, Chan J G, Svensson S, et al. Head-to-head comparison of 11C-PiB and 18F-AZD4694 (NAV4694) for beta-amyloid imaging in aging and dementia. J. Nucl. Med. 2013; 54:880-6.

[44] Kung H, Choi S, Qu W, Zhang W, and Skovronsky D. (18)F Stilbenes and Styrylpyridines for PET Imaging of Abeta Plaques in Alzheimer Disease: A Miniperspective. J. Med. Chem. 2009; 53:933-41.

[45] Zhu L, Ploessl K, and Kung H F. PET/SPECT imaging agents for neurodegenerative diseases. Chem. Soc. Rev. 2014.

[46] Choi S, Golding G, Zhuang Z, Zhang W, Lim N, Hefti F, et al. Preclinical properties of 18F-AV-45: a PET agent for Aβ plaques in the brain. J. Nucl. Med. 2009; 50:1887-94.

[47] Wong D, Rosenberg P, Zhou Y, Kumar A, Raymont V, Ravert H, et al. In Vivo Imaging of Amyloid Deposition in Alzheimer Disease Using the Radioligand 18F-AV-45 (Flobetapir F 18). J. Nucl. Med. 2010; 51:913-20.

[48] Patt M, Schildan A, Barthel H, Becker G, Schultze-Mosgau M H, Rohde B, et al. Metabolite analysis of [18F]Florbetaben (BAY 94-9172) in human subjects: a substudy within a proof of mechanism clinical trial. J. Radioanal. Nucl. Chem. 2010; 284:557-62.

[49] Rowe C, Ackerman U, Browne W, Mulligan R, Pike K, O'Keefe G, et al. Imaging of amyloid beta in Alzheimer disease with (18)F-BAY94-9172, a novel PET tracer: proof of mechanism. Lancet Neurol. 2008; 7:129-35.

[50] Bousman C A, Forbes M, Jayaram M, Eyre H, Reynolds C F, Berk M, et al. Antidepressant prescribing in the precision medicine era: a prescriber's primer on pharmacogenetic tools. BMC Psychiatry 2017; 17:60.

[51] Kambeitz J P and Howes O D. The serotonin transporter in depression: Meta-analysis of in vivo and post mortem findings and implications for understanding and treating depression. J. Affect. Disord. 2015; 186:358-66.

[52] Spies M, Knudsen G M, Lanzenberger R, and Kasper S. The serotonin transporter in psychiatric disorders: insights from PET imaging. Lancet Psychiatry 2015; 2:743-55.

[53] Oya S, Choi S, Kung M, and Kung H. 5-Chloro-2-(2'-((dimethylamino)methyl)-4'-iodophenylthio)benzenamine: a new serotonin transporter ligand. Nucl. Med. Biol. 2007; 34:129-39.

[54] Kung H, Newman S, Choi S, Oya S, Hou C, Zhuang Z, et al. 2-(2-(dimethylaminomethyl)phenoxy)-5-iodophenylamine: an improved serotonin transporter imaging agent. J. Med. Chem. 2004; 47:5258-64.

[55] Wang J L, Parhi A K, Oya S, Lieberman B, Kung M P, and Kung H F. 2-(2'-((Dimethylamino)methyl)-4'-(3-[(18) F]fluoropropoxy)-phenylthio)benzenamine for positron emission tomography imaging of serotonin transporters. Nucl. Med. Biol. 2008; 35:447-58.

[56] Wang J L, Deutsch E C, Oya S, and Kung H F. FlipADAM: a potential new SPECT imaging agent for the serotonin transporter. Nucl. Med. Biol. 2010; 37:577-86.

[57] Huang Y, Zheng M Q, and Gerdes J M. Development of effective PET and SPECT imaging agents for the serotonin transporter: has a twenty-year journey reached its destination? Curr. Top. Med. Chem. 2010; 10:1499-526.

[58] Mavel S, Meheux N, Guilloteau D, and Emond P. Synthesis and in vitro evaluation of fluorinated diphenyloxide derivatives and sulfur analogs as serotonin transporter ligands. Bioorg. Med. Chem. 2010; 18:236-41.

[59] Jarkas N, Voll R J, Williams L, and Goodman M M. Validation of two fluoro-analogues of N,N-dimethyl-2-(2'-amino-4'-hydroxymethyl-phenylthio)benzylamine as serotonin transporter imaging agents using microPET. Nucl. Med. Biol. 2010; 37:593-603.

[60] Kang H H, Wang C H, Chen H C, Li I H, Cheng C Y, Liu R S, et al. Investigating the effects of noise-induced hearing loss on serotonin transporters in rat brain using 4-[(18)F]-ADAM/small animal PET. Neuroimage 2012.

[61] Huang Y Y, Huang W S, Ma K H, Chou T K, Kuo Y Y, Cheng C Y, et al. Synthesis and comparison of 4-[18F]F-ADAM, 2-[18F]F-ADAM, N-Desmethyl-4-[18F]F-ADAM and [18F]F-AFM as serotonin transporter imaging agents. Appl. Radiat. Isot. 2012; 70:2298-307.

[62] Chen Y A, Huang W S, Lin Y S, Cheng C Y, Liu R S, Wang S J, et al. Characterization of 4-[18F]-ADAM as an imaging agent for SERT in non-human primate brain using PET: a dynamic study. Nucl. Med. Biol. 2012; 39:279-85.

[63] Hesse S, Brust P, Mading P, Becker G A, Patt M, Seese A, et al. Imaging of the brain serotonin transporters (SERT) with (18)F-labelled fluoromethyl-McN5652 and PET in humans. Eur. J. Nucl. Med. Mol. Imaging 2012; 39:1001-11.

[64] Paterson L M, Kornum B R, Nutt D J, Pike V W, and Knudsen G M. 5-H T radioligands for human brain imaging with PET and SPECT. Med. Res. Rev. 2013; 33:54-111.

[65] Huang W S, Huang S Y, Ho P S, Ma K H, Huang Y Y, Yeh C B, et al. PET imaging of the brain serotonin transporters (SERT) with N,N-dimethyl-2-(2-amino-4-[18F]fluorophenylthio)benzylamine (4-[18F]-ADAM) in humans: a preliminary study. Eur. J. Nucl. Med. Mol. Imaging 2013; 40:115-24.

[66] Szabo Z, Kao P F, Scheffel U, Suehiro M, Mathews W B, Ravert H T, et al. Positron emission tomography imaging of serotonin transporters in the human brain using [$^{11}$C](+)McN5652. Synapse 1995; 20:37-43.

[67] Zessin J, Eskola O, Brust P, Bergman J, Steinbach J, Lehikoinen P, et al. Synthesis of S-([18F]fluoromethyl)-(+)-McN5652 as a potential PET radioligand for the serotonin transporter. Nucl. Med. Biol. 2001; 28:857-63.

[68] Stehouwer J S and Goodman M M. (11) C and (18) F PET radioligands for the serotonin transporter (SERT). J Labelled Comp Radiopharm 2013; 56:114-9.

[69] Wilson A A, Ginovart N, Schmidt M, Meyer J H, Threlkeld P G, and Houle S. Novel radiotracers for imaging the serotonin transporter by positron emission tomography: synthesis, radiosynthesis, and in vitro and ex vivo evaluation of $^{11}$C-labeled 2-(phenylthio)araalkylamines. J. Med. Chem. 2000; 43:3103-10.

[70] Wilson A A, Ginovart N, Hussey D, Meyer J, and Houle S. In vitro and in vivo characterisation of [11C]-DASB: a probe for in vivo measurements of the serotonin transporter by positron emission tomography. Nucl. Med. Biol. 2002; 29:509-15.

[71] Kupers R, Frokjaer V G, Erritzoe D, Naert A, Budtz-Joergensen E, Nielsen F A, et al. Serotonin transporter binding in the hypothalamus correlates negatively with tonic heat pain ratings in healthy subjects: a [11C]DASB PET study. Neuroimage 2011; 54:1336-43.

[72] Ginovart N, Sun W, Wilson A A, Houle S, and Kapur S. Quantitative validation of an intracerebral beta-sensitive microprobe system to determine in vivo drug-induced receptor occupancy using [11C]raclopride in rats. Synapse 2004; 52:89-99.

[73] Kim E, Howes O D, Park J W, Kim S N, Shin S A, Kim B H, et al. Altered serotonin transporter binding potential in patients with obsessive-compulsive disorder under escitalopram treatment: [11C]DASB PET study. Psychol. Med. 2015:1-10.

[74] Oya S, Choi S R, Coenen H, and Kung H F. New PET imaging agent for the serotonin transporter: [(18)F]ACF (2-[(2-amino-4-chloro-5-fluorophenyl)thio]-N,N-dimethyl-benzenmethanamine). J. Med. Chem. 2002; 45:4716-23.

[75] Huang Y, Bae S A, Zhu Z, Guo N, Roth B L, and Laruelle M. Fluorinated diaryl sulfides as serotonin transporter ligands: synthesis, structure-activity relationship study, and in vivo evaluation of fluorine-18-labeled compounds as PET imaging agents. J. Med. Chem. 2005; 48:2559-70.

[76] Shiue G, Choi S, Fang P, Hou C, Acton P, Cardi C, et al. N,N-dimethyl-2-(2-amino-4-(18)F-fluorophenylthio)-benzylamine (4-(18)F-ADAM): an improved PET radioligand for serotonin transporters. J. Nucl. Med. 2003; 44:1890-7.

[77] Wang J, Parhi A, Oya S, Lieberman B, and Kung H. In vivo characterization of a series of 18F-diaryl sulfides (18F-2-(2'-((dimethylamino)methyl)-4'-(fluoroalkoxy) phenylthio)benzenamine) for PET imaging of the serotonin transporter. J. Nucl. Med. 2009; 50:1509-17.

[78] Wang J, Oya S, Parhi A, Lieberman B, Ploessl K, Hou C, et al. In vivo studies of the SERT-selective [18F]FPBM and VMAT2-selective [18F]AV-133 radiotracers in a rat model of Parkinson's disease. Nucl. Med. Biol. 2010; 37:479-86.

[79] Qiao H, Zhang Y, Wu Z, Zhu L, Choi S R, Ploessl K, et al. One-step preparation of [(18)F]FPBM for PET imaging of serotonin transporter (SERT) in the brain. Nucl. Med. Biol. 2016; 43:470-7.

[80] Zhu L, Li G, Choi S R, Plossl K, Chan P, Qiao H, et al. An improved preparation of [18F]FPBM: A potential serotonin transporter (SERT) imaging agent. Nucl. Med. Biol. 2013; 40:974-9.

What is claimed is:

1. A compound having Formula II-B:

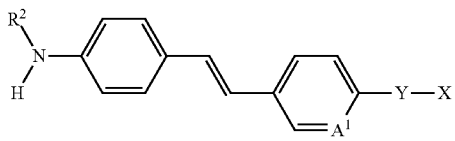

(II-B)

or a pharmaceutically acceptable salt thereof, wherein:
$R^2$ is $CD_3$;
X is $^{18}F$ or F;
Y is $-[O(CR^aR^b)_2]_m-$, wherein $R^a$ and $R^b$ are each independently hydrogen or deuterium atoms;
m is 3; and
$A^1$ is N or CH.

2. The compound of claim 1, or a pharmaceutically acceptable salt thereof, wherein Y is $-[O(CR^aR^b)_2]_3-$.

3. The compound of claim 1, having Formula II-C:

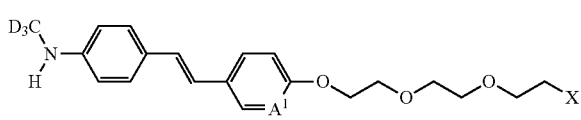

(II-C)

or a pharmaceutically acceptable salt thereof, wherein:
$A^1$ is N or CH; and
X is $^{18}F$ or F.

4. The compound of claim 3, or a pharmaceutically acceptable salt thereof,
wherein $A^1$ is N and X is $^{18}F$.

5. The compound of claim 2, or a pharmaceutically acceptable salt thereof,
wherein $A^1$ is N and X is $^{18}F$.

6. A pharmaceutical composition comprising the compound of claim 1, or a pharmaceutically acceptable salt thereof, and a pharmaceutically acceptable carrier.

7. A method of in vivo imaging, comprising
administering an effective amount of the compound of claim 1 wherein X is $^{18}F$, or a pharmaceutically acceptable salt thereof to a subject; and
scanning said subject to detect the pattern of positron emission tomography, whereby an image is generated from the pattern of positron emission.

8. A pharmaceutical composition comprising the compound of claim 4, or a pharmaceutically acceptable salt thereof, and a pharmaceutically acceptable carrier.

9. A method of in vivo imaging, comprising
administering an effective amount of the compound of claim 4 or a pharmaceutically acceptable salt thereof to a subject; and
scanning said subject to detect the pattern of positron emission tomography, whereby an image is generated from the pattern of positron emission.

10. A pharmaceutical composition comprising the compound of claim 5, or a pharmaceutically acceptable salt thereof, and a pharmaceutically acceptable carrier.

11. A method of in vivo imaging, comprising
administering an effective amount of the compound of claim 5 or a pharmaceutically acceptable salt thereof to a subject; and
scanning said subject to detect the pattern of positron emission tomography, whereby an image is generated from the pattern of positron emission.

12. The compound of claim 3, or a pharmaceutically acceptable salt thereof, wherein $A^1$ is N and X is F.

13. The compound of claim 2, or a pharmaceutically acceptable salt thereof, wherein $A^1$ is N and X is F.

* * * * *